United States Patent
Angibaud et al.

(10) Patent No.: US 11,130,751 B2
(45) Date of Patent: Sep. 28, 2021

(54) QUINOXALINE AND PYRIDOPYRAZINE DERIVATIVES AS PI3K-BETA INHIBITORS

(71) Applicant: JANSSEN PHARMACEUTICA NV, Beerse (BE)

(72) Inventors: Patrick René Angibaud, Issy-les Moulineaux (FR); Olivier Alexis Georges Querolle, Issy-les Moulineaux (FR); Didier Jean-Claude Berthelot, Issy-les Moulineaux (FR); Christophe Meyer, Issy-les Moulineaux (FR); Matthieu Philippe Victor Willot, Düsseldorf (DE); Lieven Meerpoel, Beerse (BE); Thierry François Alain Jean Jousseaume, Schaffhausen (CH)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/499,421

(22) PCT Filed: Mar. 29, 2018

(86) PCT No.: PCT/EP2018/058175
§ 371 (c)(1),
(2) Date: Sep. 30, 2019

(87) PCT Pub. No.: WO2018/178280
PCT Pub. Date: Oct. 4, 2018

(65) Prior Publication Data
US 2020/0181132 A1    Jun. 11, 2020

(30) Foreign Application Priority Data

Mar. 29, 2017 (EP) .................................... 17163625

(51) Int. Cl.
*C07D 413/14* (2006.01)
*C07D 495/10* (2006.01)
*A61P 35/00* (2006.01)

(52) U.S. Cl.
CPC ............ *C07D 413/14* (2013.01); *A61P 35/00* (2018.01); *C07D 495/10* (2013.01)

(58) Field of Classification Search
CPC ...... C07D 413/14; C07D 495/10; A61P 35/00
USPC .................................................. 514/210.16
See application file for complete search history.

(56) References Cited

U.S. PATENT DOCUMENTS

| 2013/0157977 A1 | 6/2013 | Rivero et al. |
| 2016/0244432 A1 | 8/2016 | Xu et al. |

FOREIGN PATENT DOCUMENTS

| WO | 2007/103756 | 9/2007 |
| WO | 2008/014219 | 1/2008 |
| WO | 2009/021083 A1 | 2/2009 | |
| WO | WO-2009021083 A1 * | 2/2009 | ............ A61P 35/04 |
| WO | 2009/088990 | 7/2009 | |
| WO | 2010/091808 A1 | 8/2010 | |
| WO | 2010/108074 A2 | 9/2010 | |
| WO | 2011/041399 | 4/2011 | |
| WO | 2011/110545 | 9/2011 | |
| WO | 2012/047538 | 4/2012 | |
| WO | 2012/116237 | 8/2012 | |
| WO | 2013/028263 | 2/2013 | |
| WO | 2013/095761 | 6/2013 | |
| WO | 2014/009295 A1 | 1/2014 | |
| WO | 2014/009296 | 1/2014 | |
| WO | 2016/097347 | 12/2014 | |
| WO | 2016/097359 | 6/2016 | |
| WO | 2017/060406 | 4/2017 | |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
International Search Report and Written Opinion for Application No. PCT/EP2018/058175 dated May 29, 2018.
International Search Report and Written Opinion for Application No. PCT/EP2016/073962 dated Dec. 15, 2016.
International Search Report and Written Opinion for Application No. PCT/EP2017/064671 dated Sep. 26, 2017.
B. Vanhasesbroeck et al, Signaling by distinct classes of phosphoinositide 3-kinases, Experimental Cell Research, 1999, pp. 239-254, 253.
David Stokoe et al, Dual role of phosphatidylinositol-3,4,5-trisphosphate in the activation of protein kinase B, Science, Jul. 25, 1997, pp. 567-570, 277.
Dr Calnan et al, The FoxO code, Oncogene, 2008, pp. 2276-2288, 27.
Kevin D. Courtney En Al, The PI3K pathways as drug target in human cancer, Journal of clinical oncology, Feb. 20, 2010, pp. 1075-1083, 28.

(Continued)

*Primary Examiner* — Kristin A Vajda

(57) ABSTRACT

The present invention relates to substituted quinoxaline and pyridopyrazine derivatives of Formula (I)

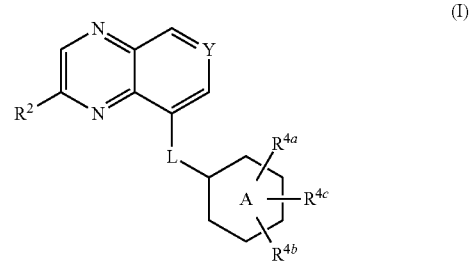

wherein the variables have the meaning defined in the claims. The compounds according to the present invention are useful as pI3Kβ inhibitors. The invention further relates to pharmaceutical compositions comprising said compounds as an active ingredient as well as the use of said compounds as a medicament.

10 Claims, No Drawings

(56) References Cited

OTHER PUBLICATIONS

L Zhao et al, Class I PI3K in oncogenic cellular transformation, Oncogene, 2008, pp. 5486-5496, 27.

Michael P. Myers, The lipid phosphatase activity of PTEN is crital for its tumor supressor function, Proc. Natl. Acad. Sci. USA, Nov. 1998, pp. 13513-13518, vol. 95.

Rute B. Marques et al, High Efficacy of Combination Therapy Using PI3K/AKT Inhibitors with Androgen Deprivation in Prostate Cancer Preclinical Models, European Urology, 2014, pp. 1177-1185, 67.

Shaun P Jackson, PI 3-kinase p 110b a new target for antithrombotic therapy. Nature medicine, May 2005, pp. 507-514, 11.

Shidong Jia et al, Essential roles of PI(3)K-p110δ in cell growth, metabolism an tumorigenesis, Letters, Aug. 7, 2008, pp. 776-779, vol. 454.

Susan Wee et al, PTEN-deficient cancers depend on PIL3CB, PNAS, Sep. 2, 2008, pp. 13057-13062, 105.

W. Hickinbottom, corresponding part of the English edition Reactions of Organic Compounds, Chemical encyclopaedia, 1939, pp. 277-280.

Wu Kui et al, Multisubstituted quinoxalines and pyrido[2,3-d]pyrimidines: Synthesis and SAR study as tyrosine kinase c-Met inhibitors, Bioorganic & Medicinal chemistry Letters, Aug. 27, 2012, pp. 6368-6372, vol. 22 No. 20.

\* cited by examiner

QUINOXALINE AND PYRIDOPYRAZINE DERIVATIVES AS PI3K-BETA INHIBITORS

CROSS REFERENCE TO RELATED APPLICATIONS

This application is a national stage application of International Patent Application No. PCT/EP2018/058175, filed 29 Mar. 2018, which claims priority from EP Application 17163625.1 filed 29 Mar. 2017. The complete disclosures of the aforementioned related patent applications are hereby incorporated herein by reference for all purposes.

FIELD OF THE INVENTION

The present invention relates to substituted quinoxaline and pyridopyrazine derivatives linked to N-containing aromatic rings useful as PI3Kβ inhibitors. The invention further relates to pharmaceutical compositions comprising said compounds as an active ingredient as well as the use of said compounds as a medicament.

BACKGROUND OF THE INVENTION

There are three classes of phosphoinositide-3-kinases (PI3Ks): class I, class II and class III. Class I PI3Ks are the most associated with human cancer [K. D Courtney, R. B. Corcoran and J. A. Engelman (2010), *Journal of Clinical Oncology.*, 28; 1075]. The class I phosphoinositide-3-kinases (PI3Ks) are divided into 2 subclasses: class $I_A$, composed of a p110 catalytic subunit (p110a, p110b or p110d) and a p85 regulatory subunit (p85a, p55a and p50a, p85b or p55 g) and class $I_B$ PI3K represented by the p110 g catalytic subunit and the p101 and p84 regulatory subunits [B. Vanhaesebroeck and M. D. Waterfield (1999) *Experimental Cell Research.*, 253, 239-254]. The class IA PI3Ks are activated in a variety of solid and non-solid tumors via mutation or deletion of the tumor suppressor PTEN (phosphatase and tensin homolog) or in the case of p110a by activating mutations [K. D Courtney, R B. Corcoran and J. A. Engelman (2010), *Journal of Clinical Oncology.*, 28; 1075]. PI3Ks can also be activated by receptor tyrosine kinases (RTKs); p110b can be activated by G-protein coupled receptors [K. D Courtney, R B. Corcoran and J. A. Engelman (2010), *Journal of Clinical Oncology.*, 28; 1075]. Once activated the phosphoinositide-3-kinases catalyze the phosphorylation of phosphatidyl 4,5-diphosphate leading to the generation of phosphatidyl, 3,4,5-triphosphate (PIP3) [Zhao L., Vogt P. K. (2008) Oncogene 27, 5486-5496]. PTEN antagonizes the activity of the PI3Ks through the dephosphorylation PIP3 [Myers M. P., Pass I., Batty I. H., Van der Kaay J., Stolarov J. P., Hemmings B. A., Wigler M. H., Downes C. P., Tonks N. K. (1998) *Proc. Natl. Acad. Sci. U.S.A.* 95, 13513-13518]. The PIP3 generated by activation of PI3K or sustained by the inactivation of PTEN binds to a subset of lipid-binding domains in downstream targets such as the pleckstrin homology domain of the oncogene Akt thereby recruiting it to the plasma membrane [Stokoe D., Stephens L. R., Copeland T., Gaffney P. R, Reese C. B., Painter G. F., Holmes A. B., McCormick F., Hawkins P. T. (1997) *Science* 277. 567-570]. Once at the plasma membrane Akt phosphorylates several effector molecules that are involved in numerous biologically relevant processes such as metabolism, differentiation, proliferation, longevity and apoptosis [D. R. Calnan and A. Brunet (2008) *Oncogene* 27; 2276)].

Several studies suggest a key role for p110b in PTEN-deficient tumors. For example the genetic knockout of p110b, but not p110a, is able to block tumor formation and Akt activation driven by Pten loss in the anterior prostate in a mouse model [Jia S, Liu Z, Zhang S, Liu P, Zhang L, Lee S H, Zhang J, Signoretti S, Loda M, Roberts T M, Zhao J J. *Nature* 2008; 454:776-9]. Furthermore other studies have shown that a subset of PTEN-deficient human tumor cell lines is sensitive to inactivation of p110b rather than p110a [Wee S, Wiederschain D, Maira S M, Loo A, Miller C, deBeaumont R, Stegmeier F, Yao Y M, Lengauer C (2008) *Proc. Natl. Acad Sci* (USA); 105 13057]. PTEN deficiency either by genetic inactivation or reduced expression frequently occurs in human cancers such as GBM, endometrial, lung, breast cancers and prostate cancer among others [K. D Courtney, R. B. Corcoran and J. A. Engelman (2010), *Journal of Clinical Oncology.*, 28; 1075].

These studies suggest that treatment of PTEN-deficient cancer with agents that inhibition p110b may be therapeutically beneficial. In addition to its role in cancer, p110b may be a target for antithrombotic therapy. It has been reported in mouse models that PI3Kb inhibition can prevent stable integrin $a_{IIb}b_3$ adhesion contacts that eliminates occlusive thrombus formation without prolongation of bleed time [S. P. Jackson et al. (2005) *Nature Medicine.*, 11, 507-514].

Furthermore, the phosphatidylinositol-4,5-bisphosphate 3-kinase (PI3K)/AKT pathway is frequently activated during prostate cancer (PCa) progression through loss or mutation of the phosphatase and tensin homolog (PTEN) gene. Following the androgen receptor (AR) pathway, it is the second major driver of PCa growth. Combination with hormonal therapy improved efficacy of PI3K/AKT-targeted agents in PTEN-negative PCa models. Upregulation of AR-target genes upon PI3K/AKT inhibition suggests a compensatory crosstalk between the PI3K-AR pathways which, for optimal efficacy treatment, could require cotargeting of the AR axis [Marques R B, et al., High Efficacy of Combination Therapy Using PI3K/AKT Inhibitors with Androgen Deprivation in Prostate Cancer Preclinical Models. *Eur Urol* (2014), http://dx.doi.org/10.1016/j.eururo.2014.08.053]. Therefore PI3K inhibitors can be advantageously combined with anti-androgen therapies including androgen receptor antagonists and inhibitors of androgen biosynthesis in PTEN-negative prostate cancers.

WO 2012/116237 discloses heterocyclic entities that modulate PI3 kinase activity.

WO 2011/123751 describes heterocyclic compounds as selective inhibitors of PI3K activity.

WO 2011/022439 discloses heterocyclic entities that modulate PI3 kinase activity.

WO 2008/014219 describes thiozolidinedione derivatives as PI3 kinase inhibitors.

WO 2013/028263 relates to pyrazolopyrimidine derivatives as PI3 kinase inhibitors.

WO 2012/047538 relates to benzimidazole derivatives as PI3 kinase inhibitors.

WO 2013/095761 relates to imidazopyridine derivatives as PI3 kinase inhibitors.

US 2013/0157977 relates to benzimidazole boronic acid derivatives as PI3 kinase inhibitors.

WO 2009/021083 describes quinoxaline derivatives as PI3 kinase inhibitors.

WO 2007/103756 describes the preparation of thiazolones for use as PI3 kinase inhibitors.

WO 2011/041399 describes benzimidazolyl (morpholinyl)purines and related compounds as PI3Kδ inhibitors and their preparation and use for the treatment of PI3K-mediated diseases.

WO 2009/088990 describes the preparation of pyrazolo pyrimidines and other heterocyclic compounds as therapeutic PI3 kinase modulators.

WO2016/097347 relates to substituted imidazopyridazine derivatives useful as PI3Kβ inhibitors.

WO2016/097359 relates to relates to heterocyclyl linked imidazopyridazine derivatives useful as PI3Kβ inhibitors.

There is thus a strong need for novel PI3Kβ kinase inhibitors thereby opening new avenues for the treatment or prevention of cancer, in particular PTEN-deficient cancers, more in particular prostate cancer. It is accordingly an object of the present invention to provide such compounds.

SUMMARY OF THE INVENTION

It has been found that the compounds of the present invention are useful as PI3Kβ inhibitors. The compounds according to the invention and compositions thereof, may be useful for the treatment or prevention, in particular for the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

This invention concerns compounds of Formula (I)

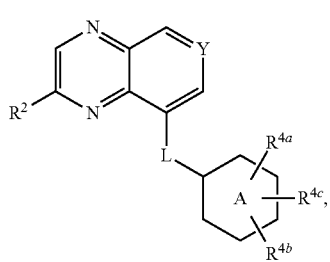

(I)

tautomers and stereoisomeric forms thereof, wherein

Y represents $CR^3$ or N;

L represents —CH($C_{1-4}$alkyl)-$CH_2$—, —$CH_2$—CH($C_{1-4}$alkyl)-, —CH($C_{1-4}$alkyl)-CH($C_{1-4}$alkyl)-, —$CHR^{1a}$—X—, or —X—$CHR^{1c}$—;

X represents O, S, or $NR^{1b}$;

$R^{1a}$ represents $C_{1-4}$alkyl;

$R^{1c}$ represents hydrogen or $C_{1-4}$alkyl;

$R^{1b}$ represents hydrogen, $C_{1-4}$alkyl, —$CH_2$—C(=O)—$NR^{6a}R^{6b}$, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—;

$R^2$ represents

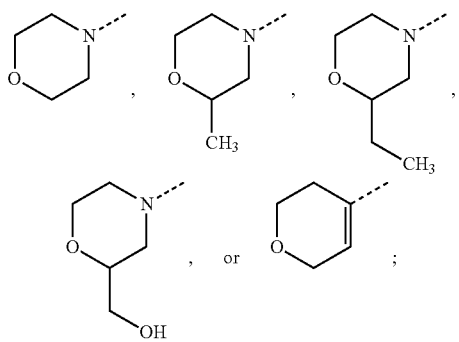

$R^{6a}$ and $R^{6b}$ each independently are selected from the group consisting of hydrogen and $C_{1-4}$alkyl;

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —NH($C_{1-4}$alkyl), and —N($C_{1-4}$alkyl)$_2$;

$R^3$ represents $R^7$, —(C=O)H, —(C=O)—$C_{1-4}$alkyl, —(C=O)—$NR^{5a}R^{5b}$, —(C=O)—$OR^{5c}$, —C(=O)—$Het^1$, —C(=O)—NH—$Het^2$, $C_{1-4}$alkyl, —CH=N—OH, —CH(OH)—$CH_2$—$NR^{5d}R^{5e}$, —CH(OH)—$CH_2$-$Het^1$, —CH(OH)—$C_{1-4}$alkyl, —C(OH)($C_{1-4}$alkyl)$_2$, halo, or $R^3$ represents $C_{1-4}$alkyl substituted with one substituent selected from the group consisting of hydroxyl, fluoro, —$NR^{5f}R^{5g}$, $Het^1$, —O—(C=O)—CH($NH_2$)—$C_{1-4}$alkyl, —O—(C=O)—CH($NH_2$)—$C_{1-4}$alkyl-Ar,

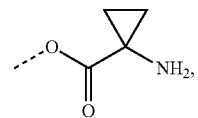

—O—$C_{1-4}$alkyl-OH, and —O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl)$_2$, —$NH_2$, —NH($C_{1-4}$alkyl) and —N($C_{1-4}$alkyl)$_2$;

$R^{5c}$ represents hydrogen or $C_{1-4}$alkyl;

$R^{5d}$ and $R^{5e}$ each independently are selected from the group consisting of hydrogen and $C_{1-4}$alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl)$_2$;

Ring

represents a 6-membered aromatic ring containing 1 or 2 N-atoms;

$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —$NH(C_{1-4}alkyl)$, and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —$NH(C_{1-4}alkyl)$, and hydroxyl;

$Het^1$ represents a monocyclic 4-, 5-, 6- or 7-membered saturated or partially saturated heterocyclyl containing at least one heteroatom each independently selected from O, S, S(=O)$_p$ and N; or $Het^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —$NR^{9a}R^{9b}$, $C_{1-4}$alkyl, —(C=O)—$OR^{5h}$, —S(=O)$_2$—$C_{1-6}$alkyl, —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —$NH(C_{1-4}alkyl)$ and —$N(C_{1-4}alkyl)_2$; or two substituents on the same carbon atom of said heterocyclyl are taken together to form together with the common carbon atom to which they are attached Ring B;

$R^{9a}$ and $R^{9b}$ each independently are selected from the group consisting of hydrogen, $C_{1-4}$alkyl, and $C_{1-4}$alkyl substituted with one or more halo atoms;

$Het^2$ represents

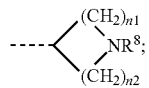

n1 represents 1 or 2;
n2 represents 1 or 2;
Re represents hydrogen, $C_{1-4}$alkyl, or $C_{1-4}$alkyl substituted with one or more halo atoms;
$R^{5h}$ represents hydrogen or $C_{1-4}$alkyl;
Ring B represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

p represents 1 or 2;
Ar represents phenyl optionally substituted with one hydroxyl;
$R^7$ represents

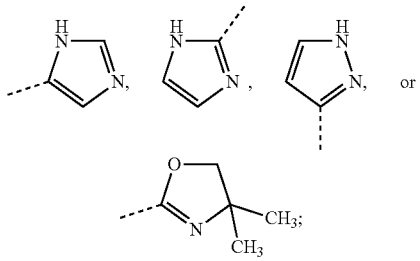

and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit PI3Kβ per se or can undergo metabolism to a (more) active form in vivo (prodrugs), and therefore may be useful in the treatment or prevention, in particular in the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof, may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of PI3Kβ, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

The prefix "$C_{x-y}$" (where x and y are integers) as used herein refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms, a $C_{3-6}$cycloalkyl group contains from 3 to 6 carbon atoms, and so on.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{3-6}$cycloalkyl" alone or in combination, refers to a cyclic saturated hydrocarbon radical having from 3 to 6 carbon atoms. Non-limiting examples of suitable $C_{3-6}$cycloalkyl include cyclopropyl, cyclobutyl, cyclopentyl and cyclohexyl.

Examples of compounds wherein $R^{1b}$ and $R^{1a}$ are taken together to form —(CH$_2$)$_3$— are compounds 1-5, 8-23, 36-52.

In case L represents —CH($C_{1-4}$alkyl)-CH$_2$—, it is intended that the C-atom with the two hydrogens (—CH$_2$—) is attached to the phenyl ring in the structure of formula (I).

In case L represents —CH$_2$—CH($C_{1-4}$alkyl)-, it is intended that the C-atom with the $C_{1-4}$alkyl substituent (—CH($C_{1-4}$alkyl)-) is attached to the phenyl ring in the structure of formula (I).

In case L represents —CHR$^{1a}$—X—, it is intended that 'X' is attached to the phenyl ring in the structure of formula (I).

In case L represents —X—CHR$^{1c}$—, it is intended that the C-atom with the R$^{1c}$ substituent (—CHR$^{1c}$—) is attached to the phenyl ring in the structure of formula (I).

In an embodiment the expression 'at least one heteroatom' is restricted to '1, 2 or 3 heteroatoms', in a particular embodiment to '1 or 2 heteroatoms', in a more particular embodiment to '1 heteroatom'.

Examples of a 4-, 5- or 6-membered saturated heterocyclyl containing at least one heteroatom each independently selected from O, S, S(=O)$_p$ and N (e.g. in Ring B), include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, and the like.

Examples of a 4-, 5-, 6- or 7-membered saturated or partially saturated heterocyclyl containing at least one heteroatom each independently selected from O, S, S(=O)$_p$ and N (e.g. in Het$^1$), include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, 4,5-dihydro-1,3-oxazolyl, hexahydro-1H-1,4-diazepinyl, and the like.

Examples of a bicyclic 8-, 9- or 10-membered saturated or partially saturated heterocyclyl containing at least one heteroatom each independently selected from O, S, S(=O)$_p$ and N (e.g. in Het$^1$), include, but are not limited to 4,5,6,7-tetrahydropyrazolo[1,5-a]pyrazinyl, octahydro-pyrrolo[1,2-a]pyrazinyl, and the like.

Het$^1$ representing a bicyclic heterocyclyl, in particular is a fused bicyclic heterocyclyl.

Het$^1$ may be attached to the remainder of the molecule of Formula (I) through any available ring carbon atom or ring heteroatom as appropriate, if not otherwise specified. In a particular embodiment Het$^1$ is attached to the remainder of the molecule of Formula (I) via a nitrogen atom.

It will be clear that when two substituents on the same carbon atom in the Het$^1$ definition are taken together to form together with the common carbon atom to which they are attached Ring B, a spiro moiety is formed. For example, when Het$^1$ represents 1-piperidinyl wherein two substituents on the carbon atom in position 3 are taken together to form together with the common carbon atom to which they are attached ring B, the following spiro moiety is formed:

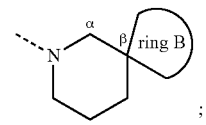

in particular if in the above example ring B represents 3-azetidinyl, the following spiro moiety is formed:

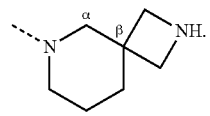

Examples of such spiro moieties, include, but are not limited to

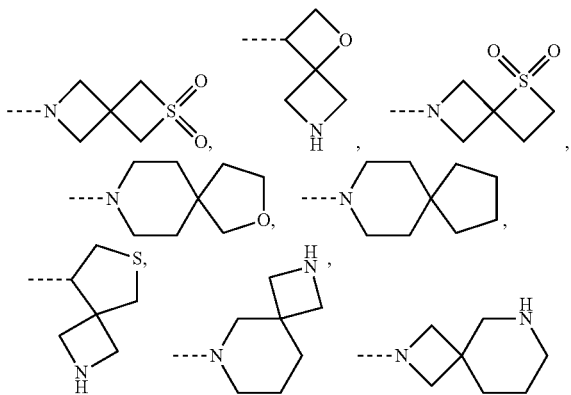

and the like.

Examples of ring

are pyridinyl or pyrimidinyl.

Whenever substituents are represented by chemical structure, "---" represents the bond of attachment to the remainder of the molecule of Formula (I).

Whenever one of the ring systems, is substituted with one or more substituents, those substituents may replace, unless otherwise is indicated or is clear from the context, any hydrogen atom bound to a carbon or nitrogen atom of the ring system.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system.

The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention. It follows that a single compound may exist in both stereoisomeric and tautomeric form. For example, it will be clear for the skilled person that when $R^7$ represents

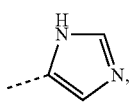

also

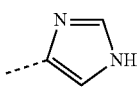

is included.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H.

In particular, deuterated compounds are intended to be included within the scope of the present invention.

In an embodiment, the present invention concerns novel compounds of Formula (I), tautomers and stereoisomeric forms thereof, wherein Y represents $CR^3$;

L represents —CH($C_{1-4}$alkyl)-CH$_2$—, —CH$_2$—CH($C_{1-4}$alkyl)-, —CH($C_{1-4}$alkyl)-CH($C_{1-4}$alkyl)-, —CHR$^{1a}$—X—, or —X—CHR$^{1c}$—;

X represents O, S, or NR$^{1b}$;

R$^{1a}$ represents $C_{1-4}$alkyl;

R$^{1c}$ represents hydrogen or $C_{1-4}$alkyl;

R$^{1b}$ represents hydrogen, $C_{1-4}$alkyl, —CH$_2$—C(=O)—NR$^{6a}$R$^{6b}$, or $C_{1-4}$alkyl substituted with one substituent selected from the group consisting of hydroxyl, —O—$C_{1-4}$alkyl, and —NR$^{6c}$R$^{6d}$;

or R$^{1b}$ is taken together with R$^{1a}$ or R$^{1c}$ to form —(CH$_2$)$_3$—;

or R$^{1b}$ is taken together with R$^{1c}$ to form —(CH$_2$)$_2$— or —(CH$_2$)$_4$—;

R$^2$ represents

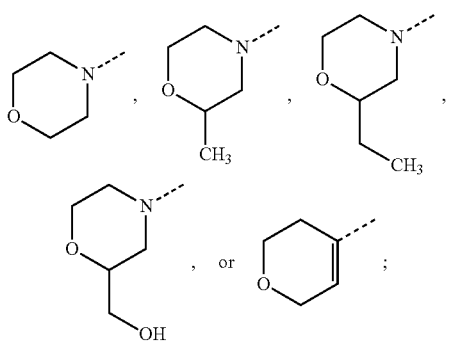

R$^{6a}$ and R$^{6b}$ each independently are selected from the group consisting of hydrogen and $C_{1-4}$alkyl;

R$^{6c}$ and R$^{6d}$ each independently are selected from the group consisting of hydrogen, $C_{1-4}$alkyl, and $C_{1-4}$alkyl substituted with one substituent selected from the group consisting of hydroxyl, —NH$_2$, —NH(C$_{1-4}$alkyl), and —N(C$_{1-4}$alkyl)$_2$;

R$^3$ represents —(C═O)H, —(C═O)—C$_{1-4}$alkyl, —(C═O)—NR$^{5a}$R$^{5b}$, —(C═O)—OR$^{5c}$, —C(═O)—Het$^1$, or —C(═O)—NH—Het$^2$;

R$^{5a}$ and R$^{5b}$ each independently are selected from the group consisting of hydrogen, C$_{1-4}$alkyl, —O—C$_{1-4}$alkyl, —S(═O)$_2$—NH$_2$, —S(═O)$_2$—C$_{1-4}$alkyl, —S(═O)$_2$—C$_{3-6}$cycloalkyl, C$_{1-4}$alkyl substituted with one or more halo atoms, and C$_{1-4}$alkyl substituted with one substituent selected from the group consisting of hydroxyl, —O—C$_{1-4}$alkyl, —S(═O)$_2$—C$_{1-4}$alkyl, —O—C$_{1-4}$alkyl-NH$_2$, —O—C$_{1-4}$alkyl-NH(C$_{1-4}$alkyl), —O—C$_{1-4}$alkyl-N(C$_{1-4}$alkyl)$_2$, —NH$_2$, —NH(C$_{1-4}$alkyl) and —N(C$_{1-4}$alkyl)$_2$;

R$^{5c}$ represents hydrogen or C$_{1-4}$alkyl;

Ring

represents a 6-membered aromatic ring containing 1 or 2 N-atoms;

R$^{4a}$, R$^{4b}$ and R$^{4c}$ each independently are selected from the group consisting of hydrogen, cyano, C$_{1-4}$alkyl, halo, —C(═O)H, —NR$^{6e}$R$^{6f}$, —O—C$_{1-4}$alkyl, and C$_{1-4}$alkyl substituted with one or more substituents each independently selected from the group consisting of hydroxyl, halo, and —NR$^{6a}$R$^{6b}$;

R$^{6e}$ and R$^{6f}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

R$^{6g}$ and R$^{6h}$ each independently are selected from the group consisting of hydrogen, C$_{1-4}$-alkyl, and C$_{1-4}$alkyl substituted with one substituent selected from the group consisting of —NH$_2$, —NH(C$_{1-4}$alkyl), and hydroxyl;

Het$^1$ represents a monocyclic 4-, 5-, 6- or 7-membered saturated or partially saturated heterocyclyl containing at least one heteroatom each independently selected from O, S, S(═O)$_p$ and N; or Het$^1$ represents a bicyclic 8-, 9- or 10-membered saturated or partially saturated heterocyclyl containing at least one heteroatom each independently selected from O, S, S(═O)$_p$ and N;

each optionally substituted with one or two substituents each independently selected from the group consisting of halo, —NR$^{9a}$R$^{9b}$, C$_{1-4}$alkyl, —(C═O)—OR$^{5h}$, —S(═O)$_2$—C$_{1-6}$alkyl, —C$_{1-4}$alkyl-S(═O)$_2$—C$_{1-4}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring B;

R$^{9a}$ and R$^{9b}$ each independently are selected from the group consisting of hydrogen, C$_{1-4}$alkyl, and C$_{1-4}$alkyl substituted with one or more halo atoms;

Het$^2$ represents

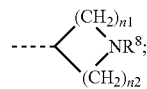

n1 represents 1 or 2;
n2 represents 1 or 2;
R$^8$ represents hydrogen, C$_{1-4}$alkyl, or C$_{1-4}$alkyl substituted with one or more halo atoms;
R$^{5h}$ represents hydrogen or C$_{1-4}$alkyl;
Ring B represents cyclobutyl, cyclopentyl, cyclohexyl, or a 4-, 5- or 6-membered saturated heterocyclyl containing at least one heteroatom each independently selected from O, S, S(═O)$_p$ and N; said cyclobutyl, cyclopentyl, cyclohexyl, or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;
p represents 1 or 2;
and the N-oxides, the pharmaceutically acceptable addition salts, and the solvates thereof.

In an embodiment, the present invention concerns novel compounds of Formula (I), tautomers and stereoisomeric forms thereof, wherein
Y represents CR$^3$;
L represents —CHR$^{1a}$—X—, or —X—CHR$^{1c}$—;
X represents NR$^{1b}$;
R$^{1a}$ represents C$_{1-4}$alkyl;
R$^{1c}$ represents hydrogen;
R$^{1b}$ represents hydrogen;
or R$^{1b}$ is taken together with R$^{1a}$ or R$^{1c}$ to form —(CH$_2$)$_3$—;
R$^2$ represents

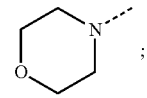

R$^3$ represents —(C═O)—NR$^{5a}$R$^{5b}$, —(C═O)—OR$^{5c}$, or —C(═O)—Het$^1$;
R$^{5a}$ and R$^{5b}$ each independently are selected from the group consisting of hydrogen, C$_{1-4}$alkyl, and
C$_{1-4}$alkyl substituted with one substituent selected from the group consisting of hydroxyl, —O—C$_{1-4}$alkyl-NH(C$_{1-4}$alkyl), —NH(C$_{1-4}$alkyl) and —N(C$_{1-4}$alkyl)$_2$;
R$^{5c}$ represents hydrogen or C$_{1-4}$alkyl;
Ring

represents a 6-membered aromatic ring containing 1 or 2 N-atoms;
R$^{4a}$, R$^{4b}$ and R$^{4c}$ each independently are selected from the group consisting of hydrogen, C$_{1-4}$alkyl, halo, —O—C$_{1-4}$alkyl, and C$_{1-4}$alkyl substituted with one or more halo substituents;
Het$^1$ represents a monocyclic 4-membered saturated heterocyclyl containing at least one N-atom; wherein two substituents on the same carbon atom of said heterocyclyl are taken together to form together with the common carbon atom to which they are attached Ring B;

Ring B represents 4-membered saturated heterocyclyl containing at least one $S(=O)_p$;

p represents 2;

and the N-oxides, the pharmaceutically acceptable addition salts, and the solvates thereof.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) Y represents $CR^3$;
(ii) L represents —$CHR^{1a}$—X—, or —X—$CHR^{1c}$—;
(iii) X represents $NR^{1b}$;
$R^{1a}$ represents $C_{1-4}$alkyl;
$R^{1c}$ represents hydrogen;
$R^{1b}$ represents hydrogen;
or $R^{1b}$ is taken together with $R^{1a}$ or $R^{1c}$ to form —$(CH_2)_3$—;
(iv) $R^2$ represents

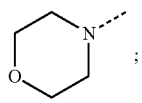
;

(v) $R^3$ represents —(C=O)—$NR^{5a}R^{5b}$, —(C=O)—$OR^{5c}$, or —C(=O)—$Het^1$;
(vi) $R^{5a}$ and $R^{5b}$ each independently are selected from the group consisting of hydrogen, $C_{1-4}$alkyl, and $C_{1-4}$alkyl substituted with one substituent selected from the group consisting of hydroxyl, —O—$C_{1-4}$alkyl-$NH(C_{1-4}$alkyl), —$NH(C_{1-4}$alkyl) and —$N(C_{1-4}$alkyl)$_2$;
(vii) $R^{5c}$ represents hydrogen or $C_{1-4}$alkyl;
(viii) Ring

represents a 6-membered aromatic ring containing 1 or 2 N-atoms;
(ix) $R^{4a}$, $R^{4b}$ and $R^{4c}$ each independently are selected from the group consisting of hydrogen, $C_{1-4}$alkyl, halo, —O—$C_{1-4}$alkyl, and $C_{1-4}$alkyl substituted with one or more halo substituents;
(x) $Het^1$ represents a monocyclic 4-membered saturated heterocyclyl containing at least one N-atom; wherein two substituents on the same carbon atom of said heterocyclyl are taken together to form together with the common carbon atom to which they are attached Ring B;
(xi) Ring B represents 4-membered saturated heterocyclyl containing at least one $S(=O)_p$;
(xii) p represents 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein L represents —$CH(CH_3)$—NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein L represents

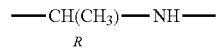

(R stereochemistry).

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents $CR^3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents N.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ as defined in any of the other embodiments is attached to the remainder of the molecule via a N-atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents

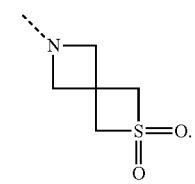

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^2$ represents

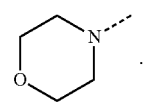
.

In an embodiment, the present invention relates to those compounds of Formula (I) and the N-oxides, the pharmaceutically acceptable addition salts, and the solvates thereof, or any subgroup thereof as mentioned in any of the other embodiments, wherein R² represents

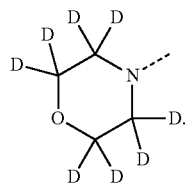

In an embodiment, the present invention relates to those compounds of Formula (I) and the N-oxides, the pharmaceutically acceptable addition salts, and the solvates thereof, or any subgroup thereof as mentioned in any of the other embodiments, wherein
L represents —CHR$^{1a}$—X—;
X represents NR$^{1b}$;
R$^{1b}$ is taken together with R$^{1a}$ to form —(CH$_2$)$_3$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents R⁷, —(C=O)H, —(C=O)—C$_{1-4}$alkyl, —(C=O)—NR$^{5a}$R$^{5b}$, —C(=O)—Het¹, —C(=O)—NH—Het², C$_{1-4}$alkyl, —CH=N—OH, —CH(OH)—CH$_2$—NR$^{5d}$R$^{5e}$, —CH(OH)—CH$_2$-Het¹, —CH(OH)—C$_{1-4}$alkyl, —C(OH)(C$_{1-4}$alkyl)$_2$, halo, or R³ represents C$_{1-4}$alkyl substituted with one substituent selected from the group consisting of hydroxyl, fluoro, —NR$^{5f}$R$^{5g}$, Het¹, —O—(C=O)—CH(NH$_2$)—C$_{1-4}$alkyl, —O—(C=O)—CH(NH$_2$)—C$_{1-4}$alkyl-Ar,

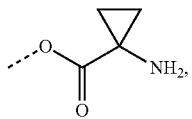

—O—C$_{1-4}$alkyl-OH, and —O—C$_{1-4}$alkyl-NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
R³ represents —(C=O)H, —(C=O)—C$_{1-4}$alkyl, —(C=O)—NR$^{5a}$R$^{5b}$, —(C=O)—OR$^{5c}$, —C(=O)—Het¹, or —C(=O)—NH—Het².

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents —(C=O)—NR$^{5a}$R$^{5b}$ or —C(=O)—Het¹.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents —(C=O)—NR$^{5a}$R$^{5b}$.

In an embodiment, the present invention relates to those compounds of Formula (I) and the N-oxides, the pharmaceutically acceptable addition salts, and the solvates thereof, or any subgroup thereof as mentioned in any of the other embodiments, wherein R³ represents —C(=O)—Het¹.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention. For example, the skilled person will realize that some of the general schemes wherein Y is Y¹ may, dependent on the reaction conditions, also apply for cases wherein Y represents —(C=O)—O—H or C$_{1-4}$alkyl substituted with OH.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. Conventional protecting groups can be used in accordance with standard practice. The protecting groups may be removed at a convenient subsequent stage using methods known from the art. This is illustrated in the specific examples. For example, a skilled person will realize that e.g. preparation of compound 48 according to Scheme 7 requires cleavage of the tert-butoxycarbonyl (Boc) in acidic media such as for example 3M hydrochloric acid in cyclopentylmethylether at 50° C. For example, preparation of compound 28 according to scheme 5 is obtained after cleavage of the tert-butyldimethylsilyl in the presence of tetrabutylammonium Fluoride (1M in tetrahydrofuran) in tetrahydrofuran at room temperature.

The skilled person will realize that in the reactions described in the Schemes, it may be advisable or necessary to perform the reaction under an inert atmosphere, such as for example under N2-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

In general, compounds of formula (I) wherein L is defined as shown in scheme 1 and Y is Y¹ being N or CR³ wherein R³ is defined as —C$_{1-4}$alkyl, —(C=O)—O—C$_{1-4}$alkyl, —(C=O)—NR$^{5a}$R$^{5b}$, —C(=O)—Het¹ or halo, said compounds being represented by formula (Ia) can be prepared according to the following reaction Scheme 1 wherein PG¹ is a protecting group such as for example a tert-Butyloxycarbonyl (Boc) and halo² is defined as Cl, Br or I. All other variables in Scheme 1 are defined according to the scope of the present invention.

Scheme 1

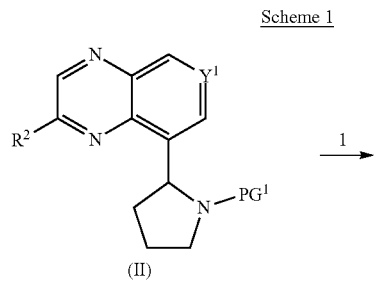

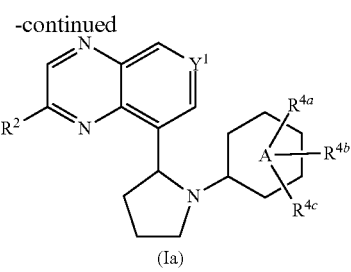

In Scheme 1, the following reaction conditions apply:

1: in the presence of a suitable acid such as for example hydrochloric acid (HCl) or trifluoroacetic acid (TFA), a suitable solvent such as for example dichloromethane (DCM), at a suitable temperature such as room temperature;

2: in the presence of a suitable catalyst such as for example palladium acetate (Pd(OAc)₂) or tris(dibenzylideneacetone)dipalladium(0) (Pd₂(dba)₃), a suitable ligand such as for example Xanthphos or 2-(di-tert-butylphosphino)biphenyl a suitable base such as for example cesium carbonate or sodium tert-butoxide, a suitable solvent such as for example 1,4-dioxane, at a suitable temperature such as 100° C., in a sealed vessel.

In general, compounds of formula (I) wherein L is defined as shown in scheme 2 and Y is $Y^1$ being N or $CR^3$ wherein $R^3$ is defined as —$C_{1-4}$alkyl, —(C=O)—O—$C_{1-4}$alkyl, —(C=O)—$NR^{5a}R^{5b}$, —C(=O)—$Het^1$ or halo, and $R^{1a}$ is defined as $C_{1-4}$alkyl, said compounds being represented by formula (Ib) and (Ic) can be prepared according to the following reaction Scheme 2 wherein halo¹ is defined as Cl, Br and I, and halo³ is defined as Cl or Br. 'n-Bu' means n-butyl. All other variables in Scheme 2 are defined according to the scope of the present invention, or as defined before.

Scheme 2

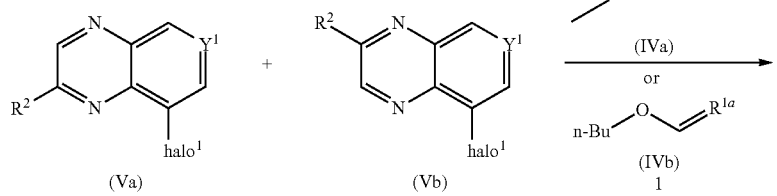

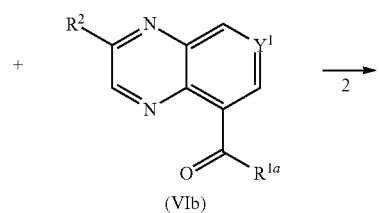

-continued

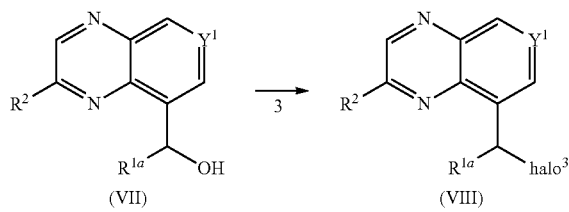
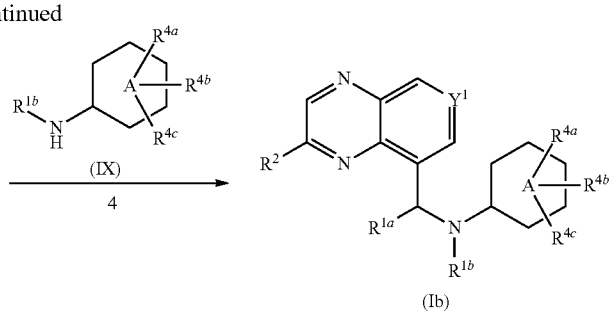
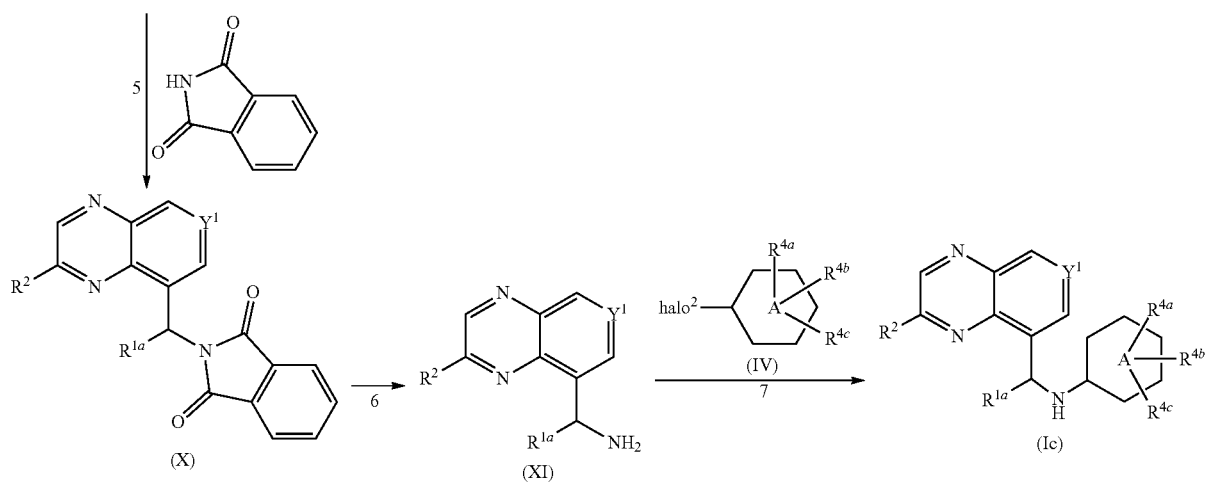

In Scheme 2, the following reaction conditions apply:

1: In case of reagent (IVa), in the presence of a suitable catalyst such as for example dichlorobis(triphenylphosphine) palladium (II) or tetrakis(triphenylphosphine)-palladium(0) (Pd(Ph$_3$)$_4$), a suitable solvent such as for example 1,4-dioxane, at a suitable temperature such as 100° C. in a sealed or an open vessel; Then, in the presence of a suitable acid such as for example aqueous HCl, at a suitable temperature such as room temperature;

In case of reagent (IVb), in the presence of a suitable catalyst such as for example Pd(OAc)$_2$, a suitable ligand such as for example 1,3-Bis(diphenylphosphino)propane (DPPP), a suitable base such as for example triethylamine, a suitable solvent such as for example dimethylsulfoxide, at a suitable temperature such as 100° C.; Then, in the presence of a suitable acid such as for example HCl, at a suitable temperature such as 0° C.;

2: in the presence of a suitable reducing reagent such as for example sodium borohydride, a suitable solvent such as for example a mixture of methanol and dichloromethane, at a suitable temperature such as room temperature, in the presence or not of a suitable additive such as for example cerium (III) chloride;

3: in the presence of a suitable halogenating reagent such as for example phosphorous tribromide or thionyl chloride, a suitable solvent such as for example dichloromethane, at a suitable temperature such as for example 10° C. or room temperature;

4: in the presence of a suitable solvent such as for example N,N-dimethyformamide, at a suitable temperature such as for example 50 or 60° C., in a sealed vessel;

5: in the presence of a suitable reagent such as for example di-tert-butyl azodicarboxylate, a suitable phosphine such as for example triphenylphosphine, a suitable solvent such as for example tetrahydrofuran, at a suitable temperature such as for example room temperature;

6: in the presence of a suitable reagent such as for example hydrazine monohydrate, a suitable solvent such as for example ethanol, at a suitable temperature such as for example 80° C.;

7: in the presence of a suitable catalyst such as for example chloro[2-(dicyclo-hexylphosphino)-3,6-dimethoxy-2',4',6'-triisopropyl-1,1'-biphenyl][2-(2-aminoethyl)-phenyl]palladium(II) (Brettphos precatalyst first gen), a suitable base such as for example cesium carbonate, a suitable solvent such as for example 2-methyl-2-butanol, at a suitable temperature such as 100° C., in a sealed vessel.

In general, compounds of formula (I) wherein L is defined as shown in scheme 3;

Y is Y$^1$ being N or CR$^3$ wherein R$^3$ is defined as —C$_{1-4}$alkyl, —(C=O)—O—C$_{1-4}$alkyl, —(C=O)—NR$^{5a}$R$^{5b}$, —C(=O)—Het$^1$ or halo;

R$^{1a}$ is defined as C$_{1-4}$alkyl or hydrogen for step 1 and 2, and is defined according to the scope of the present invention for step 3);

said compounds being represented by formula (Id) can be prepared according to the following reaction Scheme 3 wherein halo$^1$ is defined as Cl, Br or I and halo$^3$ is defined as Cl or Br. All other variables in Scheme 3 are defined according to the scope of the present invention.

Scheme 3

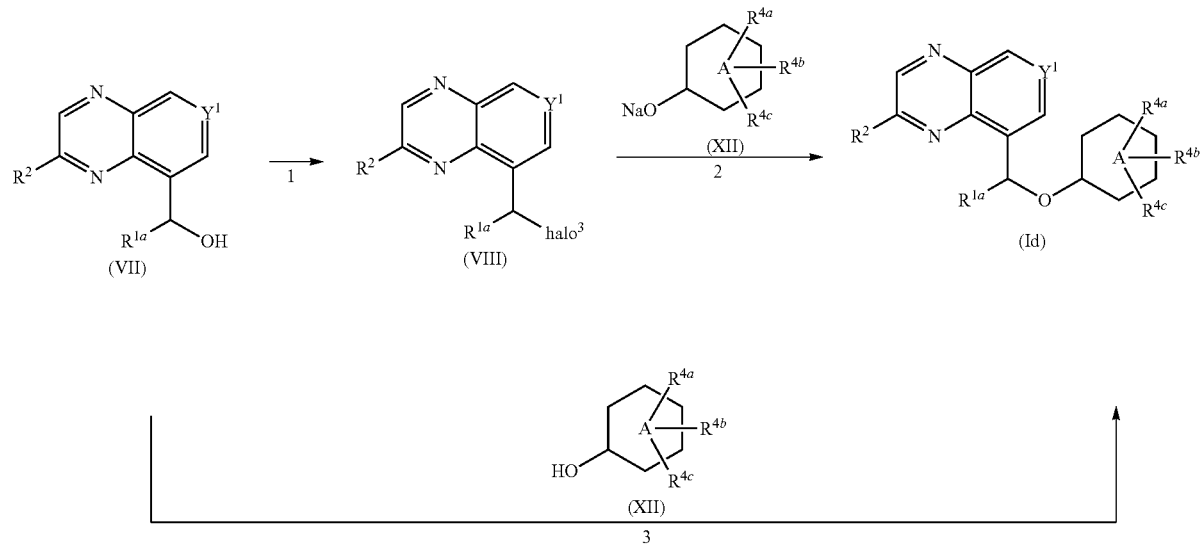

In Scheme 3, the following reaction conditions apply:

1: in the presence of a suitable halogenating reagent such as for example phosphorous tribromide or thionyl chloride, a suitable solvent such as for example dichloromethane, at a suitable temperature such as for example 10° C. or room temperature;

2: in the presence of a suitable solvent such as for example N,N-dimethylformamide, at a suitable temperature such as for example 50 or 60° C., in a sealed vessel;

3: in the presence of a suitable reagent such as for example di-tert-butylazodicarboxylate, a suitable phosphine such as for example triphenylphosphine, a solvent such as for example tetrahydrofuran, at a suitable temperature such as for example room temperature;

Alternatively, in the presence of a suitable reagent such as for example cyanoethylenetributylphosphorane, a solvent such as for example toluene, at a suitable temperature such as for example 60° C., in a sealed vessel.

In general, compounds of formula (I) wherein L is defined as shown in scheme 4;

Y is $Y^1$ being N or $CR^3$ wherein $R^3$ is defined as —$C_{1-4}$alkyl, —(C=O)—O—$C_{1-4}$alkyl, —(C=O)—$NR^{5a}R^{5b}$, —C(=O)—$Het^1$ or halo;

$R^{1a}$ is defined as $C_{1-4}$alkyl or hydrogen;

said compounds being represented by formula (Ie), can be prepared according to the following reaction Scheme 4 wherein $halo^3$ is defined as Cl or Br. All other variables in Scheme 4 are defined according to the scope of the present invention.

Scheme 4

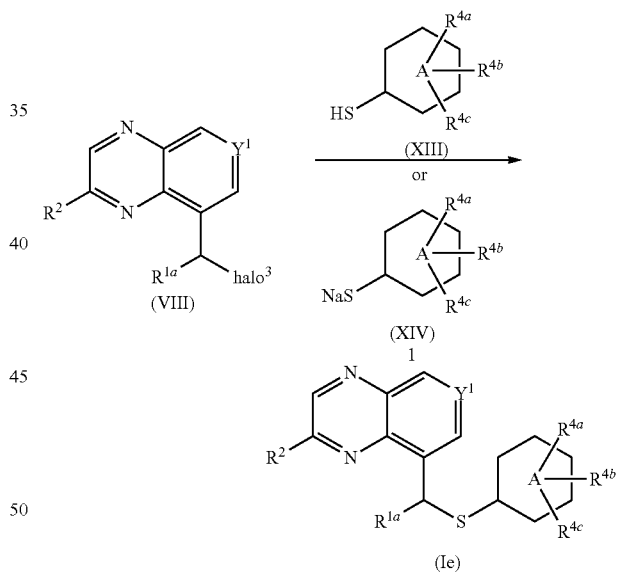

In Scheme 4, the following reaction conditions apply:

1: in the presence of a suitable solvent such as for example N,N-dimethylformamide, at a suitable temperature such as for example 50 or 60° C., in a sealed vessel.

In general, compounds of formula (I) wherein L is defined as shown in scheme 5 and Y is $Y^1$ being N or $CR^3$ wherein $R^3$ is defined as —$C_{1-4}$alkyl, —(C=O)—O—$C_{1-4}$alkyl, —(C=O)—$NR^{5a}R^{5b}$, —C(=O)—$Het^1$ or halo, said compounds being represented by formula (If) can be prepared according to the following reaction Scheme 5 wherein $halo^1$ is defined as Cl, Br or I, $W^1$ is a leaving group such as for example Cl, Br or I, and n is 0, 1 or 2. Moreover $R^{5a}$ and $R^{5b}$ are other than hydrogen for the purpose of Scheme 5. All other variables in Scheme 5 are defined according to the scope of the present invention.

Scheme 5

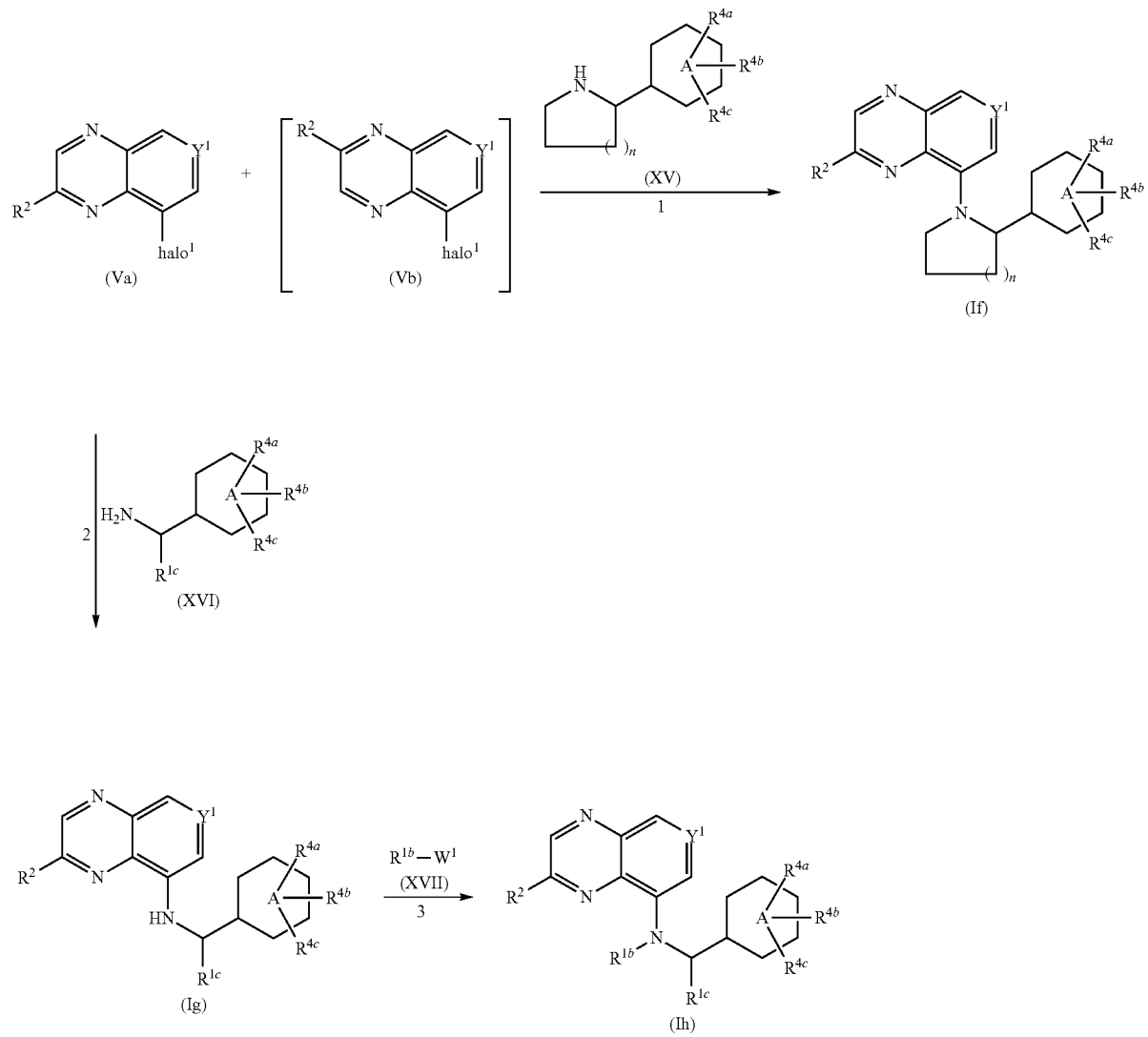

In Scheme 5, the following reaction conditions apply:

1: in the presence of a suitable catalyst such as for example chloro[2-(dicyclohexylphosphino)-3,6-dimethoxy-2',4',6'-triisopropyl-1,1'-biphenyl][2-(2-aminoethyl)phenyl]palladium(II) (Brettphos precatalyst first gen), with or without a suitable ligand such as for example 2-dicyclohexylphosphino-2,6'-diisopropoxy-1,1'-biphenyl, a suitable base such as for example cesium carbonate, a suitable solvent such as for example tert-amyl alcohol (2-methyl-2-butanol) or toluene, at a suitable temperature such as 100° C., in a sealed vessel;

2: in the presence of a suitable catalyst such as for example chloro[2-(dicyclohexylphosphino)-3,6-dimethoxy-2',4',6'-triisopropyl-1,1'-biphenyl][2-(2-aminoethyl)phenyl]palladium(II) (Brettphos precatalyst first gen) or palladium acetate, with or without a suitable ligand such as for example 2-dicyclohexylphosphino-2,6'-diisopropoxy-1,1'-biphenyl or 4,5-Bis(diphenylphosphino)-9,9-dimethylxanthene, a suitable base such as for example cesium carbonate, a suitable solvent such as for example tert-amyl alcohol, toluene or dioxane, at a suitable temperature ranged from 80 to 100° C., in a sealed vessel;

3: in the presence of a suitable deprotonating agent such as for example sodium hydride, a suitable solvent such as for example dimethylformamide, at a suitable temperature such as for example room temperature.

A subgroup of the Intermediates of formula (II) used in the above Scheme 1, hereby named Intermediates of formula (II-1) wherein L is limited according to scheme 6 and Y is $Y^{1a}$ being N, —C—$C_{1-4}$alkyl, —C—(C=O)—O—$C_{1-4}$alkyl and $C_{1-4}$alkyl can be prepared according to the following reaction Scheme 6 wherein $PG^1$ is a protecting group such as for example a Boc, and $halo^1$ is defined as Cl, Br or I. All other variables in Scheme 6 are defined according to the scope of the present invention.

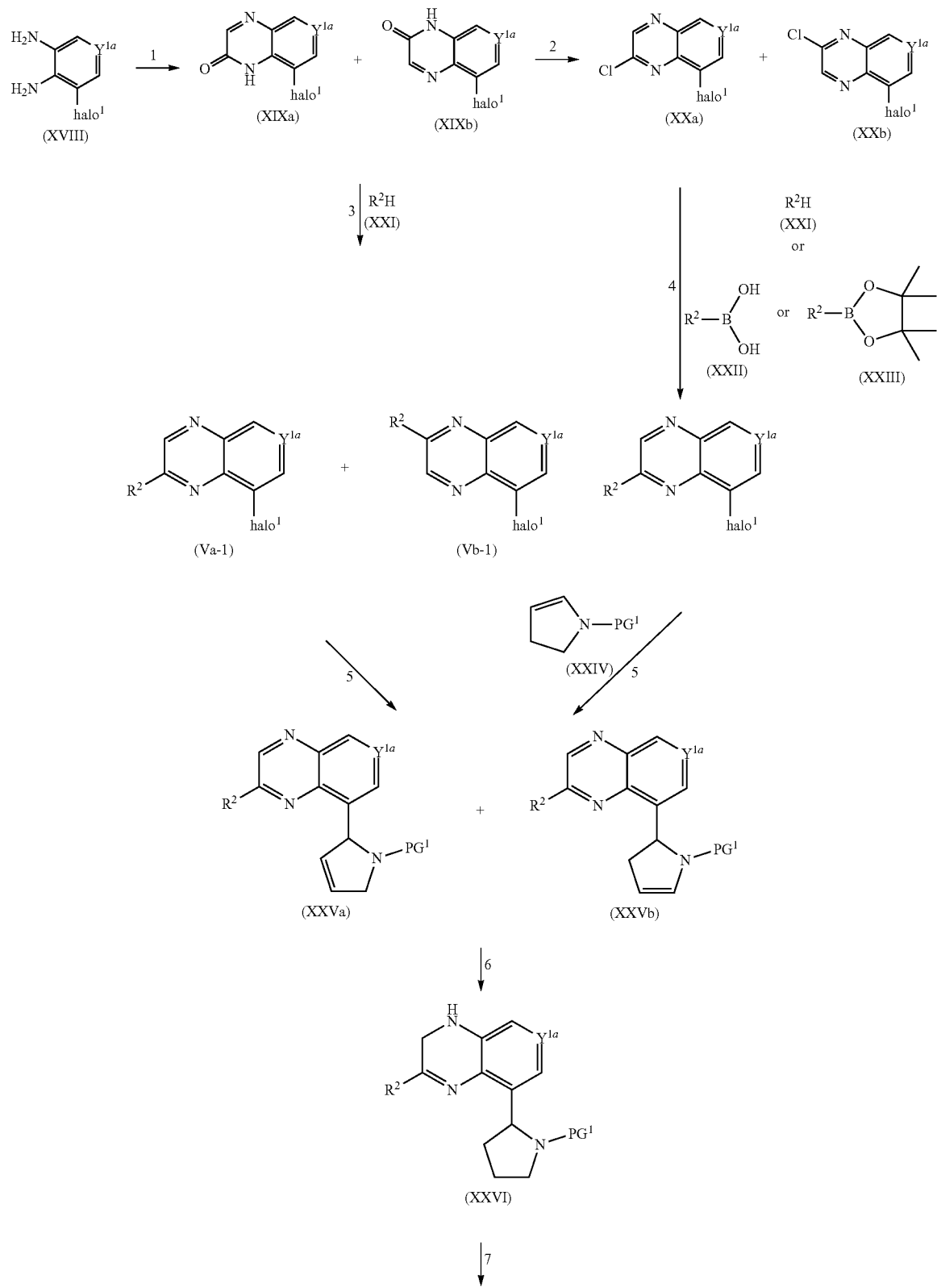

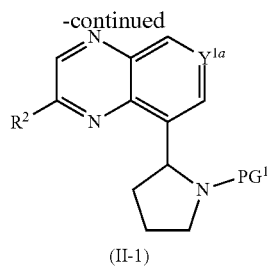

(II-1)

In Scheme 6, the following reaction conditions apply:

1: in the presence of a suitable reagent such as for example 2,2-dihydroxy acetic acid, a suitable solvent such as for example a mixture of water and methanol, at a suitable temperature such as room temperature;

Alternatively, in the presence of a suitable reagent such as for example an ethyl glyoxalate solution in toluene, a suitable solvent such as for example ethanol, at a suitable temperature such as solvent reflux;

2: in the presence of a suitable chlorinating reagent such as for example phosphoryl trichloride ($POCl_3$), at a suitable temperature such as 80° C.;

3: in the presence of a suitable coupling reagent such as for example phosphoryl bromo-tris-pyrrolidino-phosphonium hexafluorophosphate, a suitable base such as for example triethylamine, a suitable solvent such as for example tetrahydrofuran, at a suitable temperature such as room temperature;

4: in case of an intermediate of formula (XXI): in the presence of a suitable solvent such as for example tetrahydrofuran, at a suitable temperature such as solvent reflux;

in case of an intermediate of formula (XXII) or in case of an intermediate of formula (XXIII): in the presence of a suitable catalyst such as for example [1,1'-Bis(diphenylphosphino)ferrocene]dichloropalladium(II), complex with dichloromethane, suitable base such as for example potassium phosphate, a suitable solvent such as for example 1,4-dioxane, at a suitable temperature such as for example 80° C., in a sealed vessel;

5: in the presence of a suitable catalyst such as for example $Pd(OAc)_2$, a suitable phosphine such as for example triphenylphosphine, a suitable base such as for example potassium carbonate, a suitable solvent such as for example N,N-dimethylformamide or 1,4-dioxane, at a suitable temperature such as for example 100° C., in a sealed vessel;

6: in the presence of hydrogen, a suitable catalyst such as for example platinium (IV) oxide, a suitable solvent such as for example methanol, at a suitable temperature such as for example room temperature;

7: in the presence of a suitable oxidative reagent such as for example manganese oxide, a suitable solvent such as for example dichloromethane, at a suitable temperature such as for example room temperature.

In general, compounds of formula (I) wherein L is $L^1$ being —$CHR^{1a}$—X— or —X—$CHR^{1c}$—; and Y is $Y^a$ being $CR^3$ wherein $R^3$ is defined as —COOH, —$CH_2OH$, —(C=O)H, —CH(OH)—$CH_2$—$N^{5d}R^{5e}$, —CH(OH)—$CH_2$-$Het^1$, —(C=O)—$NR^{5a}R^{5b}$, —C(=O)—$Het^1$, —$CH_2$—$NR^{5f}R^{5g}$ or —$CH_2$-$Het^1$, said compounds being represented respectively by compounds of formula (Ii), (Ij), (Ik), (Il), (Im), (Iad), I(ae), I(an) and I(ao), can be prepared according to the following reaction Scheme 7.

All other variables in Scheme 7 are defined according to the scope of the present invention.

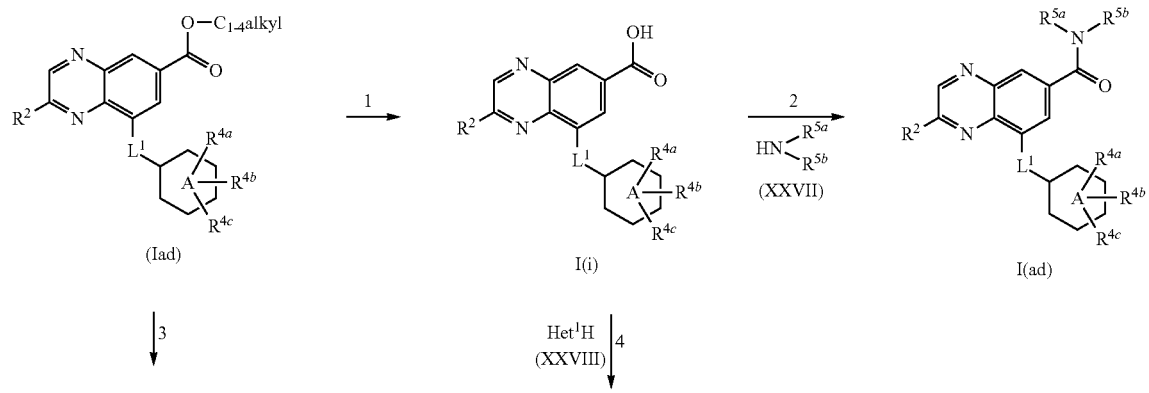

Scheme 7

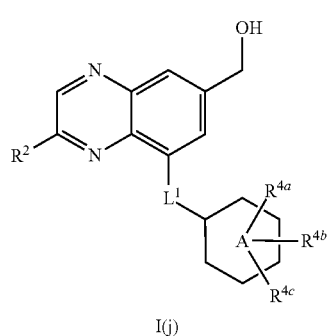

I(j)

-continued

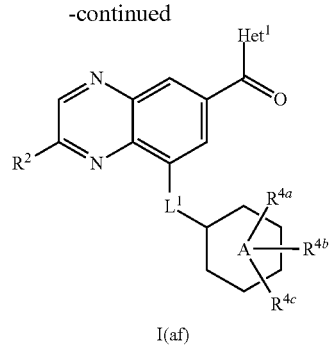

I(af)

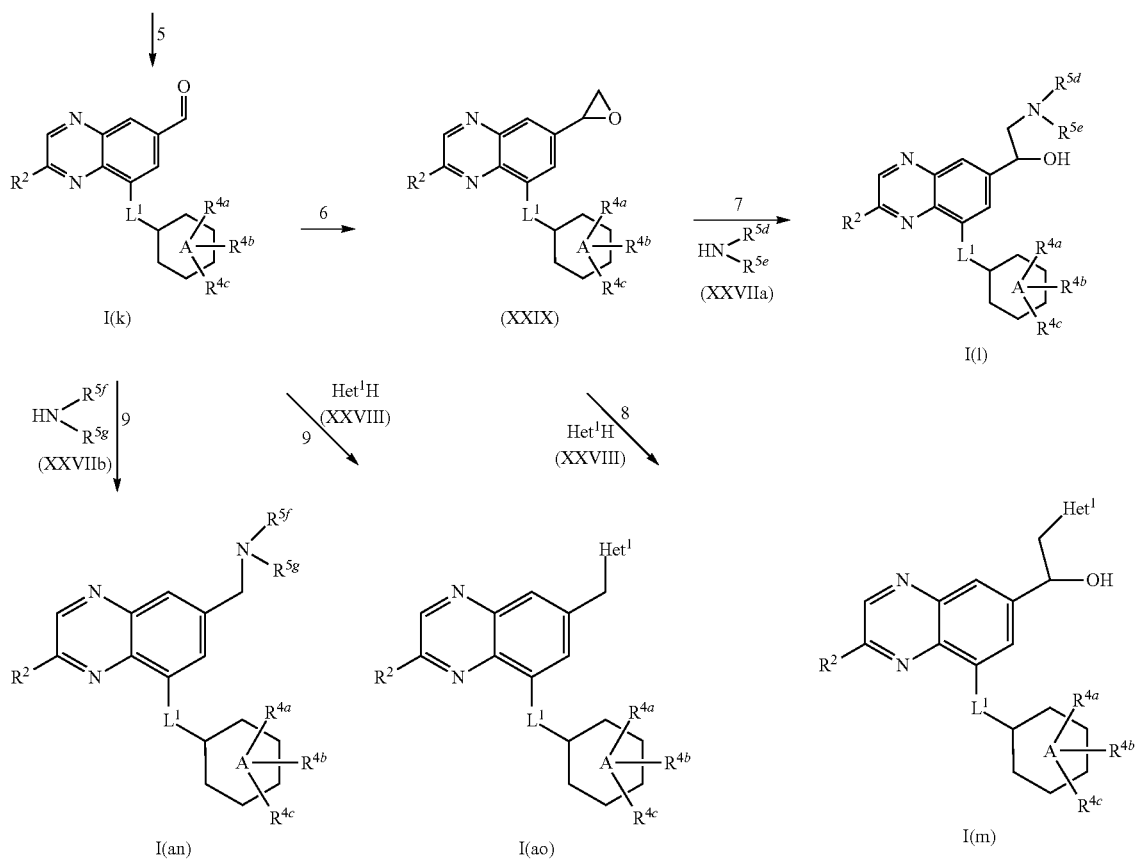

In Scheme 7, the following reaction conditions apply:

1: in the presence of a suitable base such as for example lithium hydroxide, sodium hydroxide or sodium carbonate, a suitable solvent such as for example a mixture of water and tetrahydrofuran or a mixture of water, methanol and tetrahydrofuran, at a suitable temperature such as for example 50° C. or room temperature;

2: in the presence of a suitable coupling reagent such as for example N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate (HBTU), (1-Cyano-2-ethoxy-2-oxoethylidenaminooxy)dimethyl-amino-morpholino-carbenium hexafluorophosphate (COMU), 1-[Bis(dimethylamino)methylene]-1H-1,2,3-triazolo[4,5-b]pyridinium 3-oxid hexafluorophosphate (HATU) or 1,1'-carbonyldiimidazole, a suitable base such as for example diisopropylethylamine, triethylamine or 1,8-diazabicyclo[5.4.0]undec-7-ene, a suitable solvent such as for example N,N-dimethylformamide or methyltetrahydofuran, at a suitable temperature such as for example room temperature;

3: in the presence of a suitable reducing reagent such as for example diisobutylaluminium hydride, a suitable solvent such as for example tetrahydrofuran, at a suitable temperature such as for example −70° C.;

4: in the presence of a suitable coupling reagent such as for example HBTU, COMU, HATU or 1,1'-carbonyldiimidazole, a suitable base such as for example diisopropylethylamine, triethylamine or 1,8-diazabicyclo[5.4.0]undec-7-ene, a suitable solvent such as for example N,N-dimethylformamide or methyltetrahydofuran, at a suitable temperature such as for example room temperature;

5: in the presence of a suitable oxidative reagent such as for example manganese dioxide, a suitable solvent such as for example dichloromethane, at a suitable temperature such as for example room temperature;

6: in the presence of a suitable reagent such as for example trimethylsulfonium iodide, a suitable deprotonating reagent such as for example sodium hydride, a suitable solvent such as for example tetrahydrofuran, at a suitable temperature such as for example 70° C.;

7: in the presence of a suitable solvent such as for example tetrahydrofuran, at a suitable temperature such as for example 100° C., in a sealed vessel;

8: in the presence of a suitable solvent such as for example tetrahydrofuran, at a suitable temperature such as for example 100° C., in a sealed vessel;

9: in the presence of a suitable reducing agent such as for example sodium borohydride, eventually a suitable base such as for example sodium acetate, in a suitable solvent such as for example methanol at a suitable temperature such as room temperature.

In general, compounds of formula (I) wherein L is $L^3$ defined as —CH($C_{1-4}$alkyl)-$CH_2$—, —$CH_2$—CH($C_{1-4}$alkyl)-, or —CH($C_{1-4}$alkyl)-CH($C_{1-4}$alkyl)- and Y is defined as $CR^3$ and $R^3$ is defined as —(C=O)—$NR^{5a}R^{5b}$, said compounds being represented by formula (In), can be prepared according to the following reaction Scheme 8 wherein $halo^1$ is defined as Cl, Br or I. All other variables in Scheme 8 are defined as above or according to the scope of the present invention.

Scheme 8

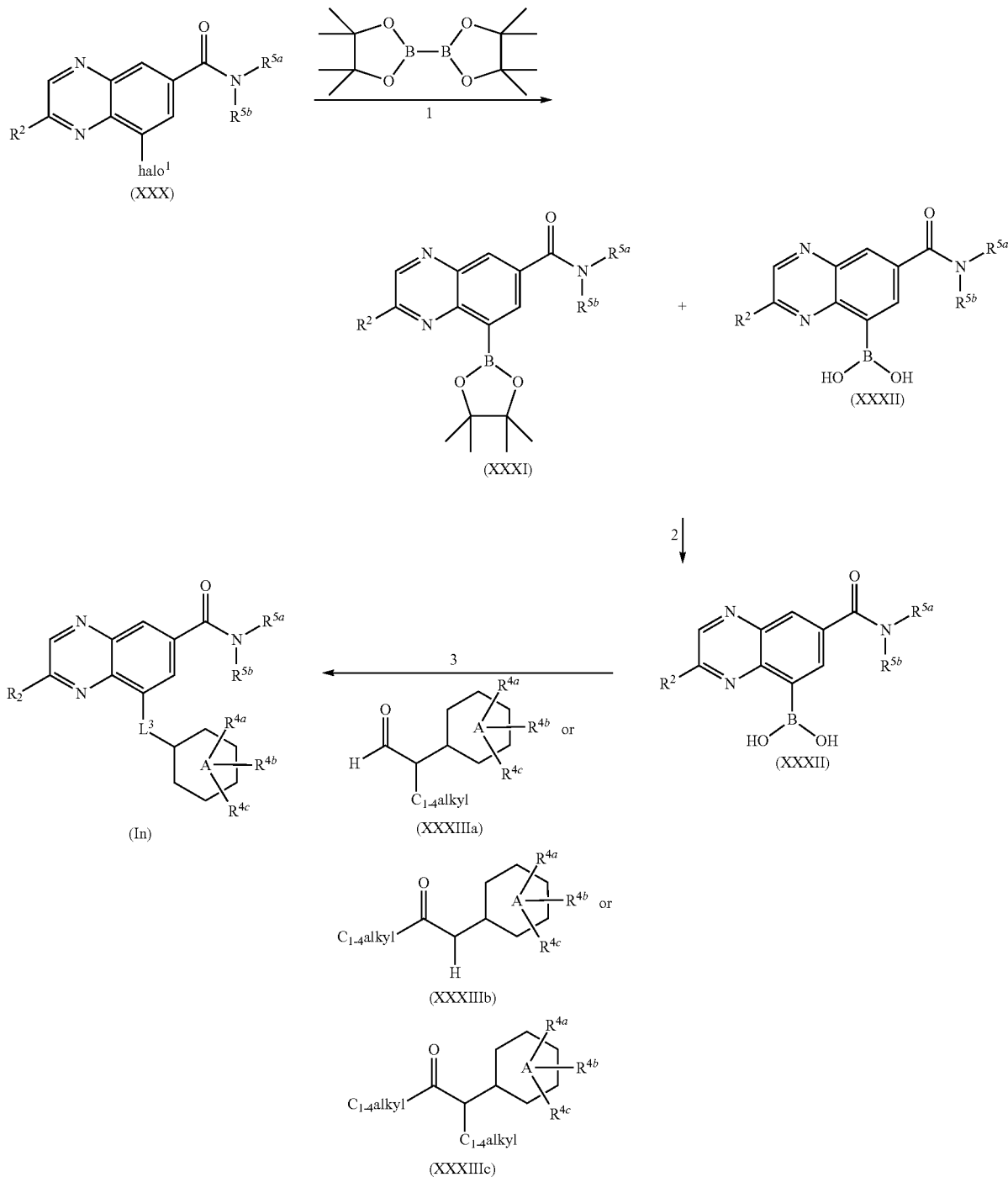

In Scheme 8, the following reaction conditions apply:

1: in the presence of a suitable reagent such as for example Bis(pinacolato)diboron, a suitable catalyst such as for example [1,1'-Bis(diphenylphosphino)ferrocene]-dichloropalladium(II), a suitable base such as for example potassium acetate, a suitable solvent such as for example 1,4-dioxane, at a suitable temperature such as for example 100° C.;

2: in the presence of a suitable reagent such as for example sodium periodate, a suitable acid such as for example hydrochloric acid, a suitable solvent such as for example a mixture of water and tetrahydrofuran, at a suitable temperature such as for example room temperature;

3: in the presence of a suitable reagent such as for example N-tosylhydrazine, a suitable base such as for example potassium carbonate, a suitable solvent such as for example 1,4-dioxane, at a suitable temperature such as for example ranged between 80° C. and 110° C.

In general, compounds of formula (I) wherein L is $L^2$ being —CH($C_{1-4}$alkyl)-$CH_2$—, —$CH_2$—CH($C_{1-4}$alkyl)-, —CH($C_{1-4}$alkyl)-CH($C_{1-4}$alkyl)-, $CHR^{1a}$—X—, or —X—$CHR^{1c}$—; and wherein Y is $Y^2$ being $CR^3$ and $R^3$ is defined as —CH(OH)$C_{1-4}$alkyl or —C(OH)($C_{1-4}$alkyl)$_2$, said compounds being respectively represented by formula (Io) and (Ip), can be prepared according to the following reaction Scheme 9.

For the purpose of Scheme 9, halo$^4$ is defined as Cl or Br; X represents O, S, or $NR^{1b}$;

$R^{1a}$ represents $C_{1-4}$alkyl;

$R^{1b}$ represents $C_{1-4}$alkyl or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—.

All other variables in Scheme 9 are defined according to the scope of the present invention.

Scheme 9

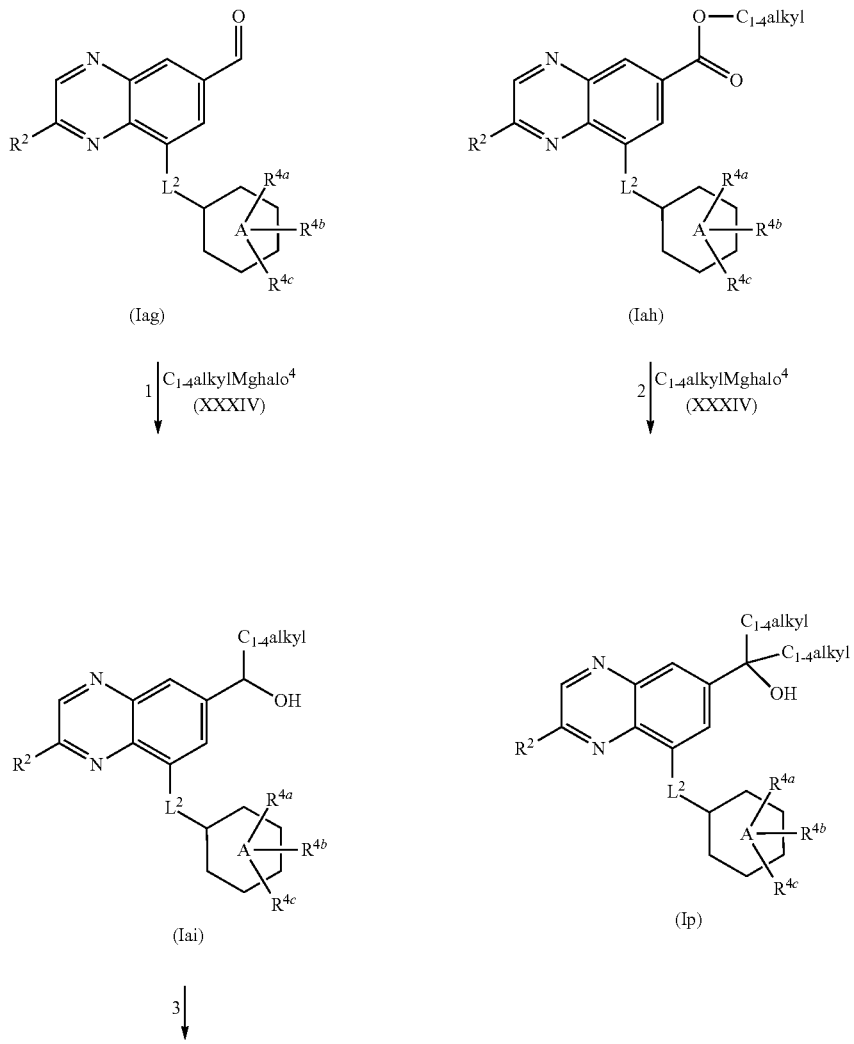

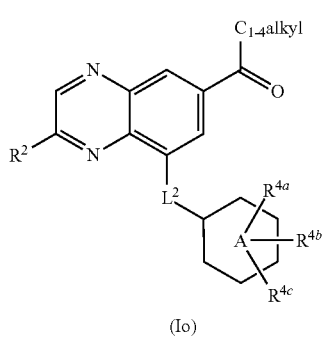

(Io)

In Scheme 9, the following reaction conditions apply:

1: in the presence of a suitable solvent such as for example tetrahydrofuran, at a suitable temperature such as for example 10° C.;

2: in the presence of a suitable solvent such as for example tetrahydrofuran, at a suitable temperature such as for example 10° C.;

3: in the presence of a suitable oxidative reagent such as for example manganese dioxide, a suitable solvent such as for example dichloromethane, at a suitable temperature such as room temperature;

4: in the presence of a suitable solvent such as for example tetrahydrofuran, at a suitable temperature such as for example 10° C.

In general, compounds of formula (I) wherein Y is $Y^3$ being $CR^3$ and $R^3$ is restricted to $R^{7a}$ being defined as

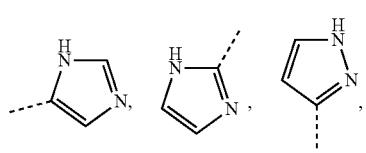

said compounds being represented by formula (Iq), can be prepared according to the following reaction Scheme 10 wherein $halo^5$ is defined as Cl, Br or I. All other variables in Scheme 10 are defined according to the scope of the present invention.

Scheme 10

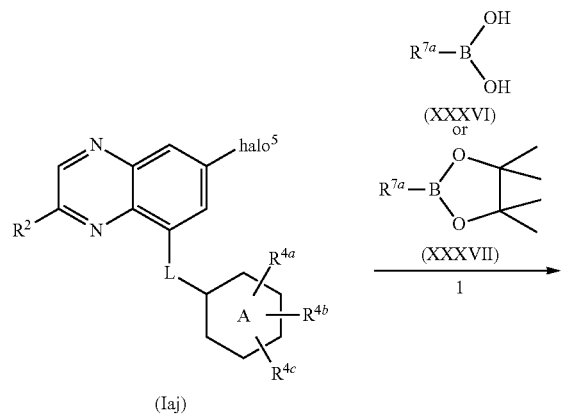

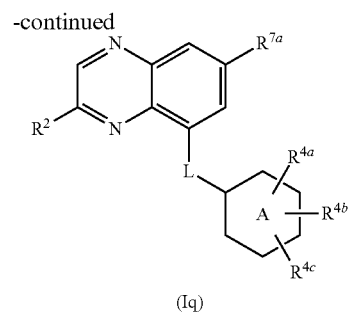

(Iq)

In Scheme 10, the following reaction conditions apply:

1: in the presence of a suitable catalyst such as for example 1,1'-Bis(diphenylphosphino)ferrocene]dichloropalladium(II) complex with dichloromethane, a suitable solvent such as for example tetrahydrofuran, at a suitable temperature such as for example 95° C., and eventually followed by protective groups cleavage using state of the art methods.

In general, compounds of formula (I) wherein Y is $Y^4$ being $CR^3$ and $R^3$ is defined as $CH_2$ substituted with one substituent selected from the group consisting of fluoro, $—NR^{5f}R^{5g}$, $Het^1$, $—O—C_{1-4}alkyl-OH$, and $—O—C_{1-4}alkyl-NH_2$, said compounds being respectively represented by formula (Ir), (Is), (It), (Iu), (Iv) and (Iw) can be prepared according to the following reaction Scheme 11 wherein $halo^6$ is defined as Cl or Br, $W^2$ as a leaving group such as for example Cl or Br and $PG^2$ a protective group such as for example a tert-Butyldimethylsilyl (TBDMS). All other variables in Scheme 11 are defined according to the scope of the present invention.

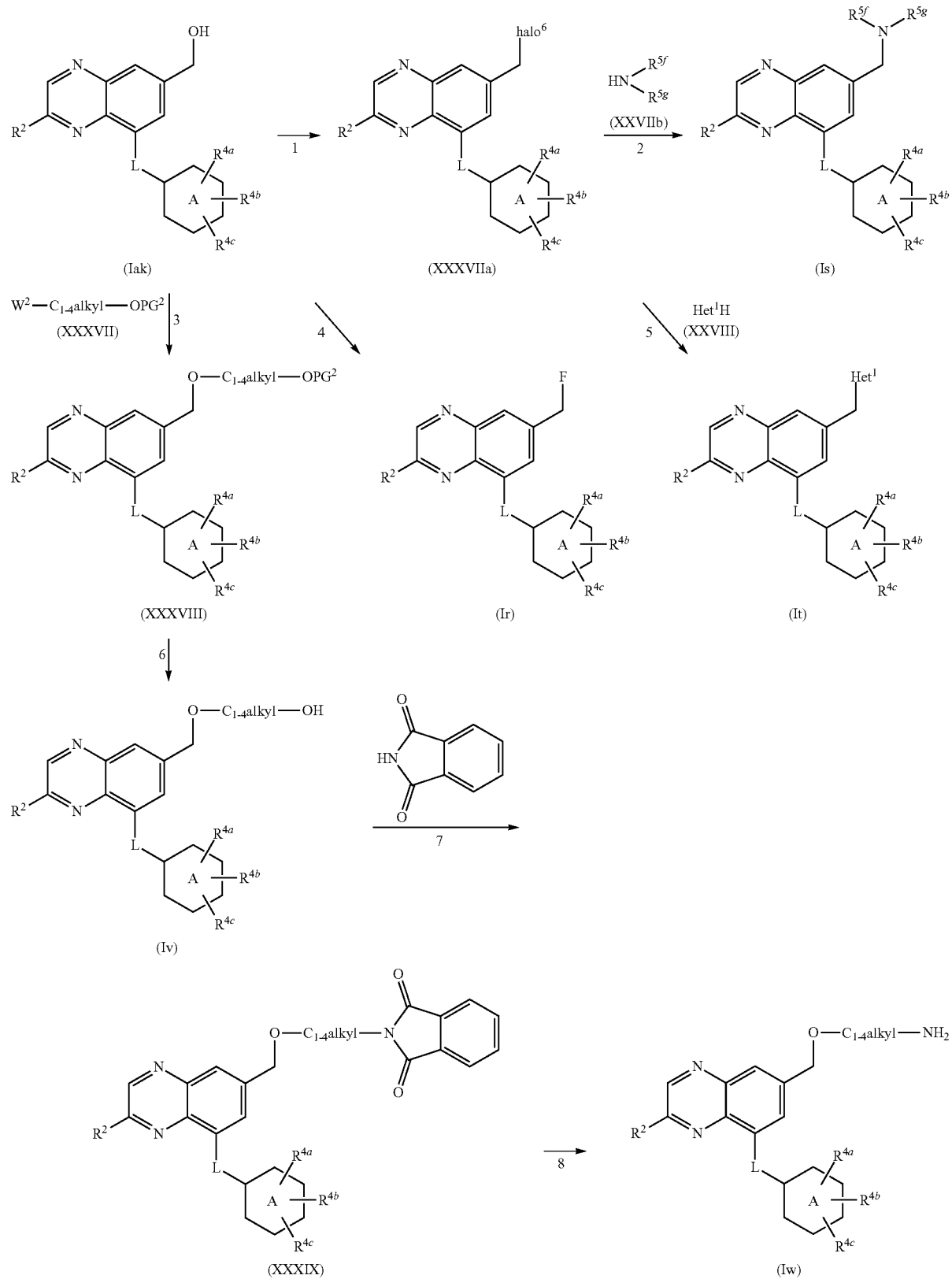

In Scheme 11, the following reaction conditions apply:

1: in the presence of a suitable halogenating reagent such as for example thionyl chloride, in the presence of a suitable solvent such as for example dichloromethane, at a suitable temperature such as for example room temperature;

2: in the presence of a suitable solvent such as for example acetonitrile, at a suitable temperature such as for example 80° C.;

3: in the presence of a suitable deprotonating reagent such as for example sodium hydride, a suitable solvent such as for example N,N-dimethylformamide, at a suitable temperature such as for example room temperature;

4: in the presence of a suitable fluorinating reagent such as for example diethylaminosulfur trifluoride, a suitable solvent such as for example dichloromethane, at a suitable temperature such as for example room temperature;

5: in the presence of a suitable solvent such as for example acetonitrile, at a suitable temperature such as for example 80° C.;

6: in the presence of a suitable acid such as for example trifluoroacetic acid, a suitable solvent such as for example methanol, at a suitable temperature such as room temperature;

7: in the presence of a suitable reagent such as for example di-tert-butyl azodicarboxylate, a suitable phosphine such as for example triphenylphosphine, a suitable solvent such as for example tetrahydrofuran, at a suitable temperature such as for example room temperature;

8: in the presence of a suitable reagent such as for example hydrazine monohydrate, a suitable solvent such as for example ethanol, at a suitable temperature such as for example 80° C.

Compounds of formula (I) wherein Y is $Y^1$ being $CR^3$ and $R^3$ is defined $C_{2-4}$alkyl substituted with one substituent selected from the group consisting of fluoro, —$NR^{5f}R^{5g}$, $Het^1$, —O—$C_{1-4}$alkyl-OH, and —O—$C_{1-4}$alkyl-$NH_2$ can be prepared from the aldehyde I(k) using coupling such as Wittig or Homer Emmons olefinaltion with the appropriate coupling partner followed by reduction of the double bond.

In general, compounds of formula (I) wherein Y is $Y^6$ being $CR^3$ and $R^3$ is defined as $C_{1-4}$alkyl substituted with one substituent selected from the group consisting of —O—(C=O)—CH($NH_2$)—$C_{1-4}$alkyl, —O—(C=O)—CH($NH_2$)—$C_{1-4}$alkyl-Ar and

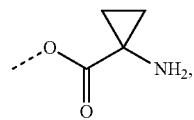

said compounds being respectively represented by formula (Ix), (Iy) and (Iz) can be prepared according to the following reaction Scheme 12 wherein $PG^3$ is defined as a protective group such for example Boc. All other variables in Scheme 12 are defined as above or according to the scope of the present invention.

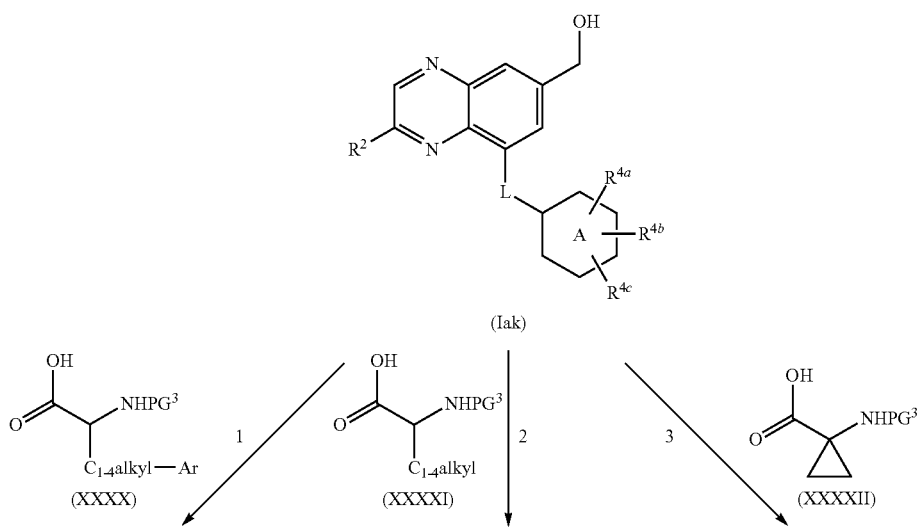

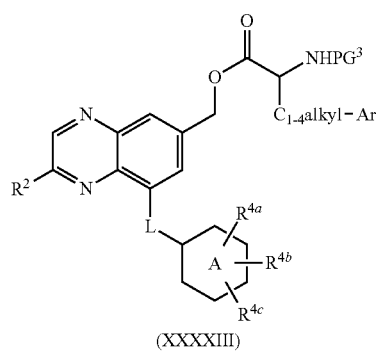 (XXXXIII)

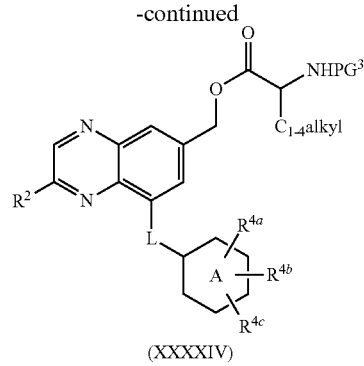 (XXXXIV)

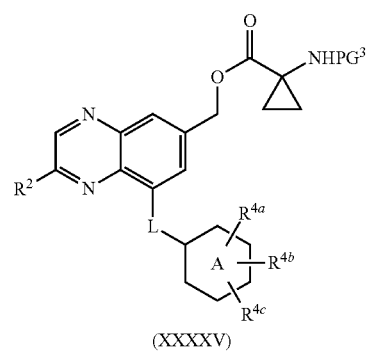 (XXXXV)

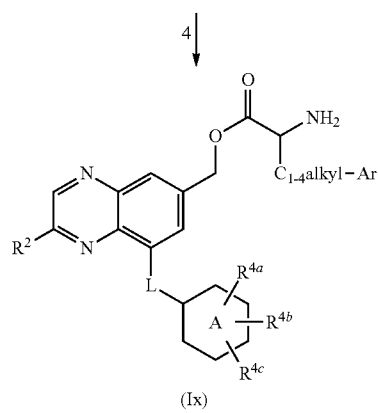 (Ix)

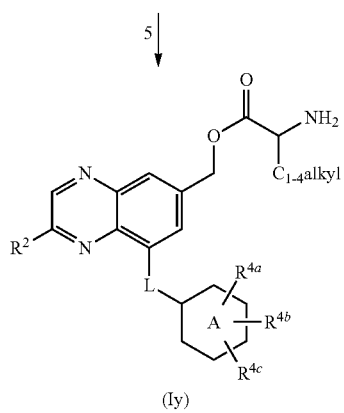 (Iy)

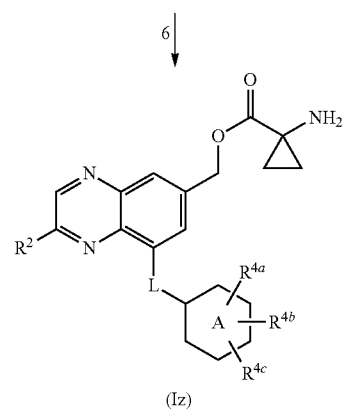 (Iz)

In Scheme 12, the following reaction conditions apply:

1: in the presence of a suitable coupling reagent such as for example 1-[bis(dimethylamino)methylene]-1H-1,2,3-Triazolo[4,5-b]pyridinium 3-oxide, a suitable additive such as for example dimethylaminopyridine, a suitable base such as for example diisopropylethylamine, and in a suitable solvent such as for example of DMF;

2: in the presence of an acid such as for example trifluoroacetic acid or hydrogen chloride in a suitable solvent such as for example dichloromethane or methanol.

Alternatively, in the presence of palladium on charcoal, in a suitable solvent such as methanol under an atmosphere of hydrogen.

Intermediates of formula (XIXaa) when Y is $Y^7$ being $CR^3$ wherein $R^3$ is defined as —(C═O)—O—$C_{1-4}$alkyl used in the above Scheme 6 can alternatively be prepared according to the following reaction scheme 13 wherein $halo^1$ is defined as above. All other variables in Scheme 13 are defined according to the scope of the present invention.

Scheme 13

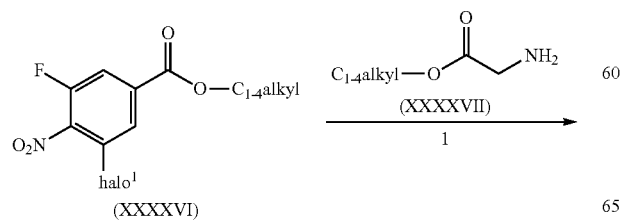
(XXXXVI)          (XXXXVII)

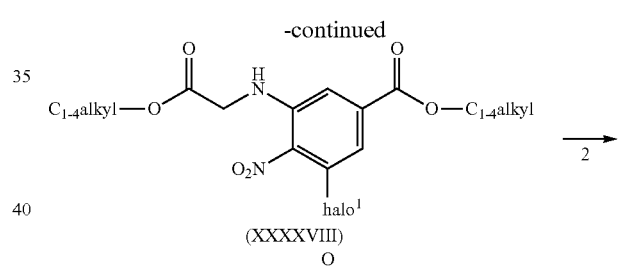 (XXXXVIII)

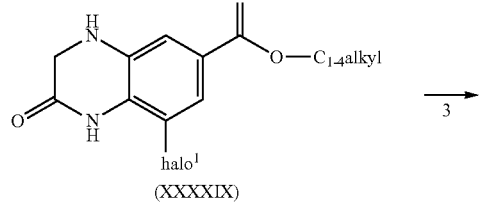 (XXXXIX)

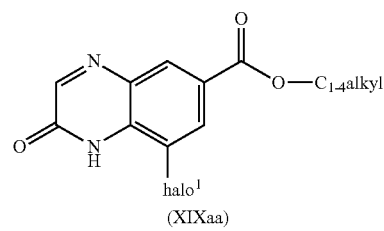 (XIXaa)

In Scheme 13, the following reaction conditions apply:

1: in the presence of a suitable base such as for example diisopropylethylamine, a suitable solvent such as for example dimethylacetamide, at a suitable temperature such as room temperature;

2: in the presence of a suitable reducing reagent such as for example Tin(II) chloride dihydrate, a suitable solvent such as for example ethanol, at a suitable temperature such as 80° C.;

3: in the presence of a suitable oxidative reagent such as for example manganese dioxide, a suitable solvent such as for example dichloromethane at a suitable temperature such as room temperature.

In general, compounds of formula (I), wherein Y is $Y_1$ being N or $CR^3$ wherein $R^3$ is defined as —$C_{1-4}$alkyl, —(C=O)—O—$C_{1-4}$alkyl, —(C=O)—O—$NR^{5a}R^{5b}$, —C(=O)—$Het^1$ or halo, said compounds being represented by formula (Ic), already described in scheme 2, can alternatively be prepared according to the following reaction Scheme 14. All variables in Scheme 14 are defined according to the scope of the present invention.

solvent such as for example toluene, at a suitable temperature such as for example 60° C., optionally in a sealed vessel;

Alternatively, in the presence of a suitable reagent such as for example diisopropylazodicarboxylate, a suitable phosphine such as for example tributylphosphine, in a suitable solvent such as for example tetrahydrofuran, keeping temperature at 0° C. during reagents addition and then, increase to 30° C.;

2: in the presence of a suitable acid such as for example thioglycolic acid, a suitable base such as for example 1,8-diazabicyclo(5.4.0)undec-7-ene, a suitable solvent such as for example acetonitrile, at a suitable temperature such as room temperature.

Intermediates of formula (LIII) and (LIV), wherein Y is $Y^8$ being $CR^3$ wherein $R^3$ is defined as —(C=O)—O—$NR^{5a}R^{5b}$, —C(=O)—$Het^1$, which may be used as starting material in the above Schemes 2 and 5 can be prepared according to the following reaction Scheme 15. All variables in Scheme 15 are defined as before or according to the scope of the present invention.

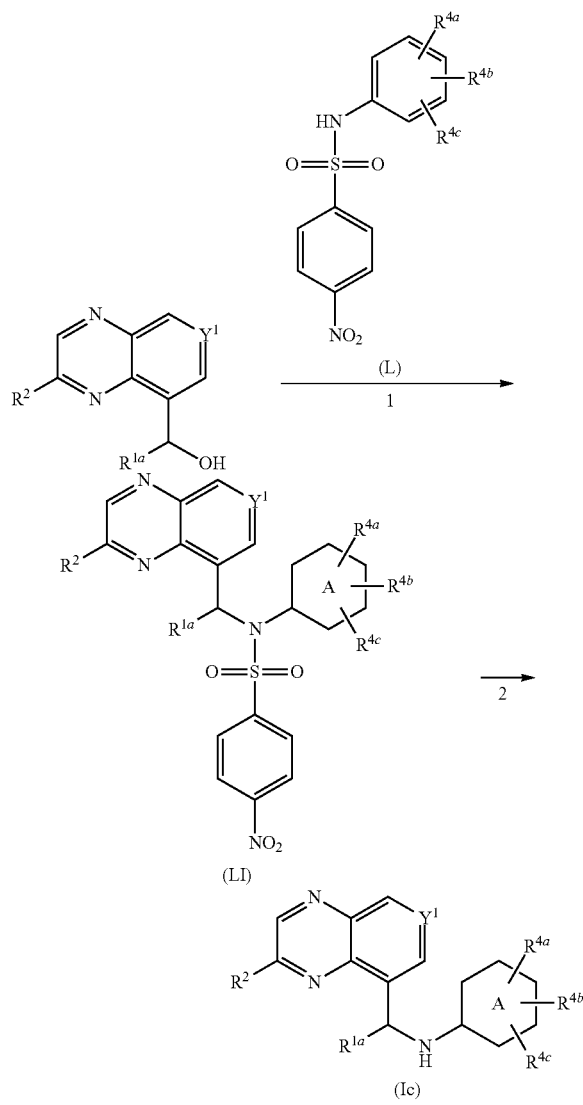

Scheme 14

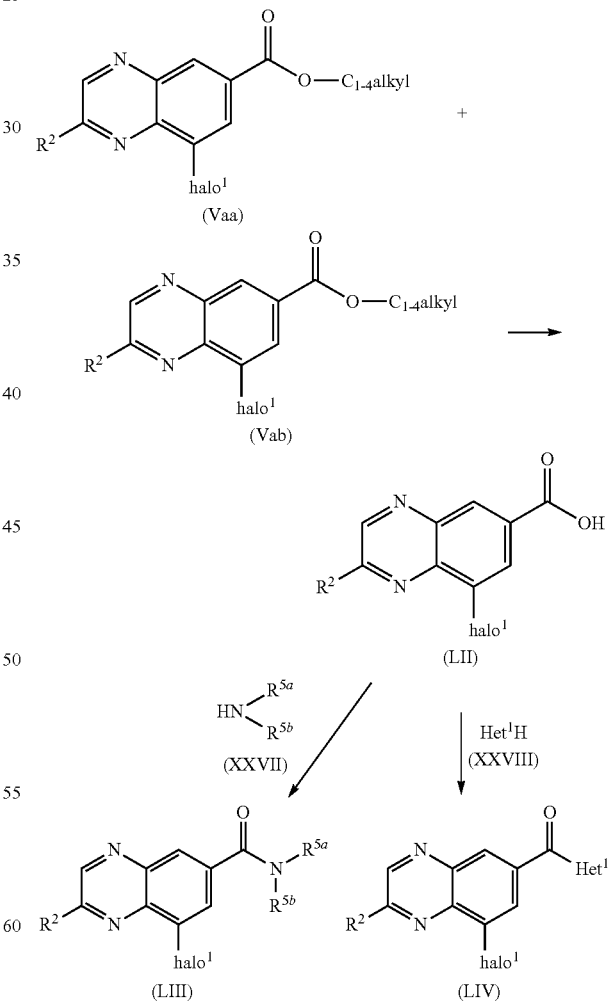

Scheme 15

In Scheme 14, the following reaction conditions apply:

1: in the presence of a suitable reagent such as for example cyanomethylene-tributylphosphorane, a suitable In Scheme 15, the following reaction conditions apply:

1: in the presence of a suitable base such as for example lithium hydroxide monohydrate or sodium hydroxide, a suitable solvent such as for example a mixture of water and tetrahydrofuran or a mixture of water, ethanol and tetrahydrofuran, at a suitable temperature such as room temperature;

2: in the presence of a suitable coupling reagent such as for example HBTU or 1,1'-carbonyldiimidazole, a suitable base such as for example diisopropylethylamine or 1,8-diazabicyclo[5.4.0]undec-7-ene, a suitable solvent such as for example N,N-dimethylformamide or methyltetrahydrofuran, at a suitable temperature such as for example room temperature.

In general, compounds of formula (I) wherein Y is $Y^9$ being $CR^3$ and $R^3$ is defined as $-CH_2-NH_2$, said compounds being represented by formula (Iaa) can be prepared according to the following reaction Scheme 16. All variables in Scheme 16 are defined as above or according to the scope of the present invention.

such as for example triphenylphosphine, a suitable solvent such as for example tetrahydrofuran, at a suitable temperature such as for example 40° C.;

2: in the presence of a suitable reagent such as for example hydrazine monohydrate, a suitable solvent such as for example methanol, at a suitable temperature such as for example 70° C.

Intermediates of formula (LIX) (subgroup of intermediates of formula (XI) used in the above Scheme 2) wherein Y is $Y^{10}$ being $CR^3$ wherein $R^3$ is defined as $-(C=O)-O-C_{1-4}alkyl$, can be prepared in enantiomerically pure form according to the following reaction Scheme 17. All variables in Scheme 17 are defined according to the scope of the present invention.

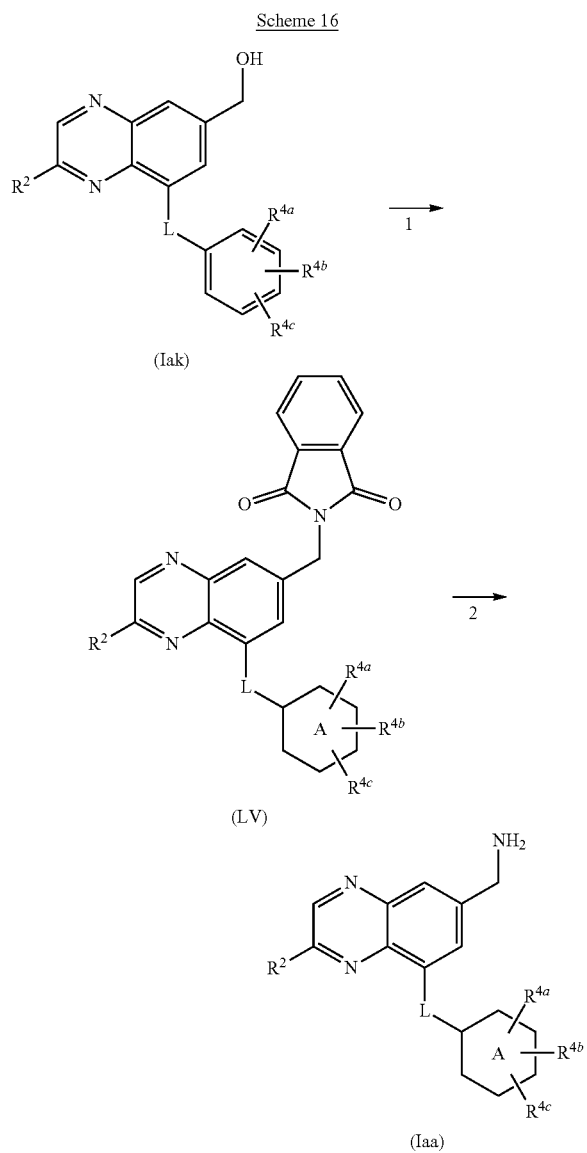

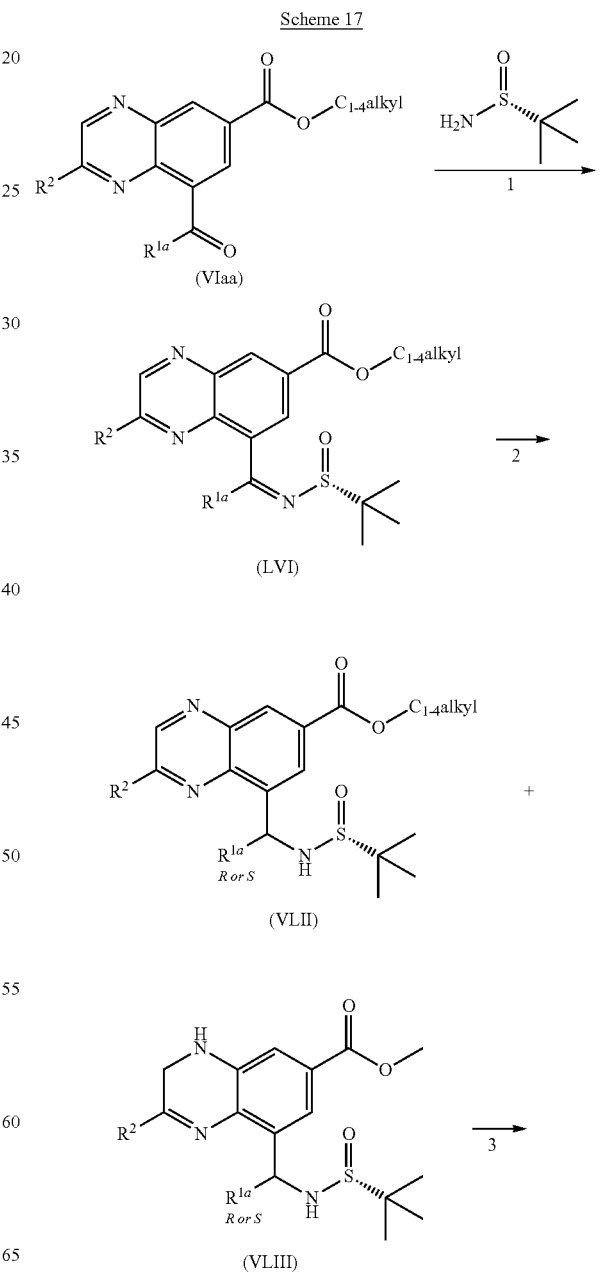

In Scheme 16, the following reaction conditions apply:
1: in the presence of a suitable reagent such as for example di-tert-butyl azodicarboxylate, a suitable phosphine -continued (VLII)

(LIX)

In Scheme 17, the following reaction conditions apply:

1: in the presence of a suitable reagent such as for example titanium (IV) ethoxide, a suitable solvent such as for example tetrahydrofuran or cyclopentyl methyl ether, at a suitable temperature such as for example room temperature;

2: in the presence of a suitable reducing reagent such as for example sodium cyanoborohydride, a suitable acid such as for example acetic acid, a suitable solvent such as for example a mixture of methanol and dichloromethane, at a suitable temperature such as for example −15° C.;

3: in the presence of a suitable oxidative reagent such as for example manganese dioxide, a suitable solvent such as for example dichloromethane, at a suitable temperature such as for example room temperature;

4: in the presence of a suitable acid such as for example hydrochloric acid, a suitable solvent such as for example a mixture of acetonitrile and 1,4-dioxane, at a suitable temperature such as for example room temperature.

Intermediates of formula (LXII) and (LXIII) (subgroups of intermediates of formula (XI) used in the above Scheme 2) wherein Y is $Y^{11}$ being $CR^3$ wherein $R^3$ is defined as —(C=O)—O—$NR^{5a}R^{5b}$, can be prepared according to the following reaction Scheme 18.

All variables in Scheme 18 are defined according to the scope of the present invention.

Scheme 18

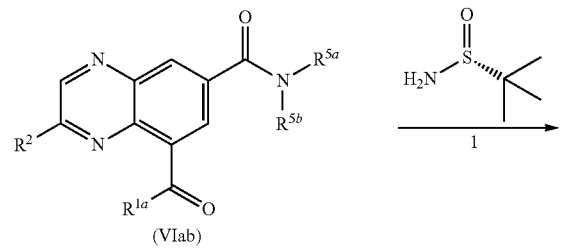

(VIab)

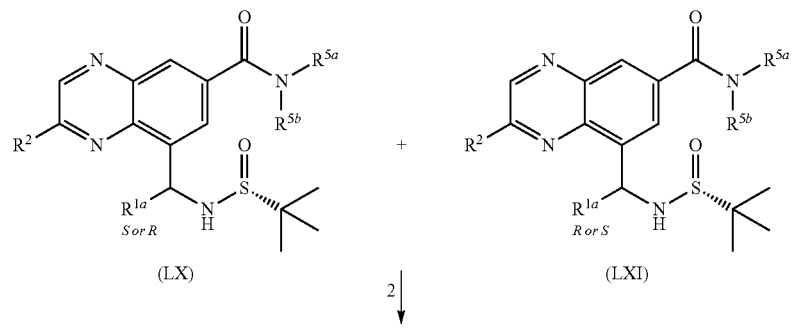

(LX)    (LXI)

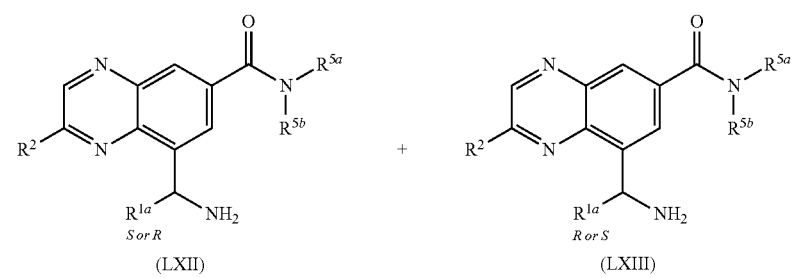

(LXII)    (LXIII)

In Scheme 18, the following reaction conditions apply:

1: in the presence of a suitable reagent such as for example titanium (IV) ethoxide, a suitable solvent such as for example tetrahydrofuran or cyclopentyl methyl ether, at a suitable temperature such as for example ranged from room temperature to solvent reflux; then, in the presence of a suitable reducing reagent such as for example sodium borohydride, at a suitable temperature such as for example ranged between −50° C. and room temperature;

2: in the presence of a suitable acid such as for example hydrochloric acid, a suitable solvent such as for example 1,4-dioxane, at a suitable temperature such as for example room temperature.

In general, compounds of formula (I) wherein L is $L^1$ being —$CHR^{1a}$—X— or —X—$CHR^{1c}$—; and Y is $Y^{12}$ being $CR^3$ wherein $R^3$ is defined as

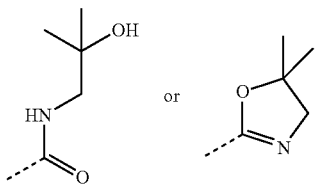

said compounds being represented respectively by formula (Iab) and (Iac), can be prepared according to the following reaction Scheme 19.

For the purpose of Scheme 19, X represents O, S, or $NR^{1b}$;

$R^{1l}$ represents $C_{1-4}$alkyl;

$R^{1c}$ represents hydrogen or $C_{1-4}$alkyl;

$R^{1b}$ represents hydrogen, $C_{1-4}$alkyl, —$CH_2$—C(=O)—$NR^{6a}R^{6b}$, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—.

All other variables in Scheme 19 are defined according to the scope of the present invention.

Scheme 19

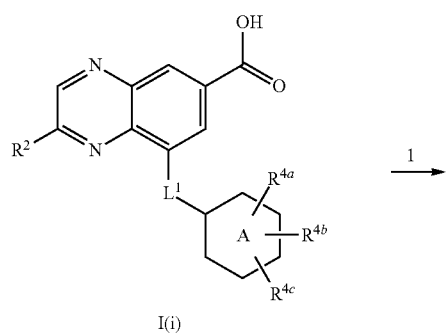

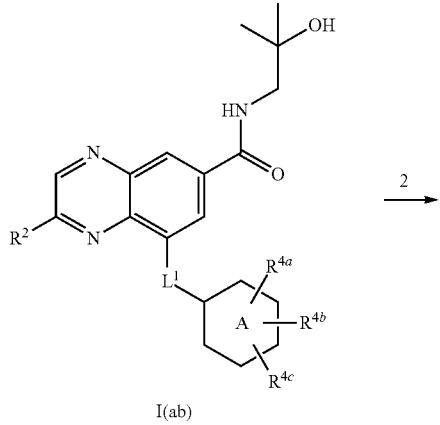

I(ab)

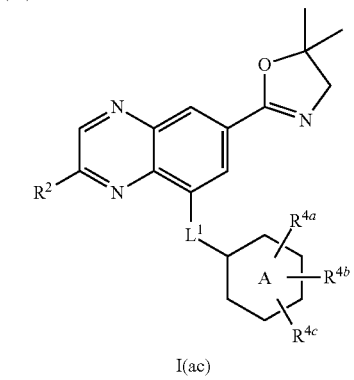

I(ac)

In Scheme 19, the following reaction conditions apply:

1: in the presence of a suitable coupling reagent such as for example HBTU or 1,1'-carbonyldiimidazole, a suitable base such as for example diisopropylethylamine or 1,8-diazabicyclo[5.4.0]undec-7-ene, a suitable solvent such as for example N,N-dimethylformamide or methyltetrahydo-furan, at a suitable temperature such as for example room temperature;

2: in the presence of a suitable halogenating reagent such as for example thionyl chloride, a suitable solvent such as for example dichloromethane, at a suitable temperature such as for example room temperature.

In general, compounds of formula (I) wherein Y is $Y^{13}$ being $CR^3$ wherein $R^3$ is defined as —CH=N—OH, said compounds being respectively represented by formula (Iam), can be prepared according to the following reaction Scheme 20 wherein all other variables are defined according to the scope of the present invention.

Scheme 20

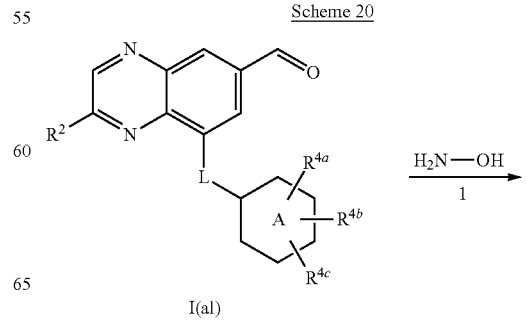

I(al)

-continued

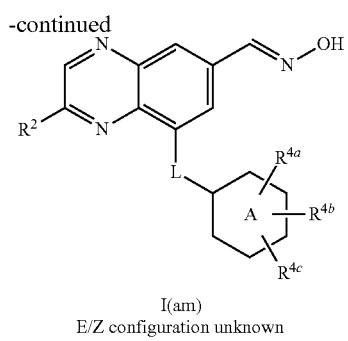

I(am)
E/Z configuration unknown

In Scheme 20, the following reaction conditions apply:

1: in the presence of a suitable solvent such as for example ethanol, at a suitable temperature such as for example 100° C.

In general, compounds of formula (I) wherein L is defined as —$CH_2$—X—; and Y is $Y^1$ being being N or $CR^3$ wherein $R^3$ is defined as —$C_{1-4}$alkyl, —(C=O)—O—$C_{1-4}$alkyl, —(C=O)—$NR^{5a}R^{5b}$, —C(=O)—$Het^1$ or halo; said compounds being represented respectively by formula (Iba) and (Ica), can be prepared according to the following reaction Scheme 21.

All other variables in Scheme 21 are defined as above or according to the scope of the present invention.

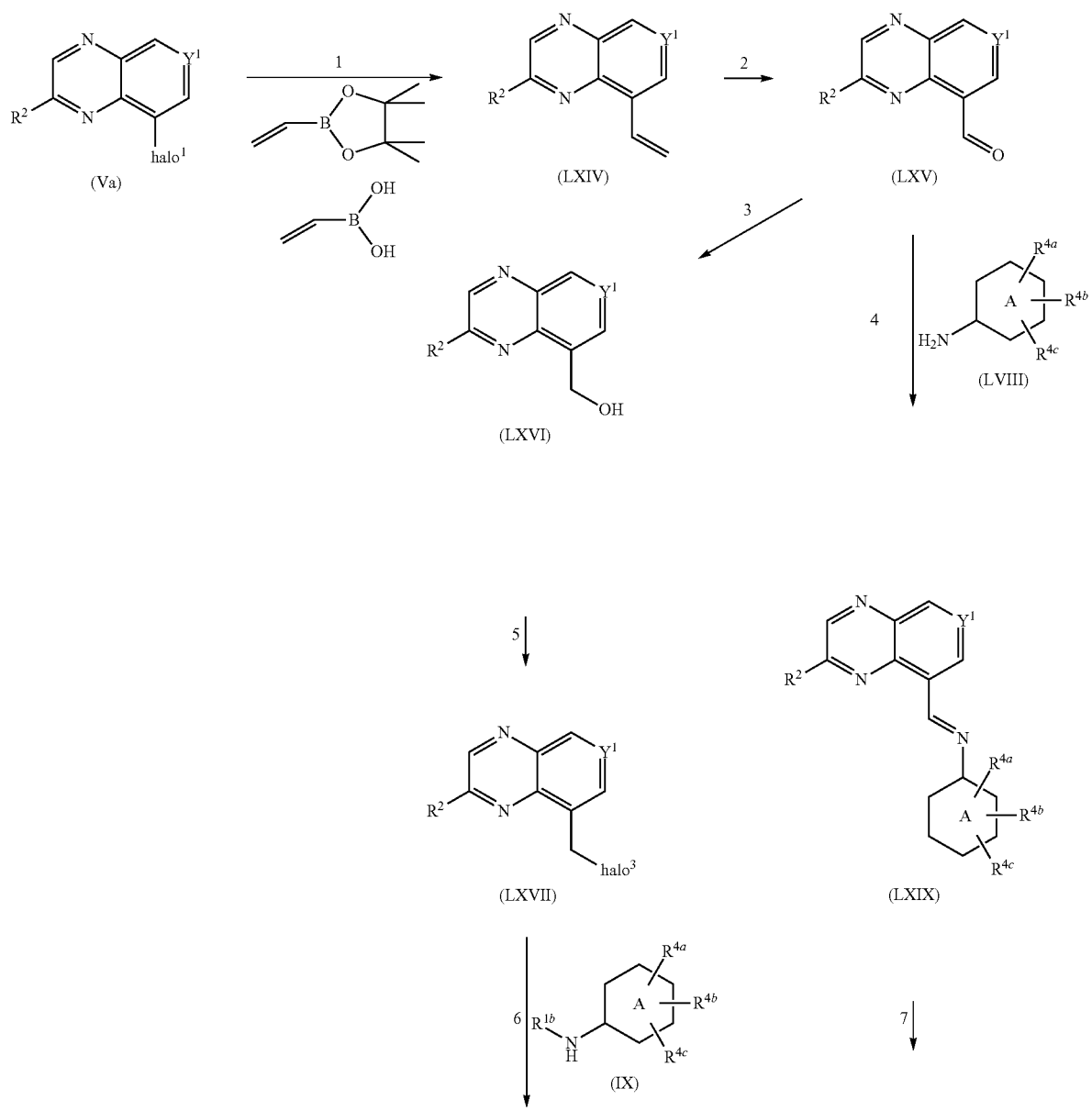

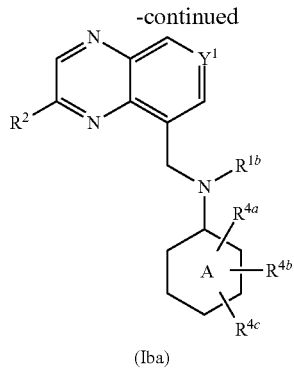

(Iba)

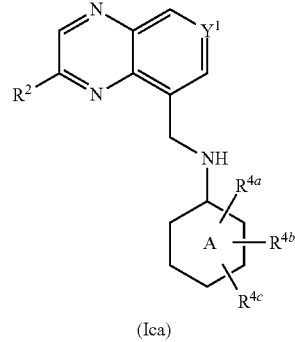

(Ica)

In Scheme 21, the following reaction conditions apply:

1: in the presence of a suitable catalyst such as for example [1,1'-bis(diphenyl-phosphino)ferrocene]dichloropalladium(II), complex with dichloromethane, a suitable base such as for example potassium phosphate, in a suitable solvent such as for example a mixture of dioxane and water, at a suitable temperature such as 90° C., optionally in a sealed reactor;

2: in the presence of a suitable oxidative agent such as for example osmium tetroxide and sodium periodate, in a suitable solvent such as for example tetrahydrofuran;

3: in the presence of a suitable reducing reagent such as for example sodium borohydride, a suitable solvent such as for example a mixture of methanol and dichloromethane, at a suitable temperature such as room temperature, in the presence or not of a suitable additive such as for example cerium (III) chloride;

4: in the presence of molecular sieve 4 Å, in a suitable solvent such as for example dichloromethane, optionally in a sealed reactor;

5: in the presence of a suitable halogenating reagent such as for example phosphorous tribromide or thionyl chloride, a suitable solvent such as for example dichloromethane, at a suitable temperature such as for example 10° C. or room temperature;

6: in the presence of a suitable solvent such as for example N,N-dimethylformamide, at a suitable temperature such as for example 50 or 60° C., in a sealed vessel;

7: in the presence of a suitable reducing agent such as for example sodium triacetoxyborohydride, in a suitable solvent such as for example dichloromethane;

In general, compounds of formula (I) wherein L is defined as —CH($C_{1-4}$alkyl-OH)—X—, and Y is defined as $CR^3$ wherein $R^3$ is defined as —(C=O)—$NR^{5a}R^{5b}$; said compounds being represented by formula I(ao), can be prepared according to the following reaction Scheme 22. All other variables in Scheme 22 are defined as above or according to the scope of the present invention.

Scheme 22

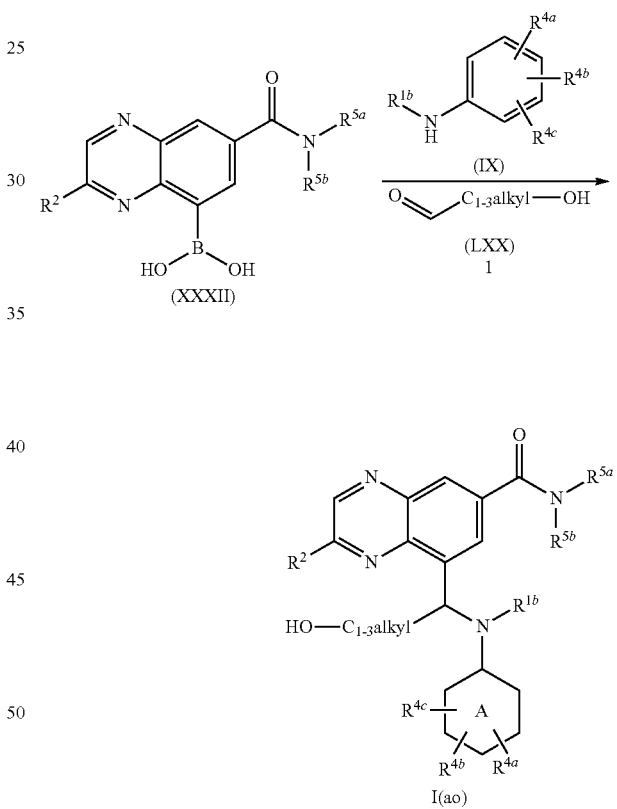

In Scheme 22, the following reaction conditions apply:

1: in a suitable solvent such as for example hexafluoroisopropanol.

In general, compounds of formula (I) wherein L is $L^1$ being —$CHR^{1a}$—X— or —X—$CHR^{1c}$—; and Y is $Y^a$ being $CR^3$ wherein $R^3$ is defined as —(C=O)—NH—$C^{1-4}$alkyl-Het$^1$, —(C=O)—N($C_{1-4}$alkyl)-$C_{1-4}$alkyl-Het$^1$, —$CH_2$—NHHet$^2$ or as —(C=O)—NH—$C_{1-4}$alkyl-Het$^2$, said compounds being represented respectively by compounds of formula I(ap), I(aq), I(ar), and I(as), can be prepared according to the following reaction Scheme 23.

All other variables in Scheme 23 are defined according to the scope of the present invention.

Scheme 23

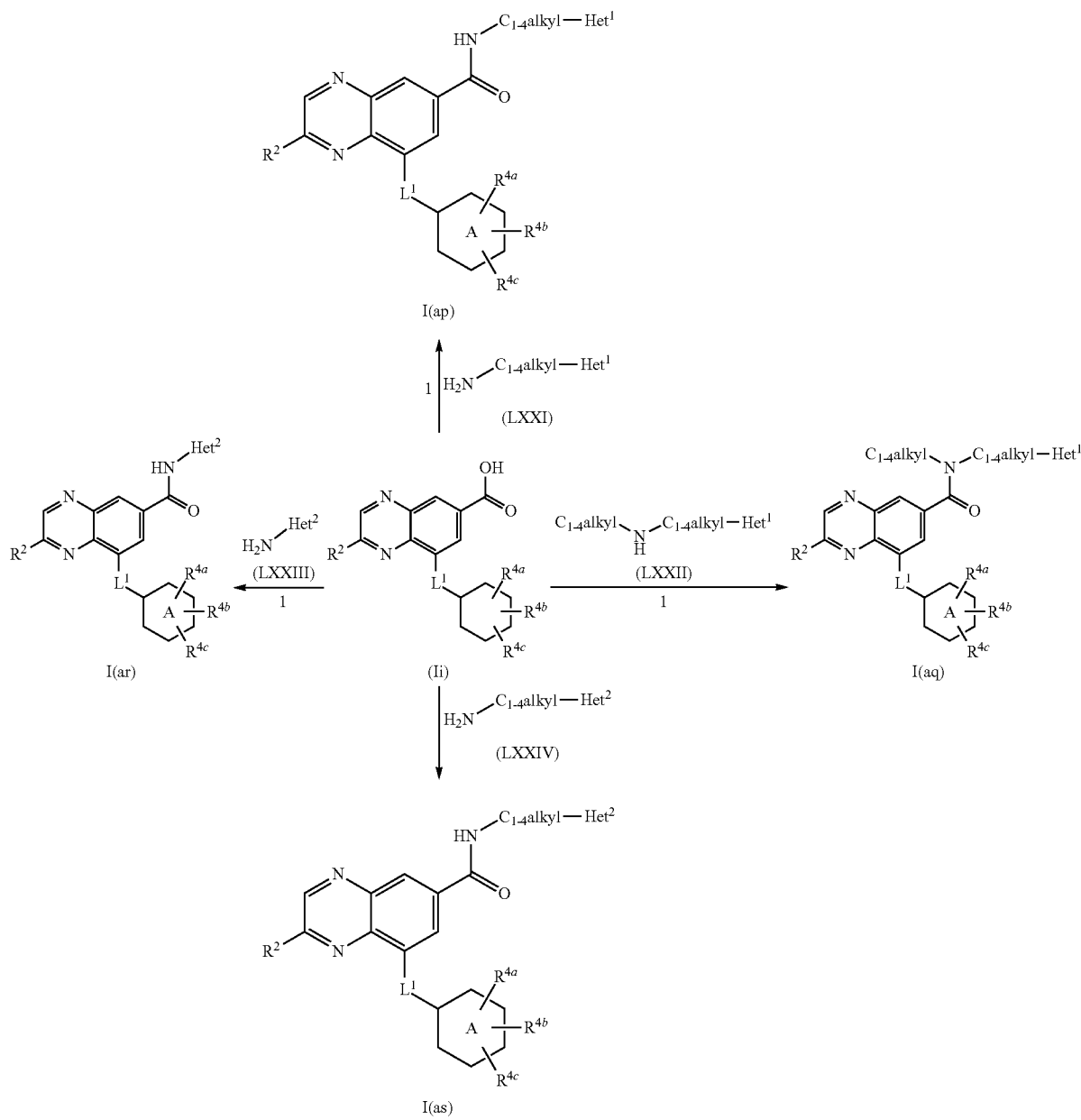

In Scheme 23, the following reaction conditions apply:

1: in the presence of a suitable coupling reagent such as for example N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate (HBTU), (1-Cyano-2-ethoxy-2-oxoethylidenaminooxy)dimethylamino-morpholino-carbenium hexafluorophosphate (COMU), 1-[Bis(dimethylamino)methylene]-1H-1,2,3-triazolo[4,5-b]pyridinium 3-oxid hexafluorophosphate (HATU) or 1,1'-carbonyldiimidazole, a suitable base such as for example diisopropylethylamine, triethylamine or 1,8-diazabicyclo[5.4.0]undec-7-ene, a suitable solvent such as for example N,N-dimethylformamide or methyltetrahydofuran, at a suitable temperature such as for example room temperature.

A subgroup of the Intermediates of formula (VII) used in the above Scheme 2, hereby named Intermediates of formula (VIIaa) wherein $R^2$ is restricted to

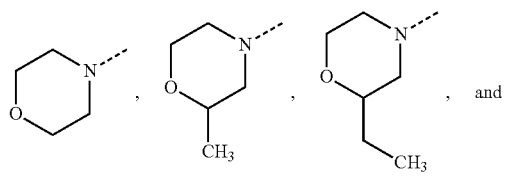

and

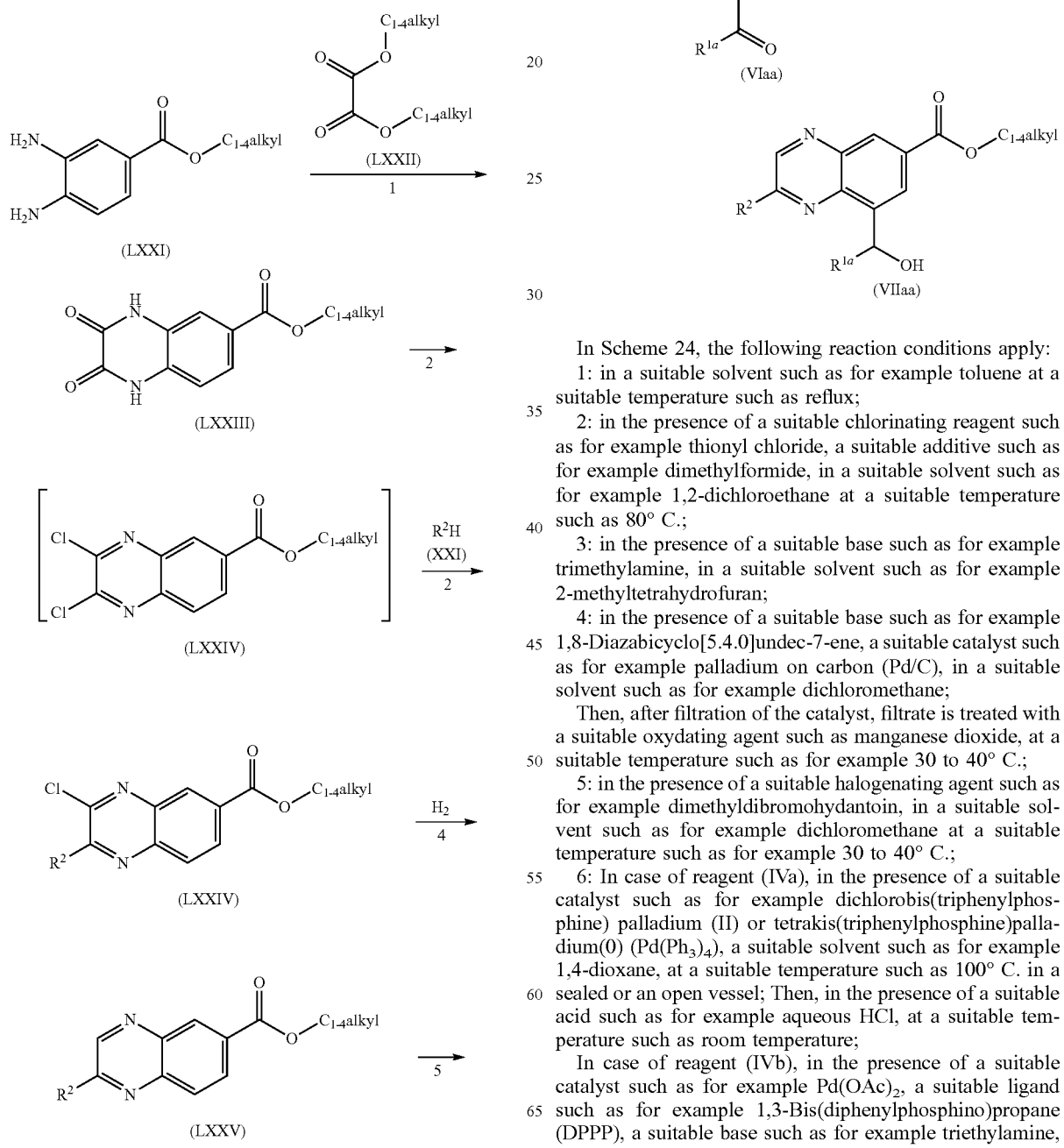

and Y is restricted to —C—(C=O)—O—C$_{1-4}$alkyl can be prepared according to the following reaction Scheme 24. All other variables in Scheme 24 are defined according to the scope of the present invention.

In Scheme 24, the following reaction conditions apply:

1: in a suitable solvent such as for example toluene at a suitable temperature such as reflux;

2: in the presence of a suitable chlorinating reagent such as for example thionyl chloride, a suitable additive such as for example dimethylformide, in a suitable solvent such as for example 1,2-dichloroethane at a suitable temperature such as 80° C.;

3: in the presence of a suitable base such as for example trimethylamine, in a suitable solvent such as for example 2-methyltetrahydrofuran;

4: in the presence of a suitable base such as for example 1,8-Diazabicyclo[5.4.0]undec-7-ene, a suitable catalyst such as for example palladium on carbon (Pd/C), in a suitable solvent such as for example dichloromethane;

Then, after filtration of the catalyst, filtrate is treated with a suitable oxydating agent such as manganese dioxide, at a suitable temperature such as for example 30 to 40° C.;

5: in the presence of a suitable halogenating agent such as for example dimethyldibromohydantoin, in a suitable solvent such as for example dichloromethane at a suitable temperature such as for example 30 to 40° C.;

6: In case of reagent (IVa), in the presence of a suitable catalyst such as for example dichlorobis(triphenylphosphine) palladium (II) or tetrakis(triphenylphosphine)palladium(0) (Pd(Ph$_3$)$_4$), a suitable solvent such as for example 1,4-dioxane, at a suitable temperature such as 100° C. in a sealed or an open vessel; Then, in the presence of a suitable acid such as for example aqueous HCl, at a suitable temperature such as room temperature;

In case of reagent (IVb), in the presence of a suitable catalyst such as for example Pd(OAc)$_2$, a suitable ligand such as for example 1,3-Bis(diphenylphosphino)propane (DPPP), a suitable base such as for example triethylamine, a suitable solvent such as for example dimethylsulfoxide, at a suitable temperature such as 100° C.; Then, in the presence of a suitable acid such as for example HCl, at a suitable temperature such as 0° C.;

7: in the presence of an enantioselective reducing agent such as for example (−)-B-chlorodiisopinocampheylborane, in a suitable solvent such as for example dichloromethane, at a suitable temperature such as −35° C.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PI3Kβ kinase activity, and optionally also have PI3Kδ inhibitory activity.

It is therefore anticipated that the compounds according to the present invention or pharmaceutical compositions thereof may be useful for treating or preventing, in particular treating, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like; in particular cancer.

Because the pharmaceutically active compounds of the present invention are active as PI3Kβ inhibitors, they exhibit therapeutic utility in treatment or prevention, in particular treatment, of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which exhibit mutation of PTEN, or mutation of an upstream activator of PI3Kβ kinase or overexpression of an upstream activator of PI3Kβ kinase, and are therefore susceptible to treatment with an PI3Kβ inhibitor, are known in the art, and include both primary and metastatic tumors and cancers. According to an embodiment, description of the treatment of a susceptible neoplasm may be used interchangeably with description of the treatment of a cancer.

According to one embodiment, "susceptible neoplasms" include but are not limited to PTEN-deficient neoplasms listed as follows: brain (gliomas), glioblastomas, leukemias, Bannayan-Zonana syndrome, Cowden disease, Lhermitte-Duclos disease, breast cancer, inflammatory breast cancer, colorectal cancer Wilm's tumor, Ewing's sarcoma, Rhabdomyosarcoma, ependymoma, medulloblastoma, colon cancer, head and neck cancer, liver cancer, kidney cancer, lung cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia. Mantle cell leukemia, Multiple myeloma, Megakaryoblastic leukemia, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, cervical cancer, vulval cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including tripnegative breast cancer, and glioma.

In an embodiment, the term "susceptible neoplasm" includes and is limited to prostate cancer, in particular hormone refractory prostate cancer.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of PI3Kβ kinase activity and optionally also for use in the inhibition of PI3Kδ.

The compounds of the present invention can be "anticancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of PI3Kβ mediated diseases or conditions.

The invention also relates to compounds of Formula (I) and N-oxides, pharmaceutically acceptable addition salts, and solvates thereof, for the treatment or prevention, in particular in the treatment, of PI3Kβ and optionally PI3Kδ mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of PI3Kβ.

The invention also relates to the use of compounds of Formula (I) and N-oxides, pharmaceutically acceptable addition salts, and solvates thereof, for the manufacture of a medicament for the inhibition of PI3Kβ and optionally also for the inhibition of PI3Kδ.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:
  platinum coordination compounds for example cisplatin optionally combined with amifostine, carboplatin or oxaliplatin;
  taxane compounds for example paclitaxel, paclitaxel protein bound particles (Abraxane®) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicanmycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

famesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b.

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-737;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa);

interleukin 11; oprelvekin; zoledronate, zoledronic acid; fentanvl;

bisphosphonate; palifermin;

a steroidal cytochrome P450 17alpha-hydroxylase-17,20-lyase inhibitor (CYP17), e.g. abiraterone, abiraterone acetate;

Glycolysis inhibitors, such as 2-deoxyglucose;

mTOR inhibitors such as rapamycins and rapalogs, and mTOR kinase inhibitors;

PI3K inhibitors and dual mTOR/PI3K inhibitors;

autophagy inhibitors, such as chloroquine and hydroxychloroquine;

antibodies that re-activate the immune response to tumors, for example nivolumab (anti-PD-1), lambrolizumab (anti-PD-1), ipilimumab (anti-CTLA4), and MPDL3280A (anti-PD-L1).

The compounds of the invention can also be advantageously combined with anti-androgen therapies including androgen receptor antagonists and inhibitors of androgen biosynthesis in PTEN-negative prostate cancers.

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art.

Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

These dosages may be administered for example once, twice or more per course of treatment, which may be repeated for example every 7, 14, 21 or 28 days.

EXAMPLES

The following examples illustrate the present invention.

Hereinafter, the term 'BOC', 'Boc' or 'boc' means tert-butoxycarbonyl, 'DCM' means dichloromethane, 'MeOH' means methanol, 'EtOH' means ethanol, 'ACN' means acetonitrile, 'THF' means tetrahydrofuran, 'Me-THF' means methyltetrahydrofuran, 'DMF' means dimethylformamide, 'EtOAc' means ethyl acetate, '$H_2O$' means water, '$Et_2O$' means diethyl ether, '$K_2CO_3$' means potassium carbonate, '$K_3PO_4$' means potassium phosphate, '$NH_4OH$' means ammonia aqueous solution, '$NaHCO_3$' means sodium bicarbonate, 'NaOH' means sodium hydroxide, 'NaCl' means sodium chloride, Celite®' means diatomaceous earth, 'NMP' means N-methylpyrrolidine, 'DIPEA' means diisopropylethylamine, '$iPrNH_2$' means isopropylamine, '$MgSO_4$' means magnesium sulfate, '$N_2$' means nitrogen, 'HCl' means hydrochloric acid, 'quant.' means quantitative, 'TFA' means trifluoroacetic acid, '$NaBH_4$' means sodium borohydride, '$LiAlH_4$' means lithium aluminium hydride, '$CO_2$' means carbon dioxide, 'SFC' means supercritical fluid chromatography, 'HBTU' means N,N,N',N'-tetramethyl-O-(1H-benzotriazol-1-yl)uronium hexafluorophosphate, O-(Benzotriazol-1-yl)-N,N,N',N'-tetramethyluronium hexafluorophosphate, 'TBAF' means tetrabutylammonium fluoride, '$PPh_3$' means triphenylphosphine, '$Pd(OAc)_2$' means palladium(II) acetate, '$Pd_2(dba)_3$' means tris(dibenzylideneacetone)dipalladium(0), 'BrettPhos' means 2-(dicyclohexyl-phosphino)3,6-dimethoxy-2',4',6'-triisopropyl-1,1'-biphenyl, 'rt' means room temperature, 'OR' means optical rotation, 'BrettPhos Precatalyst First Gen' means chloro[2-(dicyclohexylphosphino)-3,6-dimethoxy-2',4',6'-triisopropyl-1,1'-biphenyl][2-(2-aminoethyl)phenyl]palladium(II), 'Xantphos' means 4,5-Bis(diphenylphosphino)-9, 9-dimethylxanthene, 'de' means diastereomeric excess, 'ee' or 'e.e.' means enantiomeric excess, 'M.P' means melting point, 'DSC' means differential scanning calorimetry, 'K' means Kofler; 'COMU' means (1-Cyano-2-ethoxy-2-oxo-ethylidenaminooxy)dimethylamino-morpholino-carbenium hexafluorophosphate, 'HATU' means 1-[Bis(dimethylamino)methylene]-1H-1,2,3-triazolo[4,5-b]pyridinium 3-oxid hexafluorophosphate, 'SiOH or SiO₂' means silica, 'Et₃N' means trimethylamine, 'H₂' means hydrogene, 'Johnphos' means (2-Biphenyl)di-tert-butylphosphine, 'LCMS' means Liquid Chromatography-Mass Spectrometry, 'DPPP' means 1,3-Bis(diphenylphosphino)propane; 'DMSO' means dimethylsulfoxide; 'min' means minute(s).

When a stereocenter is indicated with 'RS' this means that a racemic mixture was obtained.

A. Preparation of the Intermediates

Example A1

Preparation of Intermediate 1a and Intermediate 1b

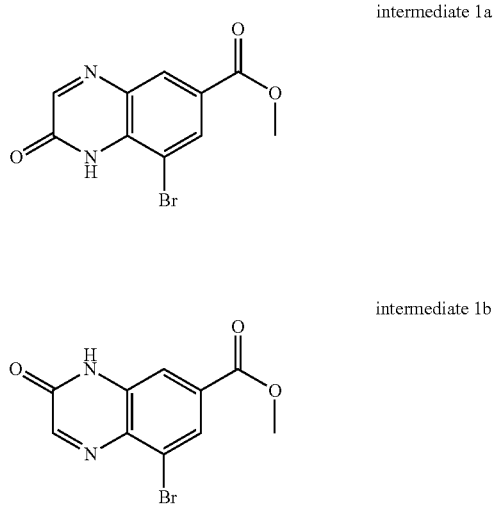

At −40° C., 2,2-dihydroxy-acetic acid (85.61 g; 930 mmol) in H₂O (35 mL) was added dropwise to a solution of methyl-3,4-diamino-5-bromobenzoate (190 g; 775.28 mmol) in MeOH (2 L). Then, the reaction mixture was allowed to warm to rt and stirred for 2 h. The solid was filtered, washed with Et₂O and dried under vacuum to give 214 g (98%) of a mixture of two intermediates 1a and 1b (ratio ~85/15 by ¹H NMR).

Alternative Pathway:

Ethyl glyoxalate solution (6.6 mL; 66.1 mmol; 50% in toluene) was added to a solution of methyl-3,4-diamino-5-bromobenzoate (8.1 g; 33.05 mmol) in EtOH (150 mL). The reaction mixture was heated at reflux for 3 h. The mixture was cooled down to rt and the precipitate was filtered, washed with diethylether and dried under vacuum to give 7.3 g (78%) of a mixture of intermediates 1a and 1b.

Alternative Preparation of Intermediate 1a

Preparation of Intermediate 1c

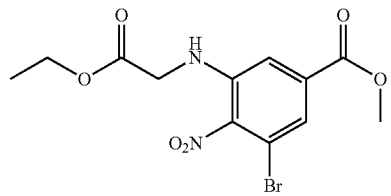 [SMILES: CCOC(=O)CNc1cc(C(=O)OC)cc(Br)c1[N+](=O)[O-]]

To a solution of methyl-3-bromo-5-fluoro-4-nitrobenzoate (2 g; 7.2 mmol) and glycine ethyl ester hydrochloride (1.1 g; 7.9 mmol) in DMA (20 mL) was added DIPEA (4.9 mL; 28.8 mmol) at rt. The mixture was stirred at rt for 2 days. H₂O and EtOAc were added. The organic layer was extracted, dried over MgSO₄, filtered and evaporated to dryness under vacuum to give 3.3 g of crude intermediate. A purification was performed by silica gel chromatography (irregular SiOH 20-45 μm, 40 g, mobile phase: gradient from 100% heptane to 70% heptane, 30% EtOAc). The fractions containing the product were mixed and evaporated to give 2.1 g (81%) of intermediate 1c.

Preparation of Intermediate 1d

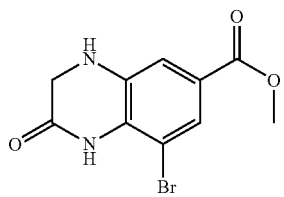 [SMILES: COC(=O)c1cc(Br)c2c(c1)NCC(=O)N2]

Intermediate 1c (200 mg; 0.55 mmol) was dissolved in EtOH (5 mL). Tin (II) chloride dihydrate (315 mg; 1.66 mmol) was added and the mixture was heated at 80° C. for 4 hours and cooled down to rt. The resulting precipitate was filtered, washed with EtOH and dried (vacuum, 60° C., overnight) to give 90 mg (57%) of intermediate 1d.

Preparation of Intermediate 1a

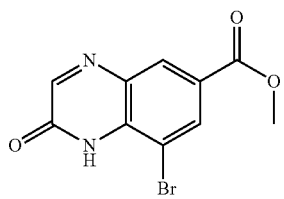 [SMILES: COC(=O)c1cc(Br)c2[nH]c(=O)cnc2c1]

To a solution of intermediate 1d (90 mg; 0.32 mmol) in DCM (10 mL) was added manganese dioxide (110 mg; 1.26 mmol). The solution was stirred at rt for 2 hours. Manganese dioxide (55 mg; 0.63 mmol) was again added and the solution was stirred overnight at rt. The mixture was filtered through a pad of Celite®, washed with DCM and the solvent was evaporated to dryness to give 58 mg (65%) of intermediate 1a.

Preparation of Intermediate 2a and Intermediate 2b

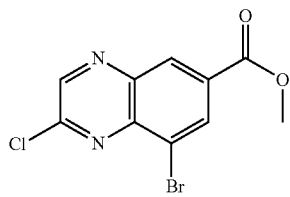
intermediate 2a

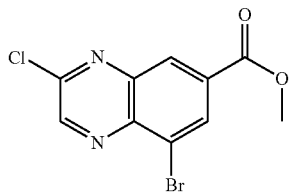
intermediate 2b

A mixture of intermediate 1a and 1b (85/15) (25 g; 75.07 mmol) was added slowly to POCl₃ (300 mL). The reaction mixture was heated at 80° C. for 3 h. POCl₃ was evaporated and DCM was added to the residue. The mixture was poured into ice-water and extracted with DCM. The organic layer was dried over MgSO₄, filtered and evaporated. The residue was purified by chromatography over silica gel (eluent: from 9/1 petroleum ether/EtOAc to 4/1 petroleum ether/EtOAc). The pure fractions were collected and the solvent was evaporated to give 17 g (75%) of intermediate 2a and 3 g (13%) of intermediate 2b.

Alternative Pathway:

A mixture of intermediate 1a (5 g; 17.7 mmol) in POCl₃ (75 mL) was heated at 80° C. for 4 h. The mixture was evaporated under vacuum and the residue was taken-up in ice water and DCM. The mixture was slowly basified with a 10% aqueous solution of K₂CO₃ and stirred at rt for 2 h. The aqueous layer was separated and extracted with DCM (2×). The combined organic layers were dried over MgSO₄, filtered and evaporated under vacuum to give 4.89 g (92%, beige solid) of intermediate 2a.

Preparation of Intermediate 3a and Intermediate 3b

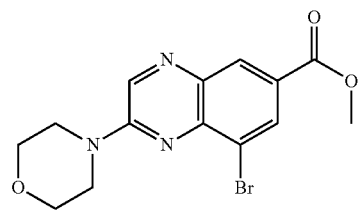
intermediate 3a

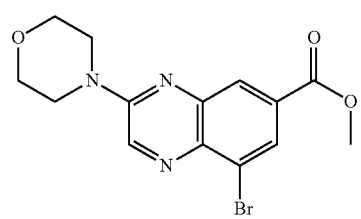
intermediate 3b

Triethylamine (95.4 mL; 660 mmol) was added to a mixture of intermediates 1a and 1b (75 g; 132.47 mmol) (ratio 1a/1b undetermined) in THF (3 L) at 0° C. The reaction mixture was stirred at 0° C. for 10 min. Then, morpholine (55.8 mL; 634 mmol) and bromo-tris-pyrrolidino-phosphonium hexafluorophosphate (135.2 g; 290 mmol) were added. The reaction mixture was stirred at rt for 12 h. The solvent was evaporated and the residue was washed with H₂O. The solid (yellow) was filtered, washed with ACN, then Et₂O and dried under vacuum to give 80 g (85%) of a mixture intermediates 3a and 3b (ratio ~4/1 by 1H NMR).

Alternative Pathway:

A mixture of intermediate 2a (3.3 g; 10.94 mmol) and morpholine (2.9 mL; 32.83 mmol) in THF (50 mL) was heated at reflux for 3 h. The reaction mixture was cooled down to rt, then poured into ice-water and extracted with EtOAc. The organic layer was washed with brine (2×), then water, dried over MgSO₄, filtered and evaporated to give 3.7 g (95%) of intermediate 3a.

Alternative Preparation of Intermediate 3a:

Intermediate 27 was dissolved in dichloromethane (10 volumes) and dimethyl dibromohydantoin (0.8 equivalents) was added. After reacting at 30-40° C. for 30 hours, the reaction mixture was washed with a saturated solution of ammonium chloride and the organic phase was concentrated to give intermediate 3a in quantitative yield (78% purity).

Preparation of Intermediate 4

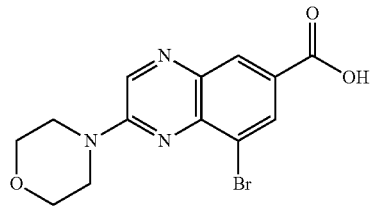 [SMILES: O=C(O)c1cc(Br)c2nc(N3CCOCC3)cnc2c1]

A solution of lithium hydroxide monohydrate (5.96 g; 141.97 mmol) in H₂O (60 mL) was added to a solution of a mixture of intermediates 3a and 3b (5/1) (10 g; 28.39 mmol) in THF (200 mL) at rt. The reaction mixture was stirred at rt overnight. At 0° C., the solution was slowly acidified with a 3N aqueous solution of HCl and stirred at 10° C. for 1 h. The precipitate was filtered, then washed with water and dried to give 7.4 g (70%. yellow solid. 91% of purity evaluated by LC/MS) of intermediate 4. M.P.: >260° C. (Kofler).

Alternative Pathway:

A 3M aqueous solution of NaOH (11.6 mL; 34.8 mmol) was added to a mixture of intermediates 3a and 3b (4.08 g; 11.6 mmol) in EtOH (60 mL) and THF (60 mL). The reaction mixture was stirred at rt overnight and evaporated under vacuum. The residue was acidified with a 0.5 N aqueous solution of HCl to give a precipitate. The solid was filtered off, washed with water, then diethylether and dried under vacuum to give 3.86 g (99%, yellow solid) of intermediate 4.

Example A2

Preparation of Intermediate 5

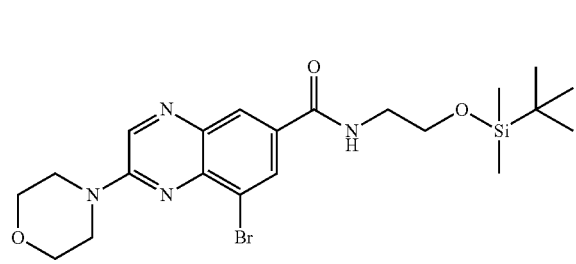 [SMILES: CC(C)(C)[Si](C)(C)OCCNC(=O)c1cc(Br)c2nc(N3CCOCC3)cnc2c1]

At 10° C., HBTU (10.093 g, 26.615 mmol) was added portion wise to a mixture of intermediate 4 (9 g, 26.615 mmol), N,N-Diisopropylethylamine (11.621 mL, 66.536 mmol) and 2-(t-butyldimethylsilyl)oxyethanamine (7 g, 39.922 mmol) in DMF (165 mL). The reaction mixture was stirred for 18 h. H$_2$O and EtOAc were added. The reaction mixture was extracted and the organic layer was separated, dried over MgSO$_4$, filtered and concentrated to give 22 g of a intermediate residue which was taken up with DCM. The precipitate was filtered. The mother layer was concentrated and purified by silica gel chromatography (330 g of SiO$_2$, 20-45 μm, gradient from 100% DCM to 95% DCM 5% MeOH 0.1% NH$_4$OH). The pure fractions were collected and evaporated until dryness to afford 9.6 g (73%) of intermediate 5.

Preparation of Intermediate 6

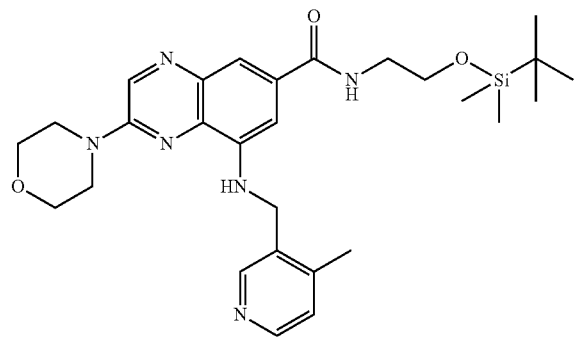 [SMILES: Cc1ccncc1CNc1cc(C(=O)NCCO[Si](C)(C)C(C)(C)C)cc2ncc(N3CCOCC3)nc12]

In a sealed tube, a mixture of intermediate 5 (0.5 g, 1.01 mmol), (4-Methylpyridin-3-yl)methylamine (0.108 mL, 1.21 mmol) and cesium carbonate (0.66 g, 2.02 mmol) in tert-amyl alcohol (5 mL) was degazed with N$_2$. 2-Dicyclohexyphosphino-2',6'-diisopropoxy-1,1'-biphenyl (23.544 mg, 0.0505 mmol) and BrettPhos Precatalyst First Gen (40.305 mg, 0.0505 mmol) were added, the reaction mixture was purged with N$_2$ and heated at 100° C. for 18 h. Water and Ethyl acetate were added. The aqueous layer was extracted and the organic layer was separated, dried over MgSO$_4$, filtered and concentrated. This crude (578 mg) was purified by silica gel chromatography (25 g of SiOH, 15 μm, gradient from 100% DCM to 90/10/0.1 DCM/MeOH/NH$_4$OH). The fractions containing the product were collected and evaporated until dryness to afford 405 mg (74%) of intermediate 6 which was used in the next step without any further purification.

Preparation of Intermediate 7

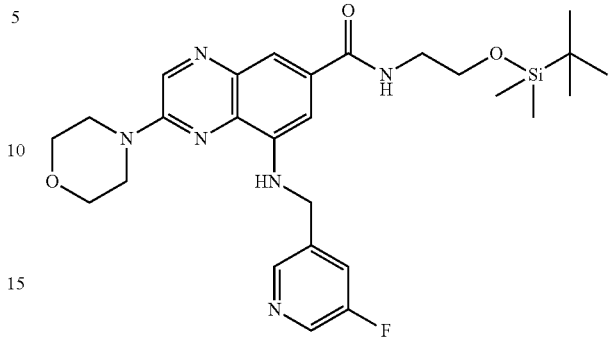

Intermediate 7 was prepared according to an analogous procedure as described for the synthesis of intermediate 6 using intermediate 5 and 3-amonomethyl-5-fluoropyridine as starting materials (400 mg, 74%).

Example A3

Preparation of Intermediate 8a and Intermediate 8b

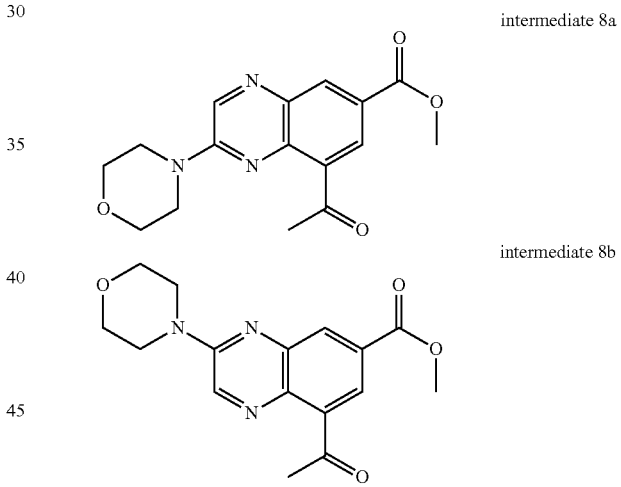

Tributyl(1-ethoxyvinyl)tin (67.68 g; 187.40 mmol) was added to a solution of a mixture of intermediates 3a and 3b (60 g; 85.18 mmol) in anhydrous 1,4-dioxane (1.2 L) under N$_2$. Dichlorobis(triphenylphosphine) palladium (II) (3.59 g; 5.11 mmol) was added and the mixture was purged again with N$_2$. The reaction mixture was heated at 100° C. overnight. After cooling down to rt, a 3M aqueous solution of HCl was added and the mixture was stirred at rt for 40 min. The mixture was slowly basified with a saturated aqueous solution of NaHCO$_3$ and EtOAc was added. The mixture was extracted with EtOAc and the organic layer was washed with brine, dried with Na$_2$SO$_4$ and evaporated. The residue was purified by column chromatography over silica gel (eluent: from DCM/EtOAc 10/1 to DCM/EtOAc 8/1). The pure fractions were collected and the solvent was evaporated to give a 10 g of mixture of intermediate 8a and intermediate 8b and 30.5 g (54%) of intermediate 8a. The 10 g mixture of intermediate 10a and intermediate 8b was further purified by chromatography over silica gel (eluent: from DCM/EtOAc 10/1 to DCM/EtOAc 4/1). The pure fractions were collected and the solvent was evaporated to give 1.6 g (3%) of intermediate 8b and 7 g of a mixture (intermediate 8a and intermediate 8b) (ratio 1/1 by NMR).

Alternative Preparation:

To a solution of a mixture of intermediates 3a and 3b (75/25 evaluated by LC/MS) (195 g, 554 mmol) in DMSO (2000 mL) was added vinylbutylether (166 g, 1661. mmol) and tri-ethyl amine (400 mL, 2768 mmol, 0.7 g/mL) under N₂ atmosphere. Pd(OAc)₂ (12.4 g, 55 mmol) and DPPP (45.6 g, 111 mmol) were added. The mixture was purged again with N₂ and heated to 100° C. overnight. After cooling down to room temperature, HCl (3M, 1845 mL, 5536 mmol) was added portionwise under ice batch and the mixture was stirred for 1 hour. The pH of the mixture was adjusted to 8 with NaHCO₃. The mixture was filtered. The cake was washed with ethyl acetate (1000 mL), then dissolved in CH₂Cl₂ (1500 mL*2) and filtered. The filtrate was washed with brine (500 mL), evaporated to give a crude yellow solid (200 g) mainly containing intermediate 8a. This residue was purified by silica gel chromatography (eluent: ethyl acetate=100%). The desired fractions were collected and the solvent was concentrated to dryness under vacuum to give 100 g (57%) of intermediate 8a as yellow solid.

Alternatively, the previous reaction was also carried out using EtOH as solvent at a temperature of 70° C.

Preparation of Intermediate 9

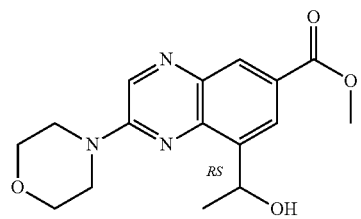 [SMILES: COC(=O)c1cc(C(C)O)c2nc(N3CCOCC3)cnc2c1]

Cerium(III) chloride (8.2 g; 33.3 mmol) was added to a solution of intermediate 8a (10 g; 31.7 mmol) in MeOH (220 mL) and DCM (100 mL). The reaction mixture was stirred at rt for 30 min. The mixture was cooled down to 0° C. and NaBH₄ (1.32 g; 34.9 mmol) was added portionwise (bubbling in the mixture). The reaction mixture was stirred at rt for 1 h 30. Then, DCM and water were added. The layers were separated, the aqueous layer was extracted with DCM (2×) and the combined organics layers were dried over MgSO₄, filtered off and evaporated in vacuum. The residue (9.65 g) was recrystallized with MeOH and diethylether. The precipitate was filtered and dried to give 7.98 g (79%) of intermediate 9.

Alternative Pathway:

NaBH₄ (1.01 g; 26.6 mmol) was added to a solution of intermediate 8a (7.94 g; 22.2 mmol) in MeOH (140 mL) and DCM (70 mL) at 0° C. The reaction mixture was slowly warmed to rt and stirred for 30 min. The mixture was slowly quenched with water. DCM was added and the layers were separated. The aqueous layer was extracted with DCM (2×). The combined organic layers were dried over MgSO₄, filtered and evaporated under vacuum. The residue (7.9 g, orange solid) was purified by chromatography over silica gel (regular SiOH; 30 μm; 300 g; gradient: from 70% DCM, 30% EtOAc to 30% DCM, 70% EtOAc). The pure fractions were collected and the solvent was evaporated. The residue (5.35 g, yellow solid) was triturated in diethylether and filtered to give 4.95 g (70%/o, pale yellow solid) of intermediate 9.

Preparation of Intermediate 10

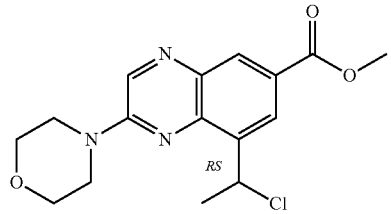 [SMILES: COC(=O)c1cc(C(C)Cl)c2nc(N3CCOCC3)cnc2c1]

At 0° C., thionyl chloride (6.2 mL; 85.08 mmol) was added dropwise to a solution of intermediate 9 (13.5 g; 42.54 mmol) in DCM (500 mL). The solution was stirred at 10° C. for 4 hours. Then, the solvent was evaporated to dryness to give 15 g of intermediate 10 which was used without any further purification Example A4

Preparation of Intermediate 11

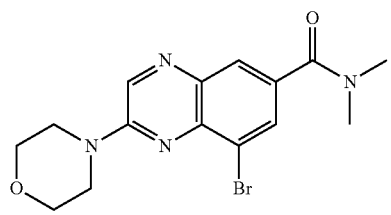 [SMILES: CN(C)C(=O)c1cc(Br)c2nc(N3CCOCC3)cnc2c1]

At 10° C., HBTU (10.7 g; 28.1 mmol) was added portion wise to a mixture of intermediate 4 (9.5 g; 28.1 mmol), DIPEA (12.3 mL; 70.2 mmol) and dimethylamine (2M in THF) (21.1 mL; 42.1 mmol) in DMF (180 mL). The reaction mixture was stirred at rt for the week-end. The solution was poured into ice-water, extracted with EtOAc (2×). The organic layer was washed with brine (2×), then dried over MgSO₄, filtered and evaporated until dryness. The residue was taken-up with diethylether, filtered and dried to give 9.5 g (93%) of intermediate 5.

Preparation of Intermediate 12a and Intermediate 12b

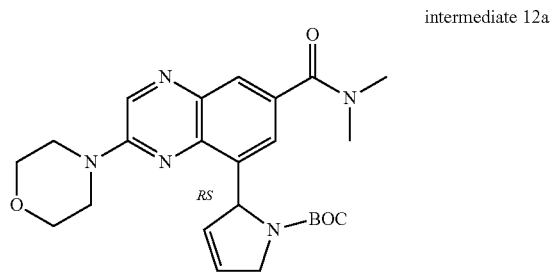

intermediate 12a

-continued

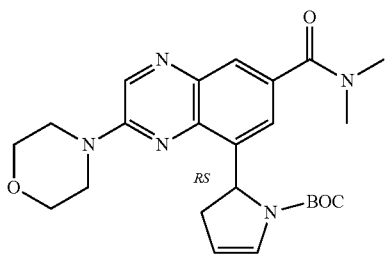
intermediate 12b

In a sealed vessel, a mixture of intermediate 11 (8 g; 21.9 mmol), N-boc-2,3-dihydro-1H-pyrrole (5.3 mL; 30.67 mmol) and $K_2CO_3$ (9.08 g; 65.71 mmol) in anhydrous DMF (200 mL) was degazed under $N_2$. $PPh_3$ (1.15 g; 4.38 mmol) then $Pd(OAc)_2$ (492 mg; 2.19 mmol) were added and the reaction mixture was heated at 100° C. for 15 h. The reaction was cooled down to rt, poured into $H_2O$ and EtOAc was added. The mixture was filtered through a pad of Celite® and the filtrate was extracted with EtOAc. The organic layer was washed with brine, dried over $MgSO_4$, filtered and evaporated until dryness. The residue (12 g) was purified by chromatography over silica gel (irregular SiOH; 15-40 µm; 120 g; gradient: from 0.1% $NH_4OH$, 96% DCM, 4% MeOH to 0.1% $NH_4OH$, 92% DCM, 8% MeOH). The pure fractions were collected and the solvent was evaporated to give 6.2 g (62%, 50/50 by LCMS) of a mixture of intermediates 12a and 12b.

Preparation of Intermediate 13

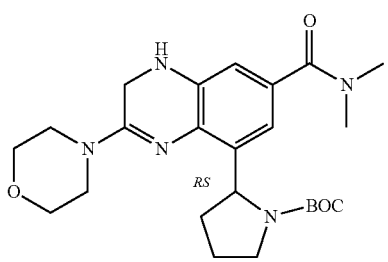 [SMILES: CN(C)C(=O)c1cc2c(c(C3CCCN3C(=O)OC(C)(C)C)c1)N=C(N1CCOCC1)CN2]

A mixture of intermediates 12a and 12b (7 g; 15.43 mmol) and platinum (IV) oxide (713 mg; 3.09 mmol) in EtOH (200 mL) was hydrogenated at rt under a pressure of 1.2 bar of H2 for 4 h. The reaction was filtered through a pad of Celite®, rinsed with MeOH and the filtrate was evaporated to give 6.8 g (97%) of intermediate 13. The product was used without purification for the next step.

Preparation of Intermediate 14

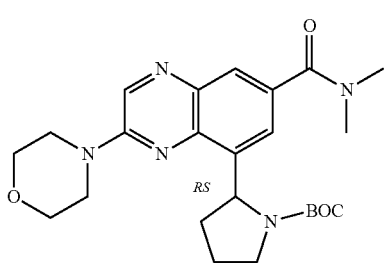 [SMILES: CN(C)C(=O)c1cc(C2CCCN2C(=O)OC(C)(C)C)c2nc(N3CCOCC3)cnc2c1]

A mixture of intermediate 13 (6.8 g; 14.86 mmol), manganese oxide (3.9 g; 44.58 mmol) in DCM (150 mL) was stirred at rt for 1 h. The reaction mixture was filtered through a pad of Celite®, rinsed with MeOH and the filtrate was evaporated to give 7 g (quant.) of intermediate 14. The product was used without purification for the next step.

Preparation of Intermediate 15

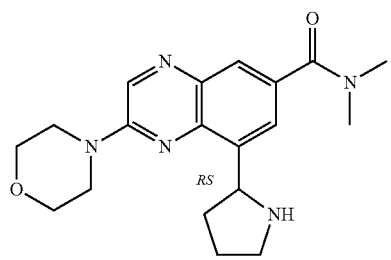 [SMILES: CN(C)C(=O)c1cc(C2CCCN2)c2nc(N3CCOCC3)cnc2c1]

The experiment was performed twice on 3.5 g of intermediate 14:

At 10° C., HCl (4M in 1,4-dioxane) (9.6 mL; 38.41 mmol) was added dropwise to a solution of intermediate 14 (3.5 g; 7.68 mmol) in DCM (115 mL). The reaction mixture was stirred at rt for 5 h. The mixture was taken-up with DCM and iced-water, basified with $NH_4OH$ and extracted with DCM. The organic layer was dried over $MgSO_4$, filtered and evaporated to dryness. The combined residues (5.46 g obtained from 2 experiments) was purified by chromatography over silica gel (irregular SiOH; 15-40 µm; 120 g; mobile phase: 0.1% $NH_4OH$, 90% DCM, 10% MeOH). The pure fractions were collected and the solvent was evaporated to give 3.94 g (72%) of intermediate 15.

Example A4

Preparation of Intermediate 16a and Intermediate 16b

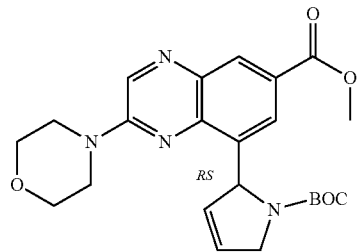
intermediate 16a

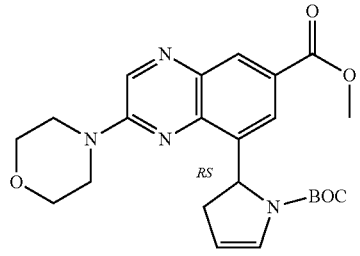
intermediate 16b

A mixture of intermediate 16a and Intermediate 16b was prepared according to an analogous procedure as described for the synthesis of intermediate 12a and 12b, using intermediate 3a as starting material. The residue (3.2 g) was purified by chromatography over silica gel (irregular SiOH; 15-40 µm; 80 g; eluent: 99% DCM, 1% MeOH). The pure fractions were collected and the solvent was evaporated to give 1.9 g (79%) of a mixture of intermediate 16a and intermediate 16b.

Alternative Pathway:

In a sealed glassware, a mixture of intermediate 3a and intermediate 3b (75/25) (10 g; 28.39 mmol), N-boc-2,3-dihydro-1H-pyrrole (6.86 mL; 39.75 mmol) and K$_2$CO$_3$ (11.8 g; 85.18 mmol) in 1,4-dioxane (250 mL) was bubbled with N$_2$. Then, PPh$_3$ (1.49 g; 5.68 mmol) and Pd(OAc)$_2$ (640 mg; 2.84 mmol) were added. The reaction mixture was heated to 100° C. for 5 h. The reaction mixture was cooled down to rt, poured onto water and extracted with EtOAc. The organic layer was decanted, washed with brine, dried over MgSO$_4$, filtered and evaporated to dryness. The residue (21 g) was purified by chromatography over silica gel (irregular SiOH; 20-45 µm; 450 g; mobile phase: 62% heptane, 3% MeOH (+10% NH$_4$OH), 35% EtOAc). The pure fractions were collected and evaporated to dryness yielding 2.3 g (17%, impure) of intermediate 16a and 8.2 g (59%) of intermediate 16a.

Preparation of Intermediate 17

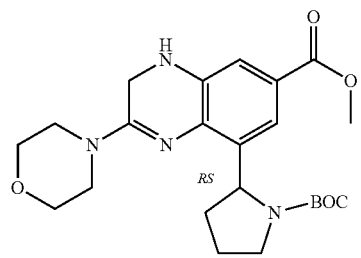 [SMILES: COC(=O)c1cc2c(c(C3CCCN3C(=O)OC(C)(C)C)c1)N=C(N1CCOCC1)CN2]

Intermediate 17 was prepared according to an analogous procedure as described for the synthesis of intermediate 13, using intermediate 16a as starting material. The reaction mixture was stirred at rt for 45 min. Intermediate 17 (11 g, 100%) was directly used without any further purification in the next step.

Preparation of Intermediate 18a, Intermediate 18b and Intermediate 18c

Intermediate 18a

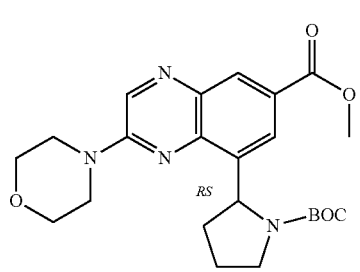

Intermediate 18b

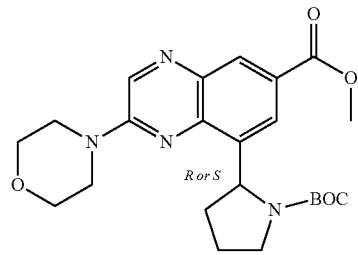

Intermediate 18c

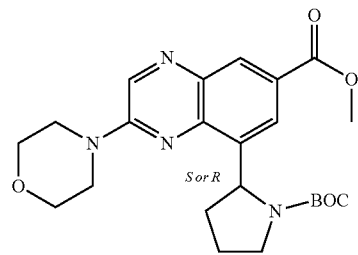

Intermediate 18a was prepared according to an analogous procedure as described for the synthesis of intermediate 14, using intermediate 17 as starting material. The residue (12 g) was purified by chromatography over silica gel (irregular SiOH; 15-40 m; 800 g;

mobile phase: 99% DCM, 1% MeOH). The pure fractions were collected and the solvent was evaporated to give respectively 3.7 g (31%) of intermediate 18a and additional 7.3 g (61%) of intermediate 18a. This last fraction was purified by chiral SFC (Whelk O1 (S,S) 5 µm; 250*21.1 mm; mobile phase: 60% CO$_2$, 40% EtOH). The pure fractions were collected and the solvent was evaporated to give 3.45 g (29%) of intermediate 18b and 3.38 g (28%) of intermediate 18c.

Preparation of Intermediate 19

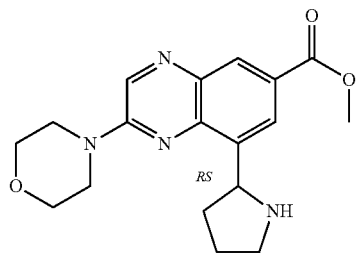 [SMILES: COC(=O)c1cc(C2CCCN2)c2nc(N3CCOCC3)cnc2c1]

Intermediate 19 was prepared according to an analogous procedure as described for the synthesis of intermediate 15, using intermediate 18a as starting material. The reaction mixture was stirred at rt for 15 h. The mixture was poured into DCM and a saturated aqueous solution of NaHCO$_3$ then, extracted with DCM (3×). The organic layer was separated, dried over MgSO$_4$, filtered and evaporated to dryness. The residue was taken-up with Et$_2$O. The precipitate was filtered and dried to give 3.5 g (90%) of intermediate 19.

Preparation of Intermediate 20

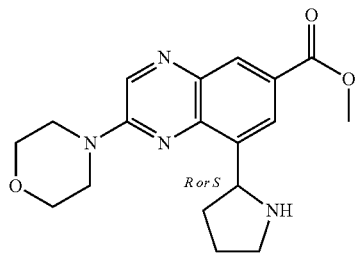 [SMILES: COC(=O)c1cc(C2CCCN2)c2nc(N3CCOCC3)cnc2c1]

Intermediate 20 was prepared according to an analogous procedure as described for the synthesis of intermediate 15, using intermediate 18b as starting material. 8.4 g (88%) of intermediate 20 were obtained.

Example A5

Preparation of Intermediate 20

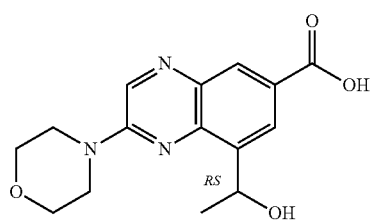 [SMILES: CC(O)c1cc(C(=O)O)cc2ncc(N3CCOCC3)nc12]

Intermediate 20 was prepared according to an analogous procedure as described for the synthesis of intermediate 4, using intermediate 9 as starting material. At 0° C., the solution was acidified with 3N aqueous solution of HCl slowly and stirred at 10° C. for 1 h. The precipitate was filtered and dried to give 1.4 g (39%) of intermediate 20. The filtrate was extracted with DCM (2×). The organic layers were combined, washed with water, dried over MgSO$_4$, filtered and evaporated to give additional 1.8 g (50%, yellow solid) of intermediate 20. The 2 batches were combined to give 3.2 g (89% global yield) of intermediate 20 directly used in the next step without any further purification.

Alternative Pathway:

To a solution of intermediate 9 (1.83 g; 4.50 mmol) in THF (22 mL) and MeOH (22 mL) was added a 1M aqueous solution of sodium hydroxide (13.5 mL; 13.5 mmol). The mixture was stirred at rt overnight and then, evaporated under vacuum. The residue was slowly acidified with a 1N aqueous solution of hydrochloric acid and the precipitate was filtered on a glass-frit to give 1.4 g (quantitative) of intermediate 20 as an off-white solid.

Preparation of Intermediate 21

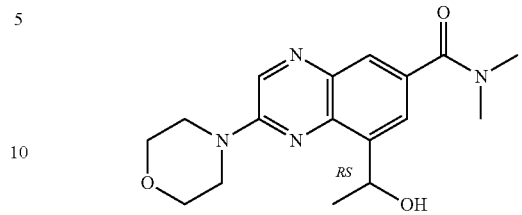

Intermediate 21 was prepared according to an analogous procedure as described for the synthesis of intermediate 5, using intermediate 20 as starting material. The residue was taken-up in EtOAc and a mixture of a saturated aqueous solution of NaHCO$_3$ was added. The aqueous layer was separated and extracted with EtOAc (2×) and DCM/MeOH (9/1) (2×). The combined organic layers were dried over MgSO$_4$, filtered off and evaporated under vacuum. The residue (2.1 g, orange oil) was purified by chromatography over silica gel (regular SiOH; 30 μm; 80 g; gradient: 100% DCM to 30% DCM, 70% EtOAc). The pure fractions were collected and the solvent was evaporated to give 220 mg (14%, orange foam, not pure by NMR) of intermediate 21 and 905 mg (59%, yellow foam) of intermediate 21.

Alternative Pathway:

Intermediate 21 was prepared according to an analogous procedure as described for the synthesis of intermediate 9 (alternative pathway), using intermediate 29 as starting material. The reaction mixture was stirred at 0° C. for 15 min. The mixture was quenched with water and slowly warmed to rt. The aqueous layer was extracted with DCM (2×), then DCM/MeOH (9/1) (2×). The combined organics layers were dried over MgSO$_4$, filtered off and evaporated in vacuum. The residue (1.68 g, pale yellow foam) was purified by chromatography over silica gel (irregular SiOH; 15-40 μm; 50 g; eluent: from 100% DCM to 96% DCM, 4% MeOH). The pure fractions were collected and the solvent was evaporated to give 1.29 g (79%, pale yellow foam) of intermediate 21.

Alternative Pathway:

Intermediate 21 was prepared according to an analogous procedure as described for the synthesis of intermediate 9, using intermediate 29 as starting material. The reaction mixture was stirred at rt for 15 h. Then, DCM and ice-water were added and the mixture was stirred at rt for 1 h. The aqueous layer was extracted with DCM (2×) and the combined organics layers were dried over MgSO$_4$, filtered off and evaporated in vacuum. The residue was taken-up with diethylether, the precipitate was filtered and dried to give 1.73 g (87%) of intermediate 21.

Preparation of Intermediate 22

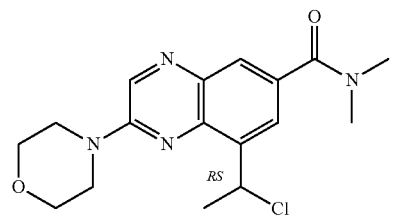 [SMILES: CC(Cl)c1cc(C(=O)N(C)C)cc2ncc(N3CCOCC3)nc12]

Intermediate 22 was prepared according to an analogous procedure as described for the synthesis of intermediate 10, using intermediate 17 as starting material (1 g, >100%). The crude product was used without purification in the next step.

Example A6

Preparation of Intermediate 23

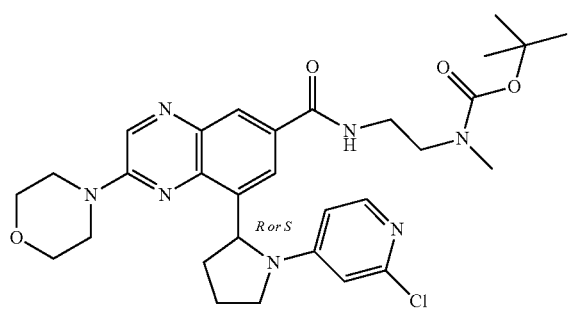 [SMILES: CN(CCNC(=O)c1cc(C2CCCN2c2ccnc(Cl)c2)c2nc(N3CCOCC3)cnc2c1)C(=O)OC(C)(C)C]

To a solution, of compound 17 (400 mg, 0.91 mmol) in DMF (15 mL) were added HBTU (690 mg; 1.82 mmol) and DIPEA (0.94 mL, 5.46 mmol). Then, N-Boc-N-methyl-ethylenediamine (317 mg; 1.82 mmol) was added and the mixture was stirred at rt overnight. The residue was taken up in EtOAc and washed with a 10% aqueous solution of $K_2CO_3$. The aqueous layer was extracted with EtOAc. The combined organic layers were washed with brine (2×), dried over $MgSO_4$, filtered off and evaporated to give 630 mg of intermediate 23.

Preparation of Intermediate 24

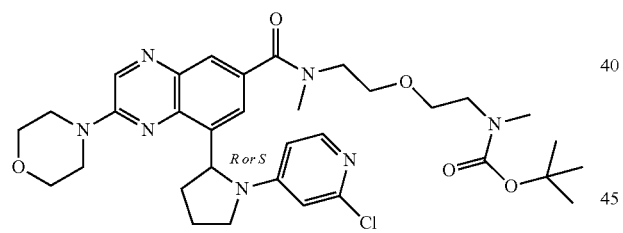

Intermediate 24 was prepared according to an analogous procedure as described for the synthesis of intermediate 23 using compound 17 and t-butyl-N-methyl-N-[2-(2-methyl-aminoethoxy)ethyl]carbamate as starting materials. (400 mg, 43%).

Example A7

Preparation of Intermediate 25

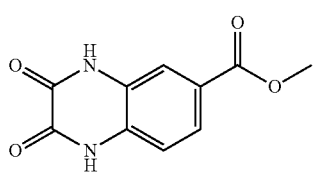 [SMILES: COC(=O)c1ccc2[nH]c(=O)c(=O)[nH]c2c1]

Condensation of methyl 3,4-diaminobenzoate with diethyl oxalate (8.0 equivalents) in toluene (10 volumes) was carried out at reflux for 88 hours. After complete conversion, the mixture was concentrated to a residue which was washed with methyl tert-butyl ether. After drying intermediate 25 was obtained in 90% yield.

Preparation of Intermediate 26

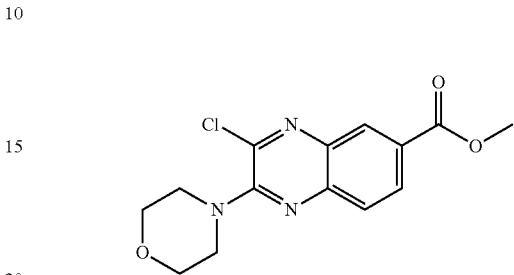

Intermediate 25 was dissolved in 1,2-dichloroethane (10 volumes). Then, dimethylformamide was added (1.0 equivalent) followed by thionyl chloride (4.0 equivalents). The mixture was heated to 80° C. for 3 hours, cooled to 15° C. and water (5 volumes) was slowly added. After phase separation, the organic layer was washed twice with water (10 volumes) and the solvent was exchanged to Me-THF (15 volumes). Triethylamine was added (3.0 equivalents) followed by morpholine (1.0 equivalents) and the reaction was stirred at room temperature. After complete conversion, water (10 volumes) was added and the layers were separated. Then, the aqueous phase was washed with Me-THF (5 volumes). The combined organic layers were washed with water (5 volumes), concentrated to a residue to obtain a solid which was slurried in methyl tert-butyl ether (5 volumes). The precipitate was filtered and dried to give intermediate 26 in 70% yield.

Preparation of Intermediate 27

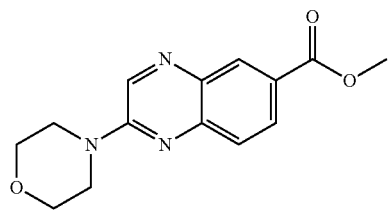 [SMILES: COC(=O)c1ccc2nc(N3CCOCC3)cnc2c1]

Intermediate 26 was dissolved in dichloromethane (10 volumes) and 1,8-diazabicyclo[5.4.0]undec-7-ene (2.0 equivalents) was added. Pd/C (10%, 50% wet, 7% mol) was added and the mixture was hydrogenated (50 psi) for 24 hours. When the conversion was complete, the mixture was filtered through a pad of Celite® and, to the filtrate, $MnO_2$ (0.1 equivalents) was added. The mixture was warmed to 30-40° C. then filtered again on Celite® and the filtrate was concentrated to 1-2 volumes. The solvent was exchanged to methyl tertiobutylether (5-7 volumes) and the mixture was cooled to 5-10° C. and stirred at the same temperature for 2 hours. The solid was filtered and dried to obtain intermediate 27 in 86% yield (99.4% purity).

Example A8

Preparation of Intermediate 28

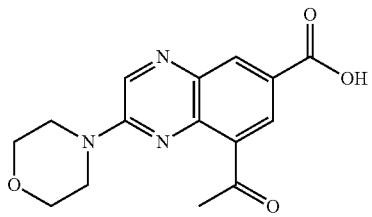 [SMILES: CC(=O)c1cc(C(=O)O)cc2ncc(N3CCOCC3)nc12]

Intermediate 28 was prepared according to an analogous procedure as described for the synthesis of intermediate 4, using intermediate 8a as starting material. The aqueous layer was extracted with DCM (2×). The organic layers were separated, washed with water, dried over MgSO$_4$, filtered and evaporated to dryness. The crude product was taken-up with diethylether, the precipitate was filtered off and dried under vacuum to give 3 g (63%, yellow solid) of intermediate 28. The product was used without purification for the next step.

Alternative Pathway:

A 1M aqueous solution of NaOH (89 mL; 89.0 mmol) was added to a solution of intermediate 8a (9.35 g; 29.7 mmol) in THF (140 mL) and MeOH (140 mL). The reaction mixture was stirred at rt for 1 h then evaporated until dryness under vacuum. The solid obtained was slowly acidified with 1N aqueous solution of HCl and filtered. The cake was dried under vacuum then taken-up in EtOH and evaporated under vacuum to give 8.90 g (quant., yellow solid) of intermediate 28. The product was used without purification for the next step.

Preparation of Intermediate 29

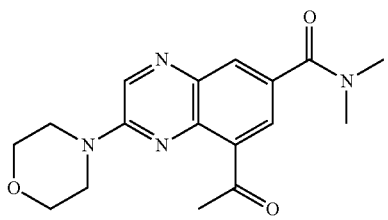 [SMILES: CC(=O)c1cc(C(=O)N(C)C)cc2ncc(N3CCOCC3)nc12]

Intermediate 29 was prepared according to an analogous procedure as described for the synthesis of intermediate 11, using intermediate 28 as starting material. The reaction mixture was stirred at rt for 1 h then evaporated under vacuum. The residue was taken-up in EtOAc and a mixture of a saturated aqueous solution of NaHCO$_3$ and water (50/50) was added. The aqueous layer was separated and extracted with EtOAc (3×). The combined organic layers were washed with a saturated aqueous solution of brine (3×), dried over MgSO$_4$, filtered off and evaporated in vacuum. The residue (14.2 g, orange foam) was purified by chromatography over silica gel (Irregular SiOH; 15-40 μm; 300 g; mobile phase: 30% heptane, 70% EtOAc/MeOH (9/1)). The pure fractions were collected and the solvent was evaporated to give 7.80 g (80%, yellow solid) of intermediate 29.

Preparation of Final Compounds

Example B1

Preparation of Compound 1

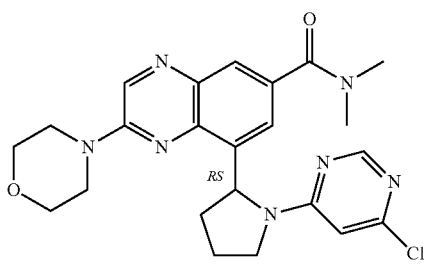 [SMILES: CN(C)C(=O)c1cc(C2CCCN2c2cc(Cl)ncn2)c2nc(N3CCOCC3)cnc2c1]

Under nitrogen in a sealed tube, to a mixture of intermediate 15 (100 mg; 0.28 mmol), 4,6-dichloropyrimidine (63 mg; 0.42 mmol) and cesium carbonate (183 mg; 0.56 mmol) in 1,4-dioxane (3 mL) were added JohnPhos (17 mg; 0.06 mmol) and Pd$_2$(dba)$_3$ (26 mg; 0.03 mmol). The reaction mixture was heated to 100° C. for 24 h. The mixture was poured into water, filtered through a pad of Celite® and extracted with EtOAc. The organic layer was dried over MgSO$_4$, filtered and evaporated until dryness. The crude product (152 mg) was purified via silica gel chromatography (Stationary phase: Spherical bare silica, 5 μm, 150×30.0 mm, Mobile phase: Gradient from 98% DCM, 2% MeOH (+10% NH$_4$OH) to 88% DCM, 12% MeOH (+10% NH$_4$OH)). The pure fractions were collected and evaporated until dryness to give 43 mg of an intermediate fraction which was freeze-dried with acetonitrile/water 20/80 to give 43 mg (33%) of compound 1. M.P=gum at 80° C. (Kofler)

Preparation of Compound 2

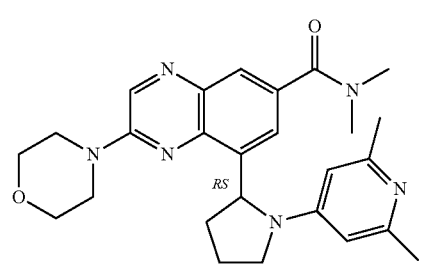 [SMILES: Cc1cc(N2CCCC2c2cc(C(=O)N(C)C)cc3ncc(N4CCOCC4)nc23)cc(C)n1]

Compound 2 was prepared according to an analogous procedure as described for the synthesis of compound 1 using intermediate 15 and 4-bromo-2,6-dimethylpyridine as starting materials (81 mg, 42%). M.P=138° C. (gum, Kofler)

Preparation of Compound 3

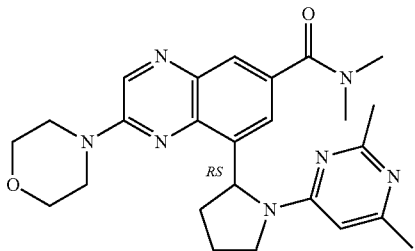 [SMILES: Cc1cc(N2CCCC2c2cc(C(=O)N(C)C)cc3ncc(N4CCOCC4)nc23)nc(C)n1]

A mixture of intermediate 15 4-chloro-2,6-dimethylpyrimidine (150 mg; 0.42 mmol) and cesium carbonate (165 mg; 0.51 mmol) in DMF (3 mL) was heated at 100° C. for 18 h. The reaction was cooled to room temperature and poured into water. EtOAc was added and the organic layer was separated. The organic layer was washed with brine, dried over $MgSO_4$, filtered and evaporated till dryness. The residue was purified by chromatography over silica gel (5 μm 150*30 mm mobile phase: gradient from 98% DCM, 2% MeOH (+10% $NH_4OH$) to 88% DCM, 12% MeOH (+10% $NH_4OH$). The pure fractions were collected and the solvent was evaporated. The residue was crystallized from heptane to give 38 mg (20%) of compound 3. M.P: 186° C. (Kofler)

Preparation of Compound 4

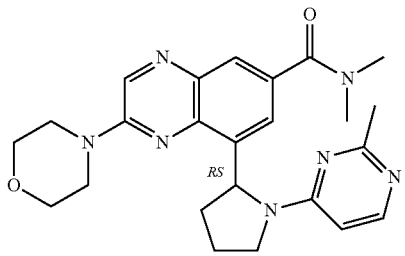 [SMILES: Cc1nccc(N2CCCC2c2cc(C(=O)N(C)C)cc3ncc(N4CCOCC4)nc23)n1]

Compound 4 was prepared according to an analogous procedure as described for the synthesis of compound 3 using intermediate 15 and 4-chloro-2-methylpyrimidine as starting material (69 mg, 37%). M.P.: 110° C. (gum, Kofler).

Preparation of Compound 5

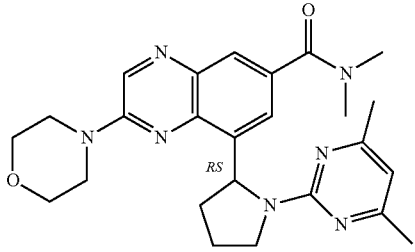 [SMILES: Cc1cc(C)nc(N2CCCC2c2cc(C(=O)N(C)C)cc3ncc(N4CCOCC4)nc23)n1]

Compound 5 was prepared according to an analogous procedure as described for the synthesis of compound 3 using intermediate 15 and 2-chloro-4,6-dimethylpyrimidine as starting materials (55 mg, 28%). M.P. 100° C. (gum, Kofler).

Example B2

Preparation of Compound 6

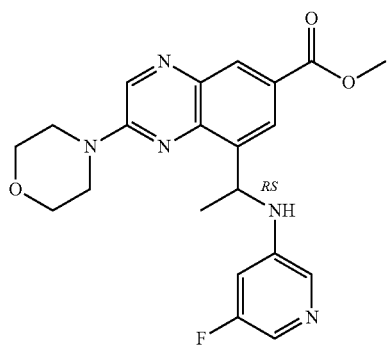 [SMILES: COC(=O)c1cc(C(C)Nc2cncc(F)c2)c2nc(N3CCOCC3)cnc2c1]

In a Shlenk apparatus, intermediate 10 (12.7 g; 37.8 mmol) and 3-amino-5-fluoropyridine (21.2 g; 189 mmol) in DMF (180 mL) were heated at 60° C. for 3 days. The solution was cooled, poured out into iced water, basified with $K_2CO_3$ powder and extracted with EtOAc. The organic layer was washed with $H_2O$ and a saturated NaCl solution, dried over $MgSO_4$ and evaporated to dryness. The residue (18 g) was crystallized from MeOH and $Et_2O$, the precipitate was filtered and dried to give 8.3 g (54%) of compound 6. M.P.: 240° C. (Kofler)

Preparation of Compound 7

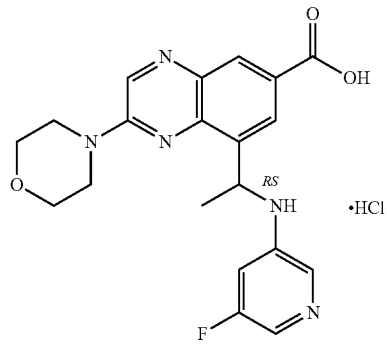 [SMILES: CC(Nc1cncc(F)c1)c1cc(C(=O)O)cc2ncc(N3CCOCC3)nc12 ; Cl]

To a mixture of compound 6 (1.9 g; 4.62 mmol) in THF (95 mL) at room temperature were added lithium hydroxide (1.11 g; 46.2 mmol) and water (19 mL). The mixture was heated at 50° C. for 15 h. The mixture was cooled at room temperature. THF was eliminated by evaporation and the residue was poured onto iced water. Then, the mixture was acidified with a 6N aqueous solution of HCl. The precipitate was filtered and dried giving 1.28 g (64%) of compound 7.

Example B3

Preparation of Compound 8

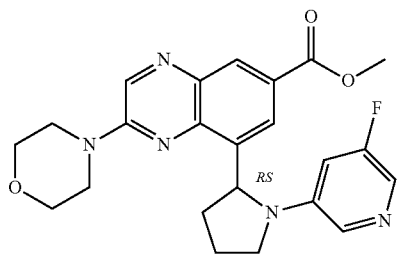 [SMILES: COC(=O)c1cc(C2CCCN2c2cncc(F)c2)c2nc(N3CCOCC3)cnc2c1]

In a sealed tube, a mixture of intermediate 19 (0.15 g; 0.44 mmol), 3-bromo-5-fluoropyridine (0.154 g; 0.88 mmol) and $Cs_2CO_3$ (0.29 g; 0.88 mmol) in 1,4-dioxane (6 mL) was degazed under $N_2$. 2-(Di-tert-butylphosphino)biphenyl (53 mg; 0.18 mmol) and $Pd_2(dba)_3$ (80 mg; 0.088 mmol) were added. The reaction mixture was heated at 100° C. for 18 h. The solution was cooled then, 3-bromo-5-fluoropyridine (0.154 g; 0.88 mmol) and $Cs_2CO_3$ (0.29 g; 0.88 mmol) were added and degazed under $N_2$. 2-(Di-t-butylphosphino)biphenyl (53 mg; 0.18 mmol) and $Pd_2(dba)_3$ (80 mg; 0.088 mmol) were added. The reaction mixture was heated at 100° C. for 18 h. The reaction mixture was poured into ice-water. EtOAc was added. The organic layer was washed with brine, dried over $MgSO_4$, filtered and evaporated. The residue was purified by chromatography over silica gel (irregular, 24 g; mobile phase gradient: 100% DCM to 95% DCM, 5% MeOH). The pure fractions were collected and the solvent was evaporated to give 115 mg (60%) of compound 8.

Preparation of Compound 9

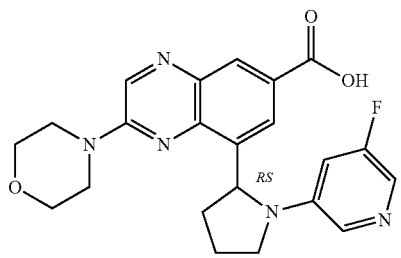 [SMILES: O=C(O)c1cc(C2CCCN2c2cncc(F)c2)c2nc(N3CCOCC3)cnc2c1]

A solution of sodium hydroxide 1M in water (0.8 mL; 0.79 mmol) was added to a solution of a mixture of compound 8 (0.12 g; 0.26 mmol) in Me-THF (1.2 mL) and MeOH (1.2 mL) at rt. The reaction mixture was stirred at rt for 1 h then heated at 60° C. for 1 h. After cooling down to rt, the crude product was evaporated and the residue was slowly acidified with a 1N aqueous solution of HCl. The precipitate was filtered and dried to give 95.2 mg (85%. yellow solid) of compound 9.

Preparation of Compound 10

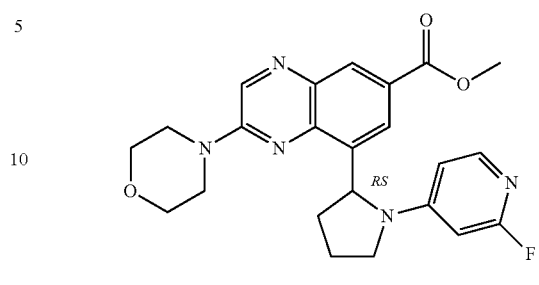

In a sealed glassware, intermediate 19 (250 mg; 0.73 mmol), 2,4-difluoropyridine (93 mg; 0.81 mmol) and $K_2CO_3$ (404 mg; 2.92 mmol) in NMP (1.5 mL) were heated at 80° C. for 18 hours. After cooling down to rt, the solution was poured into water and EtOAc was added. The organic layer was washed with brine, dried over $MgSO_4$, filtered and evaporated. The residue was purified by chromatography over silica gel (irregular SiOH, 30 g; mobile phase gradient: 100% DCM to 98% DCM, 2% MeOH). The fractions containing the product were collected and the solvent was evaporated. The residue (392 mg) was diluted in DCM (70 mL) and washed with water (3×). The organic layer was separated, dried over $MgSO_4$, filtered and evaporated till dryness to give 320 mg of compound 10 as a yellow solid.

Preparation of Compound 11

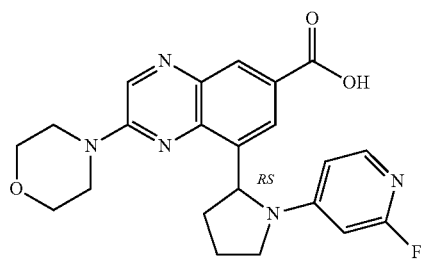 [SMILES: O=C(O)c1cc(C2CCCN2c2ccnc(F)c2)c2nc(N3CCOCC3)cnc2c1]

Intermediate 8 was prepared according to an analogous procedure as described for the synthesis of compound 9 using compound 10 as starting material (271 mg, 87%).

Preparation of Compound 12

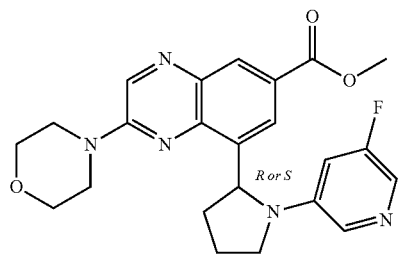 [SMILES: COC(=O)c1cc(C2CCCN2c2cncc(F)c2)c2nc(N3CCOCC3)cnc2c1]

Compound 12 was prepared according to an analogous procedure as described for the synthesis of compound 8 using intermediate 20 and 3-bromo-5-fluoropyridine as starting materials (630 mg, 28%). The reaction was performed into 6 batches from 300 mg of intermediate 20

Preparation of Compound 13

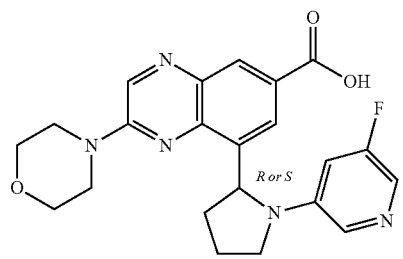 [SMILES: O=C(O)c1cc(C2CCCN2c2cncc(F)c2)c2nc(N3CCOCC3)cnc2c1]

Compound 13 was prepared according to an analogous procedure as described for the synthesis of compound 9 using compound 12 as starting materials (242 mg, 90%).

Preparation of Compound 14

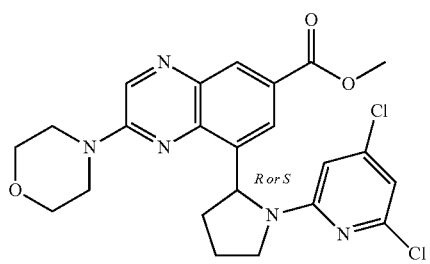 [SMILES: COC(=O)c1cc(C2CCCN2c2cc(Cl)cc(Cl)n2)c2nc(N3CCOCC3)cnc2c1]

In a sealed glassware, intermediate 20 (200 mg; 0.58 mmol), 2,4-dichloro-6-fluoropyridine (97 mg; 0.58 mmol) and DIPEA (0.251 mL; 1.47 mmol) in DMSO (0.6 mL) were heated at 60° C. for 3 hours. After cooling down to rt, the solution was poured into water and EtOAc was added. The organic layer was washed with brine, dried over MgSO$_4$, filtered and evaporated. The residue (273 mg) was purified by chromatography over silica gel (irregular SiOH, 30 g; mobile phase gradient: 100% DCM to 99% DCM, 1% MeOH). The fractions containing the product were collected and the solvent was evaporated to give 320 mg (79%) of compound 14.

Preparation of Compound 15

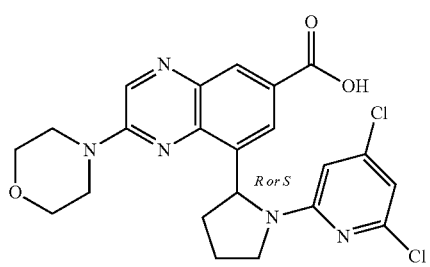 [SMILES: O=C(O)c1cc(C2CCCN2c2cc(Cl)cc(Cl)n2)c2nc(N3CCOCC3)cnc2c1]

Compound 15 was prepared according to an analogous procedure as described for the synthesis of compound 9 using compound 14 as starting material (207 mg, 95%).

Preparation of Compound 16

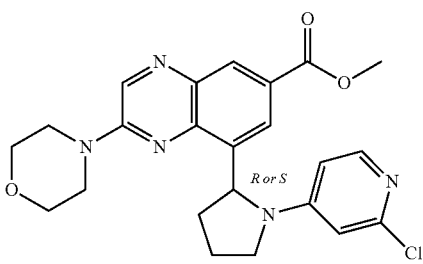 [SMILES: COC(=O)c1cc(C2CCCN2c2ccnc(Cl)c2)c2nc(N3CCOCC3)cnc2c1]

Compound 16 was prepared according to an analogous procedure as described for the synthesis of compound 8 using intermediate 20 and 4-bromo-2-chloropyridine as starting materials (750 mg, 57%).

Preparation of Compound 17

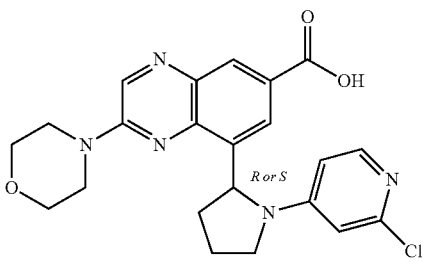 [SMILES: O=C(O)c1cc(C2CCCN2c2ccnc(Cl)c2)c2nc(N3CCOCC3)cnc2c1]

Compound 17 was prepared according to an analogous procedure as described for the synthesis of compound 9 using compound 16 as starting material.

Preparation of Compound 18

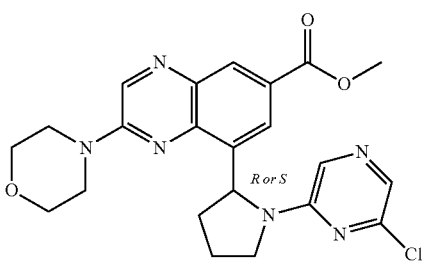 [SMILES: COC(=O)c1cc(C2CCCN2c2cncc(Cl)n2)c2nc(N3CCOCC3)cnc2c1]

Compound 18 was prepared according to an analogous procedure as described for the synthesis of compound 14 using intermediate 20 and 2,6-dichloropyrazine as starting materials. (205 mg, 85%).

Preparation of Compound 19

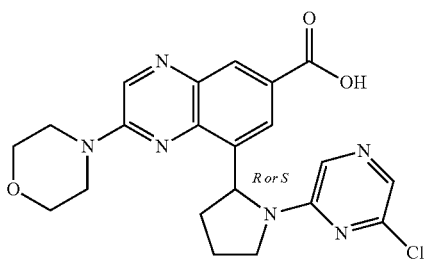

Compound 19 was prepared according to an analogous procedure as described for the synthesis of compound 9 using compound 18 as starting material (189 mg, 95%).

Preparation of Compound 20

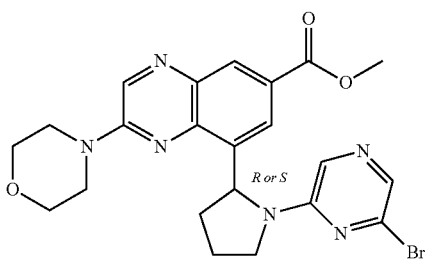 [SMILES: COC(=O)c1cc(C2CCCN2c2cncc(Br)n2)c2nc(N3CCOCC3)cnc2c1]

In a microwave vial, a solution of intermediate 20 (200 mg; 0.58 mmol), 2-bromo-6-fluropyrazine (124 mg; 0.70 mmol) and Et₃N (97.4 µL; 0.70 mmol) in DMF (5 mL) was heated at 100° C. using one single mode microwave (Biotage Initiator EXP 60) with a power output ranging from 0 to 400 W for 1 h [fixed hold time]. After cooling down to rt, the crude was diluted with DCM and water was added. The organic layer was separated and the aqueous layer was extracted with DCM. The combined organic layers were washed with a saturated aqueous solution of NaCl (3×), dried over MgSO₄, filtered off and evaporated under vacuum. The residue (368 mg) was purified by chromatography over silica gel (Irregular SiOH; 15-40 µm, 10 g, mobile phase gradient: from DCM 100% to DCM 99%, MeOH 1%). The fractions containing the product were collected and the solvent was evaporated to give 240 mg (82%) of compound 20 as a yellow solid.

Preparation of Compound 21

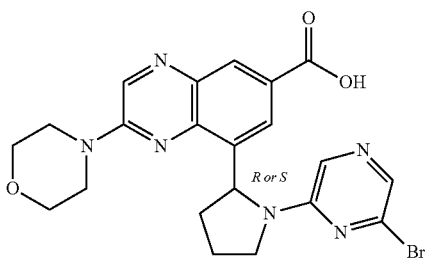 [SMILES: O=C(O)c1cc(C2CCCN2c2cncc(Br)n2)c2nc(N3CCOCC3)cnc2c1]

Compound 21 was prepared according to an analogous procedure as described for the synthesis of compound 9 using compound 20 as starting material (213 mg, 91%).

Preparation of Compound 22

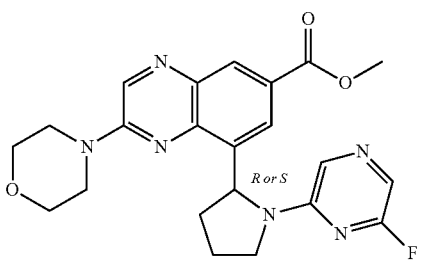 [SMILES: COC(=O)c1cc(C2CCCN2c2cncc(F)n2)c2nc(N3CCOCC3)cnc2c1]

Compound 22 was prepared according to an analogous procedure as described for the synthesis of compound 21 using intermediate 20 as starting materials (213 mg, 83%).

Preparation of Compound 23

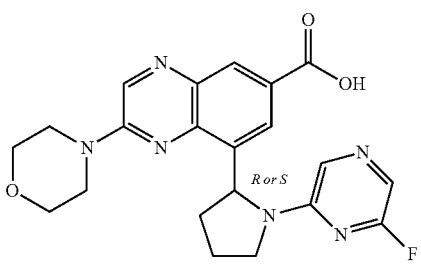 [SMILES: O=C(O)c1cc(C2CCCN2c2cncc(F)n2)c2nc(N3CCOCC3)cnc2c1]

Compound 23 was prepared according to an analogous procedure as described for the synthesis of compound 9 using compound 22 as starting materials (208 mg, quantitative).

Example B4

Preparation of Compound 24

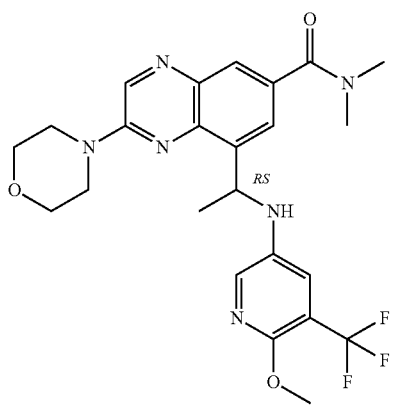 [SMILES: COc1ncc(NC(C)c2cc(C(=O)N(C)C)cc3ncc(N4CCOCC4)nc23)cc1C(F)(F)F]

In a sealed tube, 5-amino-2-methoxy-3-(trifluoromethyl) pyridine (551 mg; 2.87 mmol) was added to a solution of intermediate 22 (250 mg; 0.72 mmol) in DMF (5 mL). The reaction mixture was heated at 60° C. for 72 hours. The solution was cooled to room temperature, poured into cooled water, basified with $K_2CO_3$. EtOAc was added and the organic layer was separated. The organic layer was washed with brine, dried over $MgSO_4$, filtered and evaporated till dryness. The residue (365 mg) was purified by chromatography over silica gel (mobile phase: from 45% Heptane, 5% MeOH, 50% EtOAc, 0.5% $NH_4OH$). The pure fractions were collected and the solvent was evaporated. The residue (200 mg) was purified by chromatography via reverse phase (5 μm 30*150 mm, mobile phase gradient from 60% $NH_4CO_3$, 40% MeOH to 60% $NH_4CO_3$, 100% DCM). The pure fractions were collected and the solvent was evaporated to give 110 mg (30%) of compound 24. M.P: 80° C. (gum, Kofler)

Preparation of Compound 25

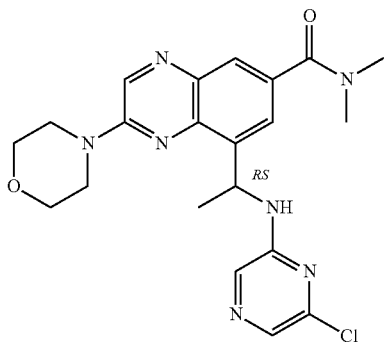 [SMILES: CC(Nc1cncc(Cl)n1)c1cc(C(=O)N(C)C)cc2ncc(N3CCOCC3)nc12]

Compound 25 was prepared according to an analogous procedure as described for the synthesis of compound 24 using intermediate 22 and 2-amino-6-chloropyrazine as starting materials (33 mg, 11%). M.P: 225° C. (DSC).

Preparation of Compound 26

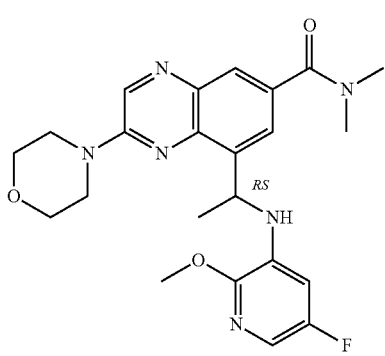 [SMILES: COc1ncc(F)cc1NC(C)c1cc(C(=O)N(C)C)cc2ncc(N3CCOCC3)nc12]

Compound 26 was prepared according to an analogous procedure as described for the synthesis of compound 24 using intermediate 22 and 5-fluoro-2-methoxypyridin-3-amine as starting materials (39 mg, 12%). M.P: 80° C. (gum, Kofler).

Preparation of Compound 27

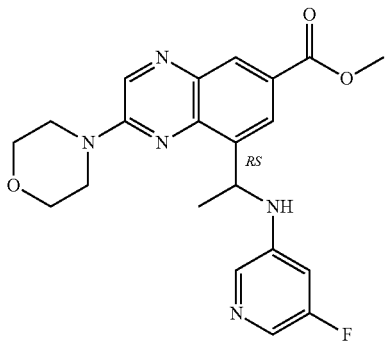 [SMILES: COC(=O)c1cc(C(C)Nc2cncc(F)c2)c2nc(N3CCOCC3)cnc2c1]

Compound 27 was prepared according to an analogous procedure as described for the synthesis of compound 24 using intermediate 10 and 3-amino5-fluoropyridine as starting materials (8.3 g, 54%). M.P: 240° C. (Kofler).

Example B5

Preparation of Compound 28

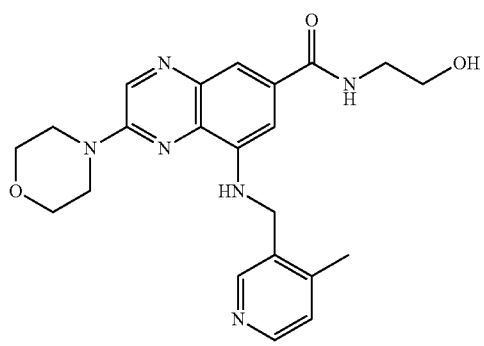 [SMILES: Cc1ccncc1CNc1cc(C(=O)NCCO)cc2ncc(N3CCOCC3)nc12]

TBAF (0.83 mL, 0.83 mmol, 1 M in THF) was added to a mixture of intermediate 6 (405 mg, 0.755 mmol) in THF (1 mL) and the reaction mixture was stirred at rt for 2 hours. The reaction mixture was concentrated and the residue was purified by silica gel chromatography (SiOH, 25 g, mobile phase: 98% DCM 2% MeOH 0.2% $NH_4OH$ to 85% DCM 15% MeOH 1.5% $NH_4OH$) to give 260 mg of fraction A.

Fraction A was crystallized from DIPE to afford 259 mg of fraction B which was taken up with EtOAc and washed with water then a 10% aqueous solution of NaCl. The aqueous layer was extracted with EtOAc. The organic layers were mixed, dried ($MgSO_4$), filtered then concentrated under vacuum to afford 194 mg (61%) of compound 28. M.P: 244° C. (DSC).

Preparation of Compound 29

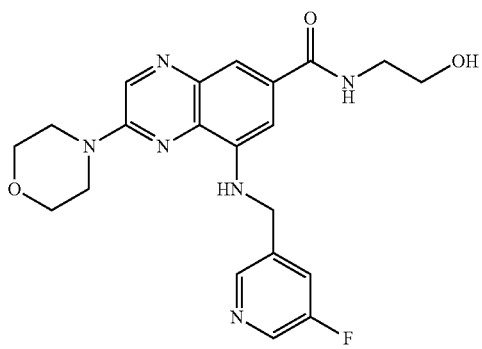 [SMILES: O=C(NCCO)c1cc(NCc2cncc(F)c2)c2nc(N3CCOCC3)cnc2c1]

Compound 29 was prepared according to an analogous procedure as described for the synthesis of compound 28 using intermediate 7 as starting material (0.182 g, 58%).
M.P: 198° C. (DSC).

Preparation of Compound 30, compound 31 and compound 32

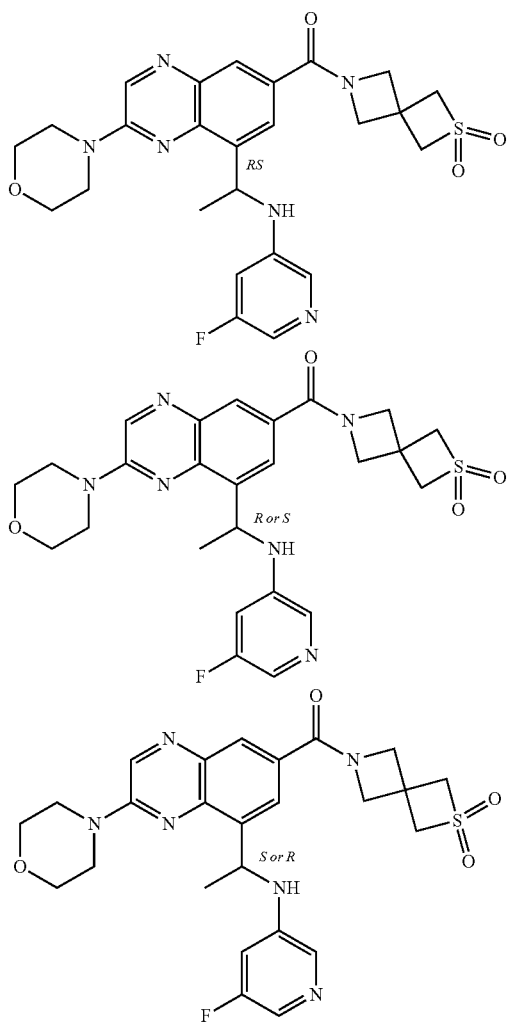

Under N$_2$, 2-thia-6-azaspiro[3.3]heptane,2,2-dioxide (0.58 mg; 2.2 mmol) was added to a solution of compound 7 (0.64 g; 1.475 mmol), HBTU (0.84 g; 2.2 mmol) and DIPEA (1.3 mL; 7.4 mmol) in DMF (20 mL). The solution was stirred at rt for 24 h. The product was poured in iced water and extracted with EtOAc. The organic layer was washed with brine (×2) then, dry over MgSO$_4$, filtered and evaporated until dryness. The residue (950 mg) was purified by chromatography over silica gel (irregular SiOH; 40 g, mobile phase 0.3% NH$_4$OH, 95% DCM, 5% MeOH). The pure fractions were collected and the solvent was evaporated to afford 770 mg (99%) of compound 30 which was purified by chiral SFC (Stationary phase: CHIRALCEL OJ-H 5 μm 250×20 mm, Mobile phase: 60% CO$_2$, 40% (0.3% iPrNH$_2$)). The pure fractions were collected and the solvent was evaporated. The first fraction (195 mg) was crystallized from Et$_2$O. The precipitate was filtered and dried to give (166 mg (22%) of compound 31 (R or S) (M.P.: 160° C. (Kofler)). The second fraction was crystallized from Et$_2$O. The precipitate was filtered and dried to give 174 mg (22%) of compound 32 (S or R) (M.P: 180° C. (Kofler)).

Preparation of Compound 33, Compound 34 and Compound 35

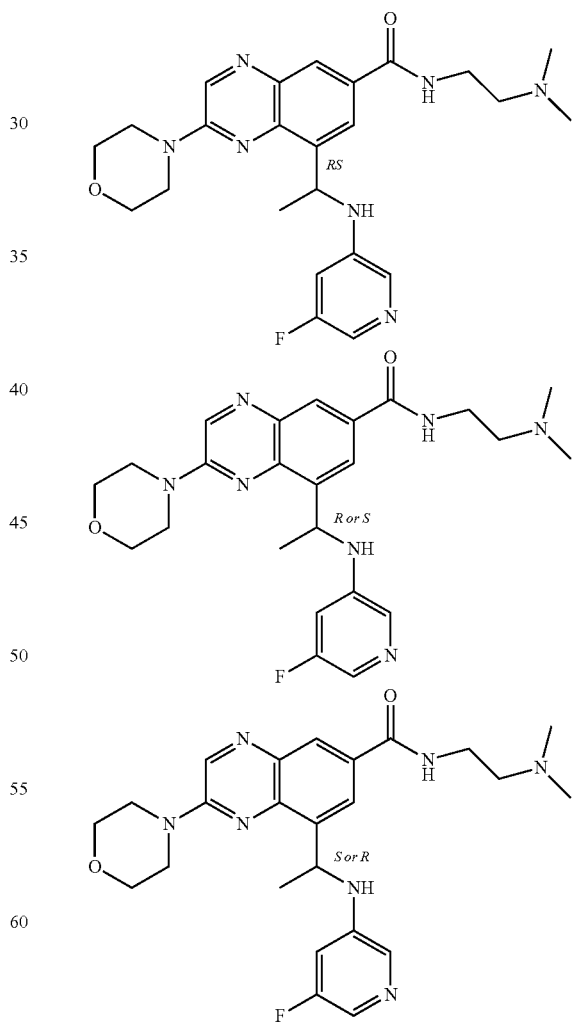

Compound 33, compound 34 and compound 35 were prepared according to an analogous procedure as described for the synthesis of compound 30 using N,N-dimethylethylenediamine as starting materials. After crystallization from Et₂O, the first fraction give 182 mg (27%) of compound 34 (R or S). M.P: 194° C. (DSC). The second fraction gave 186 mg (27%) of compound 35 (S or R), M.P.: 190° C. (DSC).

Preparation of Compound 36

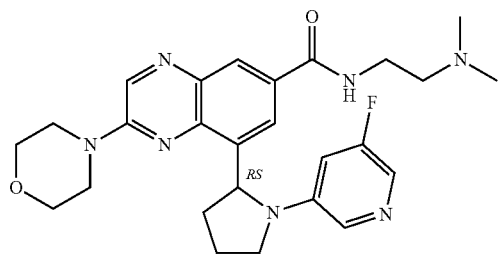 [SMILES: CN(C)CCNC(=O)c1cc(C2CCCN2c2cncc(F)c2)c2nc(N3CCOCC3)cnc2c1]

COMU® (97 g; 0.23 mmol) was added portion wise to a mixture of compound 9 (64 g; 0.15 mmol), DIPEA (0.052 mL; 0.30 mmol) and NN-dimethylethylenediamine (0.02 mL; 0.18 mmol) in DMF (1.5 mL). The reaction mixture was stirred at rt for 2 h. Then, additional N,N-dimethylethylenediamine (0.008 mL; 0.07 mmol) and the stirring was pursued for 1 hour. The reaction mixture was partitioned between water and EtOAc. The organic layer was separated and the aqueous layer was extracted 3 times with EtOAc. The organic layers were mixed, dried over MgSO₄, filtered and concentrated under vacuum. The solution was poured into ice-water, extracted with EtOAc (3×). The organic layer was washed with brine (3×), then dried over MgSO₄, filtered and evaporated until dryness. The residue (127 mg) was purified by chromatography over silica gel (irregular SiOH; 15-40 μm; mobile phase gradient from 100% DCM to, 90% DCM, 10% MeOH/aqNH₃ (95/5)). The pure fractions were collected and the solvent was evaporated to give 51 mg which were dried under vacuum at 50° C. for 18 hours to afford 44 mg (59%) of compound 36 as a pale yellow solid. MP: 206° C., DSC.

Preparation of Compound 37, Compound 38 and Compound 39

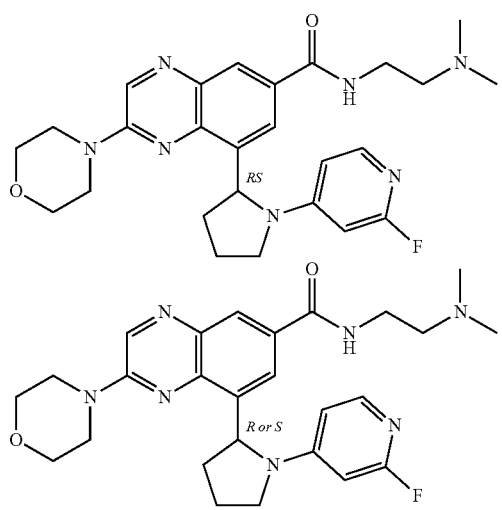

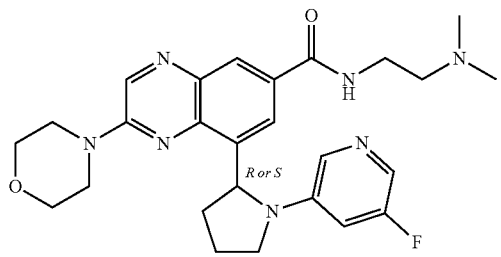 [SMILES: CN(C)CCNC(=O)c1cc(C2CCCN2c2cncc(F)c2)c2nc(N3CCOCC3)cnc2c1]

Compound 37, compound 38 and compound 39 were prepared according to an analogous procedure as described for the synthesis of compound 36 using compound 11 as starting material. Compound 37 (197 mg) was purified by chiral SFC (Stationary phase: CHIRALPAK AD-H 5 μm 250×20 mm, Mobile phase: 60% CO₂, 40% EtOH)). The pure fractions were collected and the solvent was evaporated. The first fraction was crystallized from pentane/Et₂O (5/1). The precipitate was filtered and dried to give (53.9 mg; 17%) of compound 38 (R or S) (M.P.: 177° C. (DSC)). The second fraction was crystallized from pentane/Et₂O (5/1). The precipitate was filtered and dried to give (51.1 mg; 16%) of compound 39 (S or R).

Preparation of Compound 40

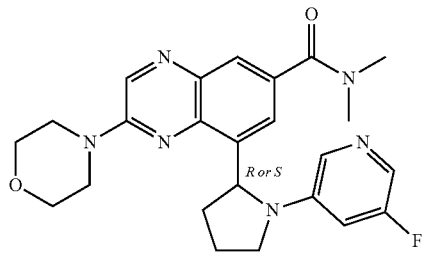 [SMILES: CN(C)C(=O)c1cc(C2CCCN2c2cncc(F)c2)c2nc(N3CCOCC3)cnc2c1]

Compound 40 was prepared according to an analogous procedure as described for the synthesis of compound 36 using compound 13 as starting material. (136 mg; 62%).

Preparation of Compound 41

Compound 41 was prepared according to an analogous procedure as described for the synthesis of compound 36 using compound 13 and dimethylamine solution 2M in THF as starting material. (137 mg; 81%).

Preparation of Compound 42

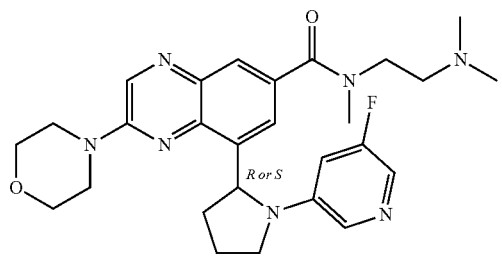 [SMILES: CN(C)CCN(C)C(=O)c1cc(C2CCCN2c2cncc(F)c2)c2nc(N3CCOCC3)cnc2c1]

Compound 42 was prepared according to an analogous procedure as described for the synthesis of compound 36 using compound 13 and N,N,N-trimethylethylenediamine as starting material. (195 mg; 81%).

Preparation of Compound 43

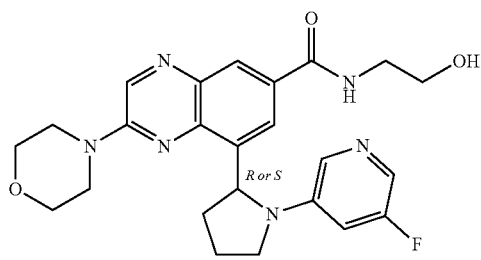 [SMILES: O=C(NCCO)c1cc(C2CCCN2c2cncc(F)c2)c2nc(N3CCOCC3)cnc2c1]

Compound 43 was prepared according to an analogous procedure as described for the synthesis of compound 36 using compound 13 and 2-aminoethanol as starting material. (194 mg; 88%). M.P: 191° C. (Kofler)

Preparation of Compound 44

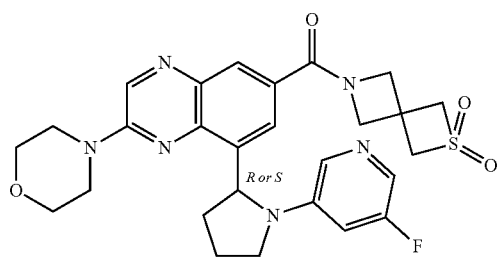 [SMILES: O=C(c1cc(C2CCCN2c2cncc(F)c2)c2nc(N3CCOCC3)cnc2c1)N1CC2(C1)CS(=O)(=O)C2]

Compound 44 was prepared according to an analogous procedure as described for the synthesis of compound 36 using compound 13 and 2-thia-6-aza-spiro[3.3]heptane-2,2-dioxide as starting material. (84 mg; 32%). M.P: 130° C. (Kofler).

Preparation of Compound 45

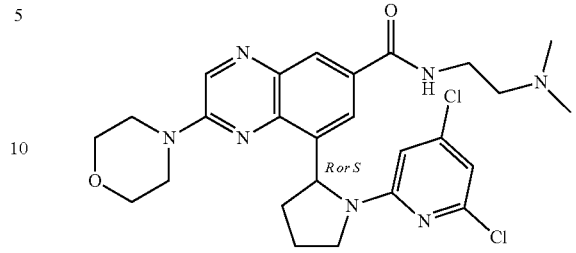

Compound 45 was prepared according to an analogous procedure as described for the synthesis of compound 36 using compound 15 and N,N-Dimethylethylenediamine as starting materials. (152 mg; 64%).

Preparation of Compound 46

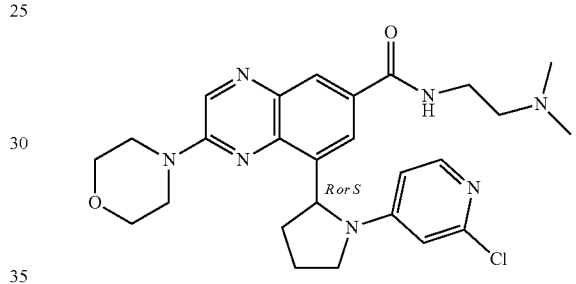

Compound 46 was prepared according to an analogous procedure as described for the synthesis of compound 30 using compound 17 and N,N-dimethylethylenediamine as starting materials. (143 mg; 20%).

Preparation of Compound 47

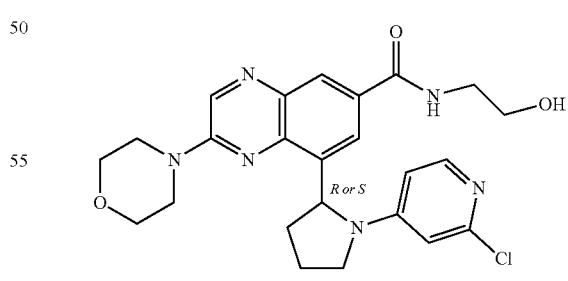

Compound 47 was prepared according to an analogous procedure as described for the synthesis of compound 30 using compound 17 and ethanolamine as starting materials. (52 mg; 12%).

Preparation of Compound 48 ca

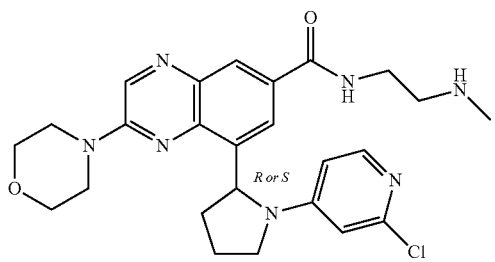 [SMILES: CNCCNC(=O)c1cc(C2CCCN2c2ccnc(Cl)c2)c2nc(N3CCOCC3)cnc2c1]

To a solution of intermediate 23 (630 mg, 1.06 mmol) in 1,4-dioxane (10 mL) was added 3M hydrochloric acid in cyclopentylmethylether (1.0 mL, 6.34 mmol) and the mixture was stirred at 50° C. for 2 h 30 min. Water was added and the mixture was slowly basified with a 10% aqueous solution of $NaHCO_3$. The organic layer was extracted with EtOAc, washed with brine, dry over $MgSO_4$ and evaporated until dryness. The crude (234 mg) was purified by silica gel chromatography (SiOH, 24 g, Mobile phase: gradient: 90% DCM 10% MeOH 1% $NH_4OH$ to 85% DCM 15% MeOH 1.5% $NH_4OH$. The fractions containing the product were collected and evaporated until dryness to give 48 mg of a fraction A which was crystallized in $Et_2O$, filtered and dry under vacuum to give 29 mg of a fraction B (not pure enough). Fraction B and the filtrate of the crystallization were mixed and purified together via silica gel chromatography (SiOH, 24 g, Mobile phase: gradient from: 90% DCM 10% MeOH 1% $NH_4OH$ to 85% DCM 15% MeOH 1.5% $NH_4OH$. The fractions containing the product were collected and evaporated until dryness to give 18 mg which were freeze-dried with acetonitrile/water (20/80) to give 16 mg (3%) of compound 48. M.P: 80° C. (gum, Kofler).

Preparation of Compound 49

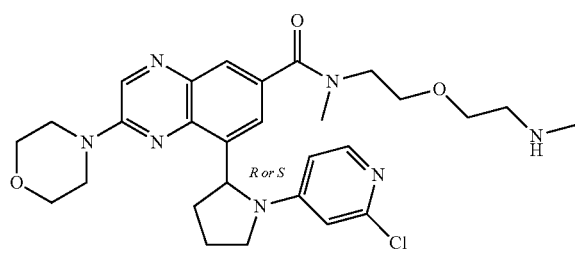 [SMILES: CNCCOCCN(C)C(=O)c1cc(C2CCCN2c2ccnc(Cl)c2)c2nc(N3CCOCC3)cnc2c1]

Compound 49 was prepared according to an analogous procedure as described for the synthesis of compound 48 using intermediate 24 as starting materials. The reaction was heated at 50° C. for 2 h 30 instead of stirred at rt (12 mg; 36%).

Preparation of Compound 50

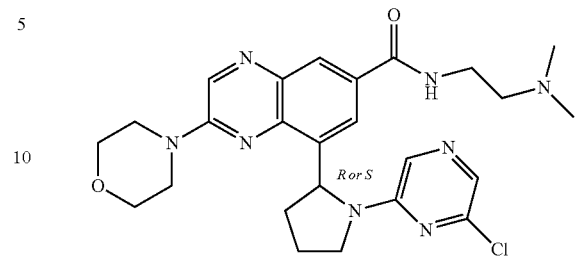

Compound 50 was prepared according to an analogous procedure as described for the synthesis of compound 36 using compound 19 and N,N-dimethylethylenediamine as starting materials (98 mg; 45%).

Preparation of Compound 51

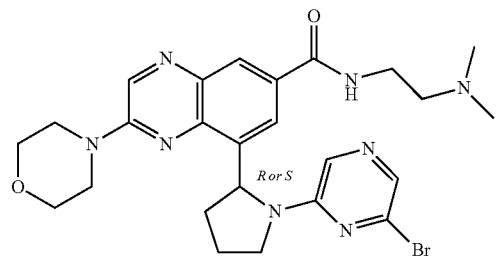 [SMILES: CN(C)CCNC(=O)c1cc(C2CCCN2c2cncc(Br)n2)c2nc(N3CCOCC3)cnc2c1]

Compound 51 was prepared according to an analogous procedure as described for the synthesis of compound 36 using compound 21 and N,N-Dimethylethylenediamine as starting materials (115 mg; 48%).

Preparation of Compound 52

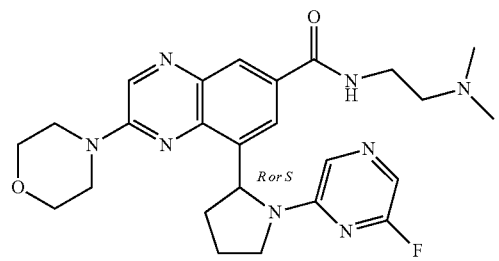 [SMILES: CN(C)CCNC(=O)c1cc(C2CCCN2c2cncc(F)n2)c2nc(N3CCOCC3)cnc2c1]

Compound 52 was prepared according to an analogous procedure as described for the synthesis of compound 36 using compound 23 and N,N-Dimethylethylenediamine as starting materials (115 mg; 48%).

Analytical Part
LCMS (Liquid Chromatography/Mass Spectrometry)
The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc. . . . ). For molecules with multiple isotopic patterns (e.g. Br, Cl), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "DAD" Diode Array Detector.

| LCMS (HPLC) Method codes (Flow expressed in mL/min; column temperature (T) in ° C.; Run time in minutes). | | | | | | |
|---|---|---|---|---|---|---|
| Method code | Instrument | Column | Mobile phase | gradient | Flow Column T | Run time |
| Method 1 | Waters: Acquity UPLC ® - DAD and Quattro Micro ™ | Waters: BEH C18 (1.7 µm, 2.1 × 100 mm) | A: 95% CH₃COONH₄ 7 mM/5% CH₃CN, B: CH₃CN | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H- Class - DAD and SQD 2 | Waters: BEH C18 (1.7 µm, 2.1 × 100 mm) | A: 95% CH₃COONH₄ 7 mM/5% CH₃CN, B: CH₃CN | From 84.2% A to 10.5% A in 2.18 min, held for 1.94 min, back to 84.2% A in 0.73 min, held for 0.73 min. | 0.343 40 | 6.1 |

DSC

For a number of compounds, melting points (MP) were determined with a DSC1 (Mettler-Toledo). Melting points were measured with a temperature gradient of 10° C./minute. Maximum temperature was 350° C. Values are peak values." For a number of compounds, melting points were obtained with a Kofler hot bench, consisting of a heated plate with linear temperature gradient, a sliding pointer and a temperature scale in degrees Celsius.

NMR

The NMR experiments were carried out using a Bruker Avance 500 III using internal deuterium lock and equipped with reverse triple-resonance (¹H, ¹³C, ¹⁵N TXI) probe head and operating at 500 MHz for the proton and 100 MHz for carbon. Chemical shifts (δ) are reported in parts per million (ppm).

OR

Optical Rotation (OR) is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (e.g. Dimethylformamide). The cell is filled with the solution and put into the polarimeter at a temperature of 20° C. The OR is read with 0.004° precision.

Calculation of the concentration: weight in gram×100/volume in ml

Specific rotation $[\alpha]_d^{20}$: (read rotation×100)/(1.000 dm×concentration).

$^d$ is sodium D line (589 nanometer).

TABLE

Co. No. means compound number; Retention time ($R_t$) in min; MP means melting point (° C.); dec means decomposition; n.d. means not determined.

| Co. No. | M.P | K or DSC | Rt | [M + H]⁺ | Method HPLC 1 or 2 |
|---|---|---|---|---|---|
| 1 | 80° C. (gum) | K | 2.41 | 468 | 1 |
| 2 | 138° C. (gum) | K | 1.99 | 461 | 1 |
| 3 | 186° C. | K | 2.18 | 462 | 1 |
| 4 | 110° C. (gum) | K | 2.16 | 448 | 1 |
| 5 | 100° C. (gum) | K | 2.71 | 462 | 1 |
| 6 | 240° C. | K | — | — | — |
| 7 | — | | — | — | — |
| 8 | — | | — | — | — |
| 9 | — | | — | — | — |
| 10 | — | | — | — | — |

TABLE-continued

Co. No. means compound number; Retention time ($R_t$) in min; MP means melting point (° C.); dec means decomposition; n.d. means not determined.

| Co. No. | M.P | K or DSC | Rt | [M + H]⁺ | Method HPLC 1 or 2 |
|---|---|---|---|---|---|
| 11 | — | | — | — | — |
| 12 | — | | — | — | — |
| 13 | — | | — | — | — |
| 14 | — | | — | — | — |
| 15 | — | | — | — | — |
| 16 | — | | — | — | — |
| 17 | — | | — | — | — |
| 18 | — | | — | — | — |
| 19 | — | | — | — | — |
| 20 | — | | — | — | — |
| 21 | — | | — | — | — |
| 22 | — | | — | — | — |
| 23 | — | | — | — | — |
| 24 | 80° C. (gum) | K | 2.79 | 505 | 1 |
| 25 | 225° C. | DSC | 2.46 | 442 | 1 |
| 26 | 80° C. (gum) | K | 2.67 | 455 | 1 |
| 27 | 240° C. | K | — | — | — |
| 28 | 244° C. | DSC | 1.91 | 423 | 1 |
| 29 | 198° C. | DSC | 1.92 | 427 | 1 |
| 31 | 160° C. | K | 2.23 | 527 | 1 |
| 32 | 180° C. | K | 2.23 | 527 | 1 |
| 33 | — | | — | — | — |
| 34 | 194° C. | DSC | 2.03 | 468 | 1 |
| 35 | 190° C. | DSC | 2.02 | 468 | 1 |
| 36 | 206° C. | DSC | 2.14 | 494 | 1 |

TABLE-continued

Co. No. means compound number; Retention time (R$_t$) in min; MP means melting point (° C.); dec means decomposition; n.d. means not determined.

| Co. No. | M.P | K or DSC | Rt | [M + H]+ | Method HPLC 1 or 2 |
|---|---|---|---|---|---|
| 37 | — | — | — | — | — |
| 38 | 177° C. | DSC | 2.10 | 494 | 1 |
| 39 | — | — | 2.10 | 494 | 1 |
| 40 | — | — | 2.19 | 494 | 1 |
| 41 | — | — | 2.52 | 451 | 1 |
| 42 | — | — | 2.29 | 508 | 1 |
| 43 | 191° C. | DSC | 2.25 | 467 | 1 |
| 44 | 130° C. | K | 2.39 | 553 | 1 |
| 45 | — | — | 2.88 | 544 | 1 |
| 46 | — | — | 2.13 | 510 | 1 |
| 47 | — | — | 2.23 | 483 | 1 |
| 48 | 80° C. (gum) | K | 2.08 | 496 | 1 |
| 49 | — | — | 2.1 | 554 | 1 |
| 50 | — | — | 2.31 | 511 | 1 |
| 51 | — | — | 2.42 | 555 | 1 |
| 52 | — | — | 2.21 | 495 | 1 |

OR data: Solvent: DMF; temperature: 20° C.; wavelength: 589 nm ('Co. No.' means Compound Number; 'OR' means optical rotation (specific rotation); 'Conc.' means concentration in g/100 mL)

| Co. No. | OR (°) | Concentration |
|---|---|---|
| 31 | −310.16 | 0.315 |
| 32 | +320.54 | 0.331 |
| 34 | −403.85 | 0.26 |
| 35 | +377.67 | 0.309 |
| 38 | −296.54 | 0.26 |
| 39 | +302.59 | 0.27 |
| 40 | −266.4 | 0.245 |
| 41 | −300.36 | 0.276 |
| 42 | −271.78 | 0.287 |
| 43 | −338.08 | 0.281 |
| 44 | −231.86 | 0.211 |
| 45 | −390.18 | 0.275 |
| 46 | −343.2 | 0.25 |
| 47 | −359.04 | 0.271 |
| 48 | −320.66 | 0.213 |
| 49 | −275.57 | 0.22 |
| 50 | −348.48 | 0.264 |
| 51 | −336.62 | 0.284 |
| 52 | −326.97 | 0.267 |

$^1$H NMR Data:

Compound 44:

$^1$H NMR (500 MHz, DMSO-d$_6$) δ ppm 8.96 (s, 1H) 7.96 (d, J=1.3 Hz, 1H) 7.73 (d, J=1.9 Hz, 1H) 7.55 (br s, 1H) 7.41 (s, 1H) 6.62 (br d, J=12.0 Hz, 1H) 5.66 (br d, J=8.2 Hz, 1H) 4.32-4.62 (m, 6H) 4.25 (br s, 2H) 3.70-3.98 (m, 9H) 3.41-3.53 (m, 1H) 2.53-2.60 (m, 1H, partially hidden by solvent peak) 2.01-2.10 (m, 1H) 1.83-2.00 (m, 2H)

Compound 40:

$^1$H NMR (500 MHz, CHLOROFORM-d) δ ppm 8.67 (s, 1H) 8.16 (d, J=0.9 Hz, 1H) 7.79 (d, J=1.3 Hz, 1H) 7.72 (d, J=1.9 Hz, 1H) 7.65 (s, 1H) 6.90-7.14 (m, 1H) 6.40 (br d, J=11.7 Hz, 1H) 5.68 (br d, J=7.6 Hz, 1H) 3.73-4.02 (m, 9H) 3.41-3.58 (m, 3H) 2.46-2.61 (m, 3H) 2.27 (s, 6H) 1.97-2.21 (m, 3H)

Compound 34:

$^1$H NMR (500 MHz, DMSO-d$_6$) δ ppm 8.94 (s, 1H) 8.53 (br t, J=5.5 Hz, 1H) 8.26 (d, J=1.6 Hz, 1H) 8.10 (s, 1H) 7.74 (s, 1H) 7.59 (d, J=2.2 Hz, 1H) 7.05 (br d, J=6.9 Hz, 1H) 6.51 (br d, J=12.3 Hz, 1H) 5.48 (quin, J=6.6 Hz, 1H) 3.72-3.95 (m, 8H) 3.35-3.38 (m, 2H) 2.39 (t, J=6.8 Hz, 2H) 2.16 (s, 6H) 1.52 (d, J=6.9 Hz, 3H)

Pharmacology Update

Enzyme Binding Assays (KINOMEscan®)

Kinase enzyme binding affinities of compounds disclosed herein were determined using the KINOMEscan technology performed by DiscoveRx Corporation, San Diego, Calif., USA (www.kinomescan.com). Table A reports the obtained Kd values (nM), with the Kd being the inhibitor binding constant:

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 1 | 16596 | 42 | 1413 | >30200 | >30200 |
| 5 | 5370 | 22 | 832 | 26915 | >30200 |
| 4 | 28840 | 1549 | 22387 | >30200 | >30200 |
| 2 | >30200 | 162 | 5888 | 20893 | >30200 |
| 3 | >30200 | 2042 | 25119 | >30200 | >30200 |
| 25 | 16218 | 21 | 1318 | 28840 | >30200 |
| 24 | >30200 | 589 | 8318 | >30200 | >30200 |
| 26 | 5012 | 15 | 661 | >30200 | >30200 |
| 47 | 16982 | 32 | 1950 | 20893 | 21878 |
| 48 | 10000 | 2 | 372 | 18197 | >30200 |
| 46 | 13490 | 2 | 550 | 19498 | >30200 |
| 49 | >30200 | 28 | 2455 | >30200 | >30200 |
| 36 | 1698 | 0, 1 | 295 | 3388 | >30200 |
| 38 | 11482 | 8 | 1413 | 20893 | >30200 |
| 39 | 19055 | 1072 | 31623 | >30200 | 19498 |
| 44 | 575 | 2 | 240 | 4074 | 31623 |
| 40 | 490 | 0.2 | 120 | 1047 | >30200 |
| 50 | 1660 | 0.9 | 162 | 3311 | >30200 |
| 45 | 479 | 0.3 | 32 | 457 | 12303 |
| 42 | 646 | 0.5 | 46 | 2630 | >30200 |
| 43 | 447 | 3 | 166 | 1000 | 11482 |
| 51 | 9120 | 20 | 3467 | >30200 | >30200 |
| 41 | 209 | 0.8 | 52 | 1047 | >30200 |
| 31 | 2818 | 9 | 1479 | 16596 | >30200 |
| 32 | >30200 | 5495 | 22387 | >30200 | >30200 |
| 34 | 2188 | 0.4 | 166 | 3890 | >30200 |
| 35 | 15488 | 8 | 1445 | 4786 | 12023 |
| 28 | 16218 | 1259 | 15488 | 25704 | 30903 |
| 29 | 14791 | 195 | 6918 | >30200 | >30200 |
| 57 | 4365 | 1 | 295 | 5623 | >30200 |

Cellular Assays:

Cellular activity of PI3Kβ inhibitors was determined by quantifying the phosphorylation of Akt in PC-3 cells. Akt phosphorylated at Ser473 and Thr308 were measured using an enzyme-linked immunosorbent assay (ELISA; Meso Scale Discovery (MSD), Gaithersburg, Md.) and specific primary antibodies from MSD.

On day 1, PC3 cells (ATCC #CRL-14351) were seeded into PerkinElmer MW96 plates at 25.000 cells per well, in 75 µl complete culture medium (DMEM high glucose, AQmedia™, D0819, Sigma-Aldrich) containing 10% heat inactivated FCS and incubated at 37° C., 5% CO$_2$ during 24 hours. On day 2, compound or DMSO (0.3%) was added and cells were further incubated for 60 min at 37° C., 5% CO$_2$ in a total volume of 100 µl of medium.

The phosphoprotein assay was executed according to vendor instructions in the Phospho-Akt (Ser473) Assay Whole Cell Lysate Kit (MSD #K15100D-3) and the Phospho-Akt (Thr308) Assay Whole Cell Lysate Kit (MSD #K151DYD-3) using the lysis, blocking and wash buffer provided.

Briefly, at the end of the cell treatment period, media were removed by aspiration and adherent cells were lysed in 50 µl ice-cold lysis buffer. MSD plates are supplied pre-coated with capture antibodies for Phospho-Akt (Ser473 and Thr308). After blocking, lysates from tissue culture plates were added and plates were washed. Then, a solution containing the detection antibody (anti-total Akt conjugated with an electrochemiluminescent compound-MSD Sulfo-tag label) was added. The signals were detected using an MSD SECTOR Imager 6000 and are proportional to the phospho-Akt titres.

Data were processed. The percentage of inhibition was plotted against the log concentration of test compounds, and the sigmoidal log concentration-effect curve of best fit was calculated by nonlinear regression analysis. From these concentration-response curves, the $IC_{50}$ values were calculated. Five concentrations were used for curve fitting.

TABLE B reports the obtained $IC_{50}$ values (nM):

| Co. No. | $IC_{50}$ pAkt_S473 (nM) | $IC_{50}$ pAkt_Thr308 (nM) |
|---|---|---|
| 1 | >513 | >513 |
| 5 | >513 | 417 |
| 4 | >513 | >513 |
| 2 | >513 | >513 |
| 3 | >513 | >513 |
| 25 | >513 | 468 |
| 24 | >513 | >513 |
| 26 | >513 | 191 |
| 47 | >513 | >513 |
| 48 | >513 | >513 |
| 46 | 102 | 66 |
| 49 | >513 | >513 |
| 36 | 5 | 4 |
| 38 | 11 | 59 |
| 39 | >513 | >513 |
| 44 | 49 | 30 |
| 40 | 2 | 2 |
| 50 | 19 | 12 |
| 45 | 7 | 4 |
| 42 | 2 | 1 |
| 43 | ~62 | 40 |
| 51 | >513 | >513 |
| 41 | ~17 | 3 |
| 31 | >513 | ~72 |
| 32 | >513 | >513 |
| 34 | 14 | 7 |
| 35 | >513 | >513 |
| 28 | >513 | >513 |
| 29 | >513 | >513 |
| 52 | >513 | >513 |

Prophetic Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

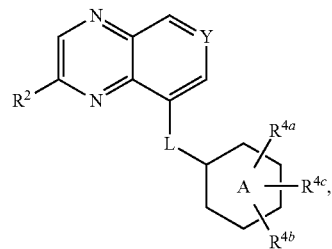

(I)

a tautomer or a stereoisomeric form thereof, wherein

Y represents $CR^3$ or N;

L represents —CH($C_{1-4}$alkyl)-$CH_2$—, —$CH_2$—CH($C_{1-4}$alkyl)-,
—CH($C_{1-4}$alkyl)-CH($C_{1-4}$alkyl)-, —$CHR^{1a}$—X—, or —X—$CHR^{1c}$—;

X represents O, S, or $NR^{1b}$;

$R^{1a}$ represents $C_{1-4}$alkyl;

$R^{1c}$ represents hydrogen or $C_{1-4}$alkyl;

$R^{1b}$ represents hydrogen, $C_{1-4}$alkyl, —$CH_2$—C(=O)—$NR^{6a}R^{6b}$, or $C_{1-4}$alkyl substituted with one substituent selected from the group consisting of hydroxyl, —O—$C_{1-4}$alkyl, and
—$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—;

$R^2$ represents

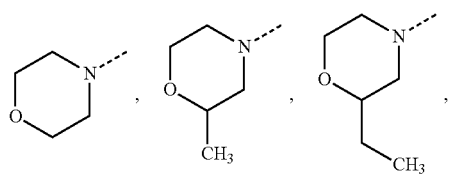

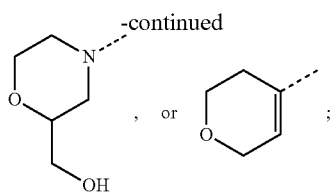

$R^{6a}$ and $R^{6b}$ each independently are selected from the group consisting of hydrogen and $C_{1-4}$alkyl;

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —$NH(C_{1-4}$alkyl), and —$N(C_{1-4}$alkyl$)_2$;

$R^3$ represents $R^7$, —(C=O)H, —(C=O)—$C_{1-4}$alkyl, —(C=O)—$NR^{5a}R^{5b}$, (C=O)—$OR^{5c}$, —C(=O)-Het$^1$, —C(=O)—NH-Het$^2$, $C_{1-4}$alkyl, —CH=N—OH, —CH(OH)—$CH_2$—$NR^{5d}R^{5e}$, —CH(OH)—$CH_2$-Het$^1$, —CH(OH)—$C_{1-4}$alkyl, —C(OH)($C_{1-4}$alkyl$)_2$, halo, or $R^3$ represents $C_{1-4}$alkyl substituted with one substituent selected from the group consisting of hydroxyl, fluoro, —$NR^{5f}R^{5g}$,Het$^1$, —O—(C=O)—CH($NH_2$)—$C_{1-4}$alkyl, O—(C=O)—CH($NH_2$)—$C_{1-4}$alkyl-Ar,

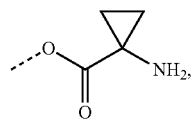

—O—$C_{1-4}$alkyl-OH, and
—O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl$)_2$, —$NH_2$, —NH($C_{1-4}$alkyl) and —N($C_{1-4}$alkyl$)_2$;

$R^{5c}$ represents hydrogen or $C_{1-4}$alkyl;

$R^{5d}$ and $R^{5e}$ each independently are selected from the group consisting of hydrogen and $C_{1-4}$alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl$)_2$;

Ring

represents a 6-membered aromatic ring containing 1 or 2 N-atoms;

$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —$NH(C_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —$NH(C_{1-4}$alkyl), and hydroxyl;

Het$^1$ represents a monocyclic 4-, 5-, 6- or 7-membered saturated or partially saturated heterocyclyl containing at least one heteroatom each independently selected from O, S, S(=O)$_p$ and N; or Het$^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —$NR^{9a}R^{9b}$, $C_{1-4}$alkyl, —(C=O)—$OR^{5h}$, —S(=O)$_2$—$C_{1-6}$alkyl, —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —$NH(C_{1-4}$alkyl) and —$N(C_{1-4}$alkyl$)_2$; or two substituents on the same carbon atom of said heterocyclyl are taken together to form together with the common carbon atom to which they are attached Ring B;

$R^{9a}$ and $R^{9b}$ each independently are selected from the group consisting of hydrogen, $C_{1-4}$alkyl, and $C_{1-4}$alkyl substituted with one or more halo atoms;

Het$^2$ represents

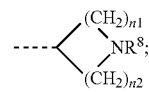

n1 represents 1 or 2;

n2 represents 1 or 2;

$R^8$ represents hydrogen, $C_{1-4}$alkyl, or $C_{1-4}$alkyl substituted with one or more halo atoms;

$R^{5h}$ represents hydrogen or $C_{1-4}$alkyl;

Ring B represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

p represents 1 or 2;

Ar represents phenyl optionally substituted with one hydroxyl;

R⁷ represents

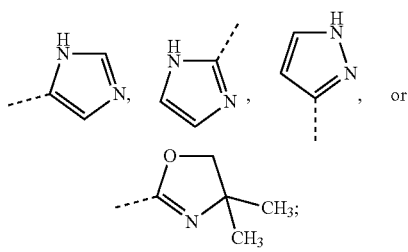

or a N-oxide, a pharmaceutically acceptable addition salt or a solvate thereof.

2. The compound according to claim 1, wherein
Y represents $CR^3$;
$R^3$ represents —(C=O)H, —(C=O)—$C_{1-4}$alkyl, —(C=O)—$NR^{5a}R^{5b}$, —(C=O)—$OR^{5c}$, —C(=O)-Het¹, or —C(=O)—NH-Het².

3. The compound according to claim 1, wherein
Y represents $CR^3$;
L represents —$CHR^{1a}$—X—, or —X—$CHR^{1c}$—;
X represents $NR^{1b}$;
$R^{1a}$ represents $C_{1-4}$alkyl;
$R^{1c}$ represents hydrogen;
$R^{1b}$ represents hydrogen;
or $R^{1b}$ is taken together with $R^{1a}$ or $R^{1c}$ to form —(CH₂)₃—;
$R^2$ represents

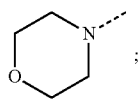

$R^3$ represents —(C=O)—$NR^{5a}R^{5b}$, —(C=O)—$OR^{5c}$, or —C(=O)-Het¹;
$R^{5a}$ and $R^{5b}$ each independently are selected from the group consisting of hydrogen, $C_{1-4}$alkyl, and
$C_{1-4}$alkyl substituted with one substituent selected from the group consisting of hydroxyl, —O—$C_{1-4}$alkyl-NH($C_{1-4}$alkyl), —NH($C_{1-4}$alkyl) and —N($C_{1-4}$alkyl)₂;
$R^{5c}$ represents hydrogen or $C_{1-4}$alkyl;
Ring

represents a 6-membered aromatic ring containing 1 or 2 N-atoms;
$R^{4a}$, $R^{4b}$ and $R^{4c}$ each independently are selected from the group consisting of hydrogen, $C_{1-4}$alkyl, halo, —O—$C_{1-4}$alkyl, and $C_{1-4}$alkyl substituted with one or more halo substituents;
Het¹ represents a monocyclic 4-membered saturated heterocyclyl containing at least one N-atom; wherein two substituents on the same carbon atom of said heterocyclyl are taken together to form together with the common carbon atom to which they are attached Ring B;
Ring B represents 4-membered saturated heterocyclyl containing at least one $S(=O)_p$;
p represents 2.

4. The compound according to claim 1, wherein Het¹ represents

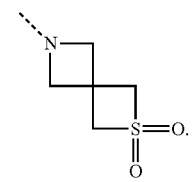

5. The compound according to claim 1, wherein $R^{1b}$ is taken together with $R^{1a}$ or $R^{1c}$ to form —(CH₂)₃—.

6. The compound according to claim 1, wherein
L represents —$CHR^{1a}$—X—;
X represents $NR^{1b}$;
$R^{1b}$ is taken together with $R^{1a}$ to form —(CH₂)₃—.

7. The compound according to claim 1, wherein $R^2$ represents

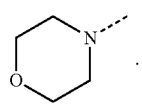

8. The compound according to claim 1, wherein Y represents $CR^3$.

9. A pharmaceutical composition comprising a pharmaceutically acceptable carrier and, as active ingredient, a therapeutically effective amount of a compound according to claim 1.

10. A method of treating prostate cancer in a subject comprising administering a therapeutically effect amount of a compound of claim 1.

* * * * *